United States Patent [19]
Kim et al.

[11] Patent Number: 6,153,579
[45] Date of Patent: Nov. 28, 2000

[54] CRYSTALLIZABLE COMPOSITIONS COMPRISING A HEPATITIS C VIRUS NS3 PROTEASE DOMAIN/NS4A COMPLEX

[75] Inventors: Joseph L. Kim, Natick, Mass.; Kurt A. Morgenstern, Derry, N.H.; Chao Lin, Cambridge, Mass.; Ted Fox, Maynard, Mass.; John A. Thomson, Belmont, Mass.

[73] Assignee: Vertex Pharmaceuticals, Incorporated, Cambridge, Mass.

[21] Appl. No.: 08/731,336

[22] Filed: Oct. 18, 1996

Related U.S. Application Data

[60] Provisional application No. 60/025,274, Sep. 12, 1996.

[51] Int. Cl.[7] .............................. A61K 38/16; C07K 14/18
[52] U.S. Cl. .................................. 514/2; 514/12; 514/13; 530/324; 530/325; 530/326; 530/350; 424/184.1; 424/185.1; 424/189.1; 424/225.1
[58] Field of Search .................................. 514/2, 12, 13; 530/350, 324, 325, 326; 424/184.1, 185.1, 189.1, 225.1

[56] References Cited

U.S. PATENT DOCUMENTS

| | | | |
|---|---|---|---|
| 4,833,233 | 5/1989 | Carter | 530/363 |
| 5,353,236 | 10/1994 | Subbiah | 364/499 |

FOREIGN PATENT DOCUMENTS

| | | | |
|---|---|---|---|
| WO 94/25860 | 10/1994 | WIPO | G01N 24/00 |
| WO 95/22985 | 8/1995 | WIPO | A61K 38/43 |

OTHER PUBLICATIONS

Satoh et al. 'The N–Terminal Region of Hepatitis C Virus Nonstructural Protein 3(NS3) is Essential for Stable Complex Formation with NS4A', J. of Virology. vol. 69, No. 7, pp. 4255–4260, Jul. 1995.

P.N. Bryan, "Protein Engineering", *Biotech Adv.*, 5, pp. 221–234 (1987).

I.D. Campbell et al., "Diffraction, in Biological Spectroscopy", *The Benjamin/Cummings Publishing Company, Inc.*, Menlo Park, CA, pp. 299–326 (1984).

J. Jancarik et al., "Sparse Matrix Sampling: A Screening Method for Crystallization of Proteins", *J. Appl. Cryst.*, 24, pp. 409–411 (1991).

A. Kajihara et al., "Protein Modelling Using a Chimera Reference Protein Derived From Exons", *Protein Eng'g*, 6, pp. 615–620 (1993).

D. Musil et al., "The Refined 2.15 Å X–Ray Crystal Structure of Human Liver Cathepsin B: the Structural Basis for its Specificity", *EMBO J.*, 10(9), pp. 2321–2330 (1991).

A.J. Russell et al., "Rational Modification of Enzyme Catalysis by Engineering Surface Charge", *Nature*, 328, pp. 496–500 (1987).

A.R. Sielecki et al., "Structure of Recombinant Human Renin, a Target for Cardiovascular–Active Drugs, at 2.5 Å Resolution", *Science*, 243, pp. 1346–1351 (1989).

Y. Tanji et al., "Hepatitis C Virus–Encoded Nonstructural Protein NS4A Has Versatile Functions in Viral Protein Processing", *J. Virology*, 69(3), pp. 1575–1581 (Mar. 1995).

Y. Shimizu et al., "Identification of the Sequence of NS4A Required for Enhanced Cleavage of the NS5A/5B Site by Hepatitis C Virus NS3 Protease", *J. Virology*, 70(1), pp. 127–132 (Jan. 1996).

U. Uhlin et al., "Crystallization and Crystallographic Investigations of Ribonucleotide Reductase Protein R1 From *Escherichia Coli*", *FEBS*, 336(1), pp. 148–152 (1993).

C.S. Wright et al., "Structure of Subtilisin BPN' at 2.5 Å Resolution", *Nature*, 221, pp. 235–242 (1969).

*Primary Examiner*—Karen Cochrane Carlson
*Assistant Examiner*—Anish Gupta
*Attorney, Agent, or Firm*—Fish & Neave; James F. Haley, Jr., Esq.; Lisa A. Dixon

[57] ABSTRACT

The present invention relates to compositions and crystals of a hepatitis C virus protease in complex with its viral cofactor. This invention also relates to methods of using the structure coordinates of hepatitis C virus protease in complex with a synthetic NS4A to solve the structure of similar or homologous proteins or protein complexes.

9 Claims, 61 Drawing Sheets

FIG. 3A-1 tNS3 COORDINATES (Complex A)

| Atom | Atom Type | Resid | # | X | Y | Z | OCC | B |
|---|---|---|---|---|---|---|---|---|
| 1 | N | VAL | 1055 | 94.186 | 42.391 | 51.819 | 1.00 | 32.85 |
| 2 | CA | VAL | 1055 | 92.743 | 42.519 | 51.462 | 1.00 | 30.82 |
| 3 | CB | VAL | 1055 | 92.435 | 41.883 | 50.083 | 1.00 | 30.41 |
| 4 | CG1 | VAL | 1055 | 90.953 | 41.986 | 49.767 | 1.00 | 31.38 |
| 5 | CG2 | VAL | 1055 | 93.232 | 42.576 | 48.999 | 1.00 | 30.52 |
| 6 | C | VAL | 1055 | 91.928 | 41.817 | 52.527 | 1.00 | 30.32 |
| 7 | O | VAL | 1055 | 92.271 | 40.715 | 52.954 | 1.00 | 31.39 |
| 8 | N | GLU | 1056 | 90.869 | 42.481 | 52.975 | 1.00 | 30.38 |
| 9 | CA | GLU | 1056 | 89.985 | 41.933 | 53.994 | 1.00 | 28.82 |
| 10 | CB | GLU | 1056 | 89.909 | 42.877 | 55.191 | 1.00 | 28.56 |
| 11 | CG | GLU | 1056 | 91.249 | 43.090 | 55.856 | 1.00 | 33.65 |
| 12 | CD | GLU | 1056 | 91.183 | 44.066 | 57.007 | 1.00 | 37.88 |
| 13 | OE1 | GLU | 1056 | 91.610 | 43.695 | 58.120 | 1.00 | 40.68 |
| 14 | OE2 | GLU | 1056 | 90.713 | 45.204 | 56.796 | 1.00 | 40.04 |
| 15 | C | GLU | 1056 | 88.590 | 41.675 | 53.442 | 1.00 | 26.54 |
| 16 | O | GLU | 1056 | 88.102 | 42.417 | 52.591 | 1.00 | 26.63 |
| 17 | N | GLY | 1057 | 87.970 | 40.602 | 53.914 | 1.00 | 24.45 |
| 18 | CA | GLY | 1057 | 86.633 | 40.261 | 53.478 | 1.00 | 22.13 |
| 19 | C | GLY | 1057 | 85.614 | 40.570 | 54.553 | 1.00 | 21.95 |
| 20 | O | GLY | 1057 | 85.918 | 40.510 | 55.742 | 1.00 | 23.57 |
| 21 | N | GLU | 1058 | 84.406 | 40.924 | 54.140 | 1.00 | 20.53 |
| 22 | CA | GLU | 1058 | 83.352 | 41.236 | 55.084 | 1.00 | 18.51 |
| 23 | CB | GLU | 1058 | 82.408 | 42.295 | 54.514 | 1.00 | 18.38 |
| 24 | CG | GLU | 1058 | 83.060 | 43.597 | 54.096 | 1.00 | 18.99 |
| 25 | CD | GLU | 1058 | 83.531 | 43.593 | 52.650 | 1.00 | 23.27 |
| 26 | OE1 | GLU | 1058 | 83.746 | 42.504 | 52.083 | 1.00 | 24.96 |
| 27 | OE2 | GLU | 1058 | 83.701 | 44.686 | 52.067 | 1.00 | 26.97 |
| 28 | C | GLU | 1058 | 82.580 | 39.954 | 55.338 | 1.00 | 19.61 |
| 29 | O | GLU | 1058 | 81.988 | 39.770 | 56.399 | 1.00 | 21.48 |
| 30 | N | VAL | 1059 | 82.604 | 39.062 | 54.354 | 1.00 | 18.78 |
| 31 | CA | VAL | 1059 | 81.899 | 37.789 | 54.428 | 1.00 | 18.22 |
| 32 | CB | VAL | 1059 | 80.990 | 37.583 | 53.170 | 1.00 | 16.33 |
| 33 | CG1 | VAL | 1059 | 80.286 | 36.249 | 53.225 | 1.00 | 13.76 |
| 34 | CG2 | VAL | 1059 | 79.977 | 38.702 | 53.048 | 1.00 | 12.68 |
| 35 | C | VAL | 1059 | 82.903 | 36.644 | 54.491 | 1.00 | 20.89 |
| 36 | O | VAL | 1059 | 83.826 | 36.571 | 53.676 | 1.00 | 20.81 |
| 37 | N | GLN | 1060 | 82.737 | 35.758 | 55.465 | 1.00 | 21.48 |
| 38 | CA | GLN | 1060 | 83.629 | 34.620 | 55.582 | 1.00 | 22.32 |
| 39 | CB | GLN | 1060 | 84.405 | 34.633 | 56.908 | 1.00 | 23.40 |
| 40 | CG | GLN | 1060 | 83.662 | 35.176 | 58.104 | 1.00 | 24.97 |
| 41 | CD | GLN | 1060 | 83.707 | 36.692 | 58.201 | 1.00 | 25.79 |
| 42 | OE1 | GLN | 1060 | 84.519 | 37.351 | 57.553 | 1.00 | 27.09 |
| 43 | NE2 | GLN | 1060 | 82.842 | 37.252 | 59.031 | 1.00 | 25.24 |
| 44 | C | GLN | 1060 | 82.863 | 33.325 | 55.410 | 1.00 | 23.40 |
| 45 | O | GLN | 1060 | 81.735 | 33.202 | 55.880 | 1.00 | 25.77 |
| 46 | N | ILE | 1061 | 83.457 | 32.399 | 54.663 | 1.00 | 23.80 |

FIG. 3A-2

|  | Atom | | | | | | | |
|---|---|---|---|---|---|---|---|---|
| Atom | Type | Resid | # | X | Y | Z | OCC | B |
| 47 | CA | ILE | 1061 | 82.882 | 31.086 | 54.390 | 1.00 | 23.08 |
| 48 | CB | ILE | 1061 | 83.399 | 30.530 | 53.052 | 1.00 | 23.13 |
| 49 | CG2 | ILE | 1061 | 82.659 | 29.258 | 52.698 | 1.00 | 20.59 |
| 50 | CG1 | ILE | 1061 | 83.219 | 31.584 | 51.951 | 1.00 | 23.17 |
| 51 | CD1 | ILE | 1061 | 83.949 | 31.275 | 50.692 | 1.00 | 21.52 |
| 52 | C | ILE | 1061 | 83.335 | 30.173 | 55.517 | 1.00 | 24.42 |
| 53 | O | ILE | 1061 | 84.498 | 29.766 | 55.574 | 1.00 | 26.06 |
| 54 | N | VAL | 1062 | 82.404 | 29.850 | 56.404 | 1.00 | 25.24 |
| 55 | CA | VAL | 1062 | 82.688 | 29.028 | 57.569 | 1.00 | 24.13 |
| 56 | CB | VAL | 1062 | 82.085 | 29.682 | 58.832 | 1.00 | 21.93 |
| 57 | CG1 | VAL | 1062 | 82.568 | 31.124 | 58.951 | 1.00 | 20.61 |
| 58 | CG2 | VAL | 1062 | 80.578 | 29.645 | 58.778 | 1.00 | 18.03 |
| 59 | C | VAL | 1062 | 82.201 | 27.587 | 57.443 | 1.00 | 26.46 |
| 60 | O | VAL | 1062 | 81.391 | 27.261 | 56.573 | 1.00 | 26.50 |
| 61 | N | SER | 1063 | 82.685 | 26.730 | 58.332 | 1.00 | 28.27 |
| 62 | CA | SER | 1063 | 82.312 | 25.326 | 58.316 | 1.00 | 29.40 |
| 63 | CB | SER | 1063 | 83.246 | 24.539 | 57.389 | 1.00 | 29.43 |
| 64 | OG | SER | 1063 | 83.164 | 25.013 | 56.054 | 1.00 | 33.51 |
| 65 | C | SER | 1063 | 82.339 | 24.684 | 59.696 | 1.00 | 31.16 |
| 66 | O | SER | 1063 | 83.000 | 25.167 | 60.623 | 1.00 | 30.35 |
| 67 | N | THR | 1064 | 81.593 | 23.593 | 59.811 | 1.00 | 33.89 |
| 68 | CA | THR | 1064 | 81.497 | 22.790 | 61.023 | 1.00 | 33.81 |
| 69 | CB | THR | 1064 | 80.091 | 22.855 | 61.651 | 1.00 | 31.40 |
| 70 | OG1 | THR | 1064 | 79.099 | 22.536 | 60.664 | 1.00 | 33.92 |
| 71 | CG2 | THR | 1064 | 79.825 | 24.230 | 62.216 | 1.00 | 29.94 |
| 72 | C | THR | 1064 | 81.769 | 21.383 | 60.511 | 1.00 | 35.92 |
| 73 | O | THR | 1064 | 81.951 | 21.200 | 59.305 | 1.00 | 36.71 |
| 74 | N | ALA | 1065 | 81.800 | 20.395 | 61.396 | 1.00 | 38.38 |
| 75 | CA | ALA | 1065 | 82.060 | 19.022 | 60.975 | 1.00 | 40.41 |
| 76 | CB | ALA | 1065 | 82.104 | 18.114 | 62.181 | 1.00 | 41.57 |
| 77 | C | ALA | 1065 | 81.044 | 18.490 | 59.966 | 1.00 | 41.85 |
| 78 | O | ALA | 1065 | 81.357 | 17.623 | 59.151 | 1.00 | 41.76 |
| 79 | N | THR | 1066 | 79.827 | 19.016 | 60.025 | 1.00 | 43.16 |
| 80 | CA | THR | 1066 | 78.758 | 18.559 | 59.148 | 1.00 | 45.82 |
| 81 | CB | THR | 1066 | 77.582 | 18.022 | 60.003 | 1.00 | 48.55 |
| 82 | OG1 | THR | 1066 | 77.141 | 19.047 | 60.914 | 1.00 | 51.57 |
| 83 | CG2 | THR | 1066 | 78.009 | 16.795 | 60.791 | 1.00 | 51.00 |
| 84 | C | THR | 1066 | 78.147 | 19.613 | 58.224 | 1.00 | 46.64 |
| 85 | O | THR | 1066 | 77.374 | 19.265 | 57.323 | 1.00 | 48.12 |
| 86 | N | GLN | 1067 | 78.466 | 20.887 | 58.431 | 1.00 | 45.58 |
| 87 | CA | GLN | 1067 | 77.829 | 21.923 | 57.636 | 1.00 | 43.33 |
| 88 | CB | GLN | 1067 | 76.635 | 22.429 | 58.438 | 1.00 | 44.54 |
| 89 | CG | GLN | 1067 | 75.606 | 23.244 | 57.682 | 1.00 | 48.92 |
| 90 | CD | GLN | 1067 | 74.377 | 23.595 | 58.535 | 1.00 | 51.71 |
| 91 | OE1 | GLN | 1067 | 73.519 | 24.380 | 58.113 | 1.00 | 53.17 |
| 92 | NE2 | GLN | 1067 | 74.297 | 23.023 | 59.738 | 1.00 | 49.37 |
| 93 | C | GLN | 1067 | 78.720 | 23.091 | 57.269 | 1.00 | 40.47 |
| 94 | O | GLN | 1067 | 79.567 | 23.498 | 58.053 | 1.00 | 41.29 |
| 95 | N | THR | 1068 | 78.523 | 23.612 | 56.063 | 1.00 | 37.11 |

FIG. 3A-3

| Atom | Atom Type | Resid | # | X | Y | Z | OCC | B |
|---|---|---|---|---|---|---|---|---|
| 96 | CA | THR | 1068 | 79.261 | 24.767 | 55.574 | 1.00 | 30.70 |
| 97 | CB | THR | 1068 | 80.113 | 24.436 | 54.331 | 1.00 | 29.76 |
| 98 | OG1 | THR | 1068 | 81.008 | 25.521 | 54.062 | 1.00 | 30.04 |
| 99 | CG2 | THR | 1068 | 79.241 | 24.184 | 53.113 | 1.00 | 30.99 |
| 100 | C | THR | 1068 | 78.236 | 25.843 | 55.234 | 1.00 | 28.68 |
| 101 | O | THR | 1068 | 77.192 | 25.565 | 54.644 | 1.00 | 27.99 |
| 102 | N | PHE | 1069 | 78.517 | 27.063 | 55.659 | 1.00 | 26.46 |
| 103 | CA | PHE | 1069 | 77.631 | 28.186 | 55.420 | 1.00 | 23.03 |
| 104 | CB | PHE | 1069 | 76.499 | 28.199 | 56.450 | 1.00 | 22.57 |
| 105 | CG | PHE | 1069 | 76.955 | 27.964 | 57.854 | 1.00 | 22.39 |
| 106 | CD1 | PHE | 1069 | 77.011 | 29.014 | 58.759 | 1.00 | 22.57 |
| 107 | CD2 | PHE | 1069 | 77.351 | 26.699 | 58.271 | 1.00 | 22.33 |
| 108 | CE1 | PHE | 1069 | 77.458 | 28.808 | 60.057 | 1.00 | 23.82 |
| 109 | CE2 | PHE | 1069 | 77.800 | 26.485 | 59.566 | 1.00 | 22.79 |
| 110 | CZ | PHE | 1069 | 77.855 | 27.543 | 60.461 | 1.00 | 23.30 |
| 111 | C | PHE | 1069 | 78.456 | 29.472 | 55.447 | 1.00 | 22.55 |
| 112 | O | PHE | 1069 | 79.670 | 29.421 | 55.249 | 1.00 | 21.97 |
| 113 | N | LEU | 1070 | 77.832 | 30.607 | 55.734 | 1.00 | 19.95 |
| 114 | CA | LEU | 1070 | 78.562 | 31.866 | 55.734 | 1.00 | 19.27 |
| 115 | CB | LEU | 1070 | 78.091 | 32.748 | 54.571 | 1.00 | 19.20 |
| 116 | CG | LEU | 1070 | 78.060 | 32.230 | 53.135 | 1.00 | 16.10 |
| 117 | CD1 | LEU | 1070 | 77.451 | 33.307 | 52.257 | 1.00 | 13.03 |
| 118 | CD2 | LEU | 1070 | 79.445 | 31.859 | 52.670 | 1.00 | 15.83 |
| 119 | C | LEU | 1070 | 78.347 | 32.649 | 57.009 | 1.00 | 18.16 |
| 120 | O | LEU | 1070 | 77.443 | 32.345 | 57.781 | 1.00 | 20.67 |
| 121 | N | ALA | 1071 | 79.186 | 33.661 | 57.210 | 1.00 | 16.24 |
| 122 | CA | ALA | 1071 | 79.091 | 34.565 | 58.349 | 1.00 | 17.10 |
| 123 | CB | ALA | 1071 | 80.142 | 34.249 | 59.377 | 1.00 | 19.06 |
| 124 | C | ALA | 1071 | 79.340 | 35.935 | 57.750 | 1.00 | 18.14 |
| 125 | O | ALA | 1071 | 79.958 | 36.030 | 56.693 | 1.00 | 19.55 |
| 126 | N | THR | 1072 | 78.839 | 36.981 | 58.396 | 1.00 | 17.51 |
| 127 | CA | THR | 1072 | 78.999 | 38.345 | 57.909 | 1.00 | 16.67 |
| 128 | CB | THR | 1072 | 77.679 | 38.890 | 57.335 | 1.00 | 14.90 |
| 129 | OG1 | THR | 1072 | 77.249 | 38.048 | 56.269 | 1.00 | 19.26 |
| 130 | CG2 | THR | 1072 | 77.852 | 40.303 | 56.799 | 1.00 | 13.79 |
| 131 | C | THR | 1072 | 79.410 | 39.262 | 59.049 | 1.00 | 19.92 |
| 132 | O | THR | 1072 | 78.785 | 39.264 | 60.112 | 1.00 | 22.53 |
| 133 | N | CYS | 1073 | 80.470 | 40.032 | 58.840 | 1.00 | 20.00 |
| 134 | CA | CYS | 1073 | 80.916 | 40.960 | 59.856 | 1.00 | 19.38 |
| 135 | CB | CYS | 1073 | 82.388 | 41.267 | 59.691 | 1.00 | 17.15 |
| 136 | SG | CYS | 1073 | 83.433 | 39.961 | 60.265 | 1.00 | 21.59 |
| 137 | C | CYS | 1073 | 80.144 | 42.240 | 59.705 | 1.00 | 20.61 |
| 138 | O | CYS | 1073 | 80.125 | 42.821 | 58.623 | 1.00 | 21.53 |
| 139 | N | ILE | 1074 | 79.470 | 42.654 | 60.770 | 1.00 | 23.02 |
| 140 | CA | ILE | 1074 | 78.706 | 43.903 | 60.793 | 1.00 | 24.61 |
| 141 | CB | ILE | 1074 | 77.189 | 43.676 | 60.592 | 1.00 | 24.97 |
| 142 | CG2 | ILE | 1074 | 76.426 | 44.967 | 60.844 | 1.00 | 27.22 |
| 143 | CG1 | ILE | 1074 | 76.904 | 43.174 | 59.178 | 1.00 | 23.86 |
| 144 | CD1 | ILE | 1074 | 75.491 | 42.685 | 58.985 | 1.00 | 25.93 |

FIG. 3A-4

| Atom | Atom Type | Resid | # | X | Y | Z | OCC | B |
|---|---|---|---|---|---|---|---|---|
| 145 | C | ILE | 1074 | 78.943 | 44.491 | 62.176 | 1.00 | 26.19 |
| 146 | O | ILE | 1074 | 78.833 | 43.790 | 63.185 | 1.00 | 28.47 |
| 147 | N | ASN | 1075 | 79.320 | 45.760 | 62.222 | 1.00 | 26.56 |
| 148 | CA | ASN | 1075 | 79.593 | 46.430 | 63.488 | 1.00 | 27.15 |
| 149 | CB | ASN | 1075 | 78.297 | 46.703 | 64.261 | 1.00 | 28.70 |
| 150 | CG | ASN | 1075 | 77.415 | 47.756 | 63.592 | 1.00 | 30.77 |
| 151 | OD1 | ASN | 1075 | 77.829 | 48.418 | 62.639 | 1.00 | 33.91 |
| 152 | ND2 | ASN | 1075 | 76.192 | 47.915 | 64.094 | 1.00 | 30.24 |
| 153 | C | ASN | 1075 | 80.599 | 45.671 | 64.368 | 1.00 | 28.13 |
| 154 | O | ASN | 1075 | 80.388 | 45.504 | 65.569 | 1.00 | 27.91 |
| 155 | N | GLY | 1076 | 81.687 | 45.206 | 63.760 | 1.00 | 28.00 |
| 156 | CA | GLY | 1076 | 82.723 | 44.506 | 64.502 | 1.00 | 27.37 |
| 157 | C | GLY | 1076 | 82.411 | 43.101 | 64.970 | 1.00 | 29.01 |
| 158 | O | GLY | 1076 | 83.264 | 42.433 | 65.567 | 1.00 | 28.27 |
| 159 | N | VAL | 1077 | 81.205 | 42.631 | 64.678 | 1.00 | 29.05 |
| 160 | CA | VAL | 1077 | 80.801 | 41.298 | 65.084 | 1.00 | 27.37 |
| 161 | CB | VAL | 1077 | 79.453 | 41.339 | 65.821 | 1.00 | 26.61 |
| 162 | CG1 | VAL | 1077 | 79.062 | 39.956 | 66.292 | 1.00 | 27.45 |
| 163 | CG2 | VAL | 1077 | 79.536 | 42.281 | 66.995 | 1.00 | 27.61 |
| 164 | C | VAL | 1077 | 80.688 | 40.392 | 63.864 | 1.00 | 27.94 |
| 165 | O | VAL | 1077 | 80.387 | 40.852 | 62.759 | 1.00 | 29.66 |
| 166 | N | CYS | 1078 | 80.989 | 39.114 | 64.062 | 1.00 | 26.17 |
| 167 | CA | CYS | 1078 | 80.910 | 38.114 | 63.011 | 1.00 | 23.77 |
| 168 | CB | CYS | 1078 | 82.097 | 37.158 | 63.101 | 1.00 | 23.73 |
| 169 | SG | CYS | 1078 | 82.221 | 35.981 | 61.746 | 1.00 | 23.84 |
| 170 | C | CYS | 1078 | 79.610 | 37.378 | 63.286 | 1.00 | 23.02 |
| 171 | O | CYS | 1078 | 79.533 | 36.557 | 64.200 | 1.00 | 24.11 |
| 172 | N | TRP | 1079 | 78.576 | 37.726 | 62.534 | 1.00 | 21.24 |
| 173 | CA | TRP | 1079 | 77.260 | 37.133 | 62.698 | 1.00 | 19.55 |
| 174 | CB | TRP | 1079 | 76.187 | 38.178 | 62.406 | 1.00 | 19.32 |
| 175 | CG | TRP | 1079 | 76.340 | 39.431 | 63.178 | 1.00 | 21.82 |
| 176 | CD2 | TRP | 1079 | 75.766 | 39.721 | 64.460 | 1.00 | 23.32 |
| 177 | CE2 | TRP | 1079 | 76.112 | 41.055 | 64.781 | 1.00 | 24.08 |
| 178 | CE3 | TRP | 1079 | 74.989 | 38.986 | 65.364 | 1.00 | 21.58 |
| 179 | CD1 | TRP | 1079 | 77.003 | 40.560 | 62.788 | 1.00 | 22.05 |
| 180 | NE1 | TRP | 1079 | 76.868 | 41.542 | 63.745 | 1.00 | 23.78 |
| 181 | CZ2 | TRP | 1079 | 75.703 | 41.670 | 65.967 | 1.00 | 22.89 |
| 182 | CZ3 | TRP | 1079 | 74.582 | 39.596 | 66.540 | 1.00 | 22.78 |
| 183 | CH2 | TRP | 1079 | 74.940 | 40.929 | 66.831 | 1.00 | 23.44 |
| 184 | C | TRP | 1079 | 77.028 | 35.976 | 61.763 | 1.00 | 18.27 |
| 185 | O | TRP | 1079 | 77.576 | 35.939 | 60.661 | 1.00 | 20.23 |
| 186 | N | THR | 1080 | 76.196 | 35.041 | 62.200 | 1.00 | 17.65 |
| 187 | CA | THR | 1080 | 75.813 | 33.895 | 61.391 | 1.00 | 18.57 |
| 188 | CB | THR | 1080 | 76.917 | 32.826 | 61.319 | 1.00 | 18.31 |
| 189 | OG1 | THR | 1080 | 76.535 | 31.806 | 60.384 | 1.00 | 15.58 |
| 190 | CG2 | THR | 1080 | 77.164 | 32.212 | 62.666 | 1.00 | 16.32 |
| 191 | C | THR | 1080 | 74.506 | 33.321 | 61.930 | 1.00 | 19.72 |
| 192 | O | THR | 1080 | 73.939 | 33.844 | 62.894 | 1.00 | 20.69 |
| 193 | N | VAL | 1081 | 74.023 | 32.258 | 61.304 | 1.00 | 22.55 |

FIG. 3A-5

| Atom | Atom Type | Resid | # | X | Y | Z | OCC | B |
|---|---|---|---|---|---|---|---|---|
| 194 | CA | VAL | 1081 | 72.767 | 31.633 | 61.700 | 1.00 | 23.39 |
| 195 | CB | VAL | 1081 | 72.019 | 31.058 | 60.473 | 1.00 | 21.81 |
| 196 | CG1 | VAL | 1081 | 71.432 | 32.176 | 59.648 | 1.00 | 19.45 |
| 197 | CG2 | VAL | 1081 | 72.972 | 30.227 | 59.617 | 1.00 | 22.36 |
| 198 | C | VAL | 1081 | 72.942 | 30.524 | 62.729 | 1.00 | 25.42 |
| 199 | O | VAL | 1081 | 73.693 | 29.565 | 62.510 | 1.00 | 27.35 |
| 200 | N | TYR | 1082 | 72.191 | 30.632 | 63.823 | 1.00 | 27.30 |
| 201 | CA | TYR | 1082 | 72.211 | 29.644 | 64.902 | 1.00 | 28.71 |
| 202 | CB | TYR | 1082 | 71.139 | 29.964 | 65.946 | 1.00 | 29.28 |
| 203 | CG | TYR | 1082 | 71.171 | 29.063 | 67.161 | 1.00 | 29.31 |
| 204 | CD1 | TYR | 1082 | 70.439 | 27.883 | 67.191 | 1.00 | 32.22 |
| 205 | CE1 | TYR | 1082 | 70.458 | 27.048 | 68.308 | 1.00 | 35.00 |
| 206 | CD2 | TYR | 1082 | 71.928 | 29.395 | 68.281 | 1.00 | 29.57 |
| 207 | CE2 | TYR | 1082 | 71.957 | 28.570 | 69.406 | 1.00 | 32.16 |
| 208 | CZ | TYR | 1082 | 71.216 | 27.395 | 69.415 | 1.00 | 34.16 |
| 209 | OH | TYR | 1082 | 71.214 | 26.568 | 70.524 | 1.00 | 34.78 |
| 210 | C | TYR | 1082 | 72.005 | 28.218 | 64.398 | 1.00 | 28.97 |
| 211 | O | TYR | 1082 | 72.591 | 27.286 | 64.945 | 1.00 | 31.64 |
| 212 | N | HIS | 1083 | 71.200 | 28.046 | 63.350 | 1.00 | 28.60 |
| 213 | CA | HIS | 1083 | 70.943 | 26.717 | 62.800 | 1.00 | 29.08 |
| 214 | CB | HIS | 1083 | 69.730 | 26.725 | 61.858 | 1.00 | 28.98 |
| 215 | CG | HIS | 1083 | 69.984 | 27.333 | 60.508 | 1.00 | 27.71 |
| 216 | CD2 | HIS | 1083 | 70.696 | 26.886 | 59.443 | 1.00 | 27.80 |
| 217 | ND1 | HIS | 1083 | 69.392 | 28.509 | 60.106 | 1.00 | 26.55 |
| 218 | CE1 | HIS | 1083 | 69.724 | 28.766 | 58.852 | 1.00 | 28.23 |
| 219 | NE2 | HIS | 1083 | 70.514 | 27.795 | 58.427 | 1.00 | 28.18 |
| 220 | C | HIS | 1083 | 72.153 | 26.103 | 62.102 | 1.00 | 31.61 |
| 221 | O | HIS | 1083 | 72.056 | 25.016 | 61.516 | 1.00 | 32.83 |
| 222 | N | GLY | 1084 | 73.270 | 26.826 | 62.110 | 1.00 | 31.35 |
| 223 | CA | GLY | 1084 | 74.479 | 26.329 | 61.486 | 1.00 | 30.49 |
| 224 | C | GLY | 1084 | 75.597 | 26.297 | 62.501 | 1.00 | 30.79 |
| 225 | O | GLY | 1084 | 76.345 | 25.322 | 62.586 | 1.00 | 31.01 |
| 226 | N | ALA | 1085 | 75.710 | 27.364 | 63.281 | 1.00 | 29.67 |
| 227 | CA | ALA | 1085 | 76.756 | 27.463 | 64.291 | 1.00 | 29.18 |
| 228 | CB | ALA | 1085 | 77.102 | 28.919 | 64.538 | 1.00 | 27.13 |
| 229 | C | ALA | 1085 | 76.385 | 26.797 | 65.608 | 1.00 | 30.86 |
| 230 | O | ALA | 1085 | 77.229 | 26.191 | 66.266 | 1.00 | 32.83 |
| 231 | N | GLY | 1086 | 75.120 | 26.912 | 65.996 | 1.00 | 31.95 |
| 232 | CA | GLY | 1086 | 74.691 | 26.347 | 67.259 | 1.00 | 30.00 |
| 233 | C | GLY | 1086 | 75.280 | 27.240 | 68.329 | 1.00 | 30.52 |
| 234 | O | GLY | 1086 | 75.093 | 28.456 | 68.288 | 1.00 | 31.56 |
| 235 | N | THR | 1087 | 76.004 | 26.659 | 69.277 | 1.00 | 29.74 |
| 236 | CA | THR | 1087 | 76.632 | 27.445 | 70.334 | 1.00 | 29.99 |
| 237 | CB | THR | 1087 | 76.202 | 26.964 | 71.722 | 1.00 | 31.53 |
| 238 | OG1 | THR | 1087 | 76.282 | 25.531 | 71.779 | 1.00 | 33.33 |
| 239 | CG2 | THR | 1087 | 74.792 | 27.428 | 72.043 | 1.00 | 32.33 |
| 240 | C | THR | 1087 | 78.138 | 27.277 | 70.235 | 1.00 | 29.06 |
| 241 | O | THR | 1087 | 78.863 | 27.526 | 71.195 | 1.00 | 29.33 |
| 242 | N | ARG | 1088 | 78.602 | 26.848 | 69.068 | 1.00 | 27.32 |

FIG. 3A-6

| Atom | Atom Type | Resid | # | X | Y | Z | OCC | B |
|---|---|---|---|---|---|---|---|---|
| 243 | CA | ARG | 1088 | 80.013 | 26.607 | 68.849 | 1.00 | 25.61 |
| 244 | CB | ARG | 1088 | 80.232 | 25.970 | 67.484 | 1.00 | 24.43 |
| 245 | CG | ARG | 1088 | 79.894 | 24.510 | 67.450 | 1.00 | 24.44 |
| 246 | CD | ARG | 1088 | 79.804 | 24.007 | 66.034 | 1.00 | 26.01 |
| 247 | NE | ARG | 1088 | 78.457 | 23.542 | 65.721 | 1.00 | 25.14 |
| 248 | CZ | ARG | 1088 | 78.181 | 22.324 | 65.274 | 1.00 | 27.41 |
| 249 | NH1 | ARG | 1088 | 79.162 | 21.449 | 65.099 | 1.00 | 29.46 |
| 250 | NH2 | ARG | 1088 | 76.937 | 21.999 | 64.942 | 1.00 | 27.99 |
| 251 | C | ARG | 1088 | 80.880 | 27.837 | 68.974 | 1.00 | 26.13 |
| 252 | O | ARG | 1088 | 80.407 | 28.963 | 68.843 | 1.00 | 27.98 |
| 253 | N | THR | 1089 | 82.145 | 27.598 | 69.294 | 1.00 | 25.72 |
| 254 | CA | THR | 1089 | 83.135 | 28.648 | 69.412 | 1.00 | 24.74 |
| 255 | CB | THR | 1089 | 84.295 | 28.219 | 70.320 | 1.00 | 21.05 |
| 256 | OG1 | THR | 1089 | 84.682 | 26.880 | 69.991 | 1.00 | 21.01 |
| 257 | CG2 | THR | 1089 | 83.908 | 28.296 | 71.765 | 1.00 | 21.52 |
| 258 | C | THR | 1089 | 83.699 | 28.785 | 68.012 | 1.00 | 25.12 |
| 259 | O | THR | 1089 | 83.616 | 27.844 | 67.218 | 1.00 | 27.12 |
| 260 | N | ILE | 1090 | 84.252 | 29.944 | 67.694 | 1.00 | 23.10 |
| 261 | CA | ILE | 1090 | 84.854 | 30.135 | 66.392 | 1.00 | 22.50 |
| 262 | CB | ILE | 1090 | 84.540 | 31.546 | 65.840 | 1.00 | 21.33 |
| 263 | CG2 | ILE | 1090 | 85.167 | 32.617 | 66.699 | 1.00 | 20.09 |
| 264 | CG1 | ILE | 1090 | 84.962 | 31.653 | 64.378 | 1.00 | 20.03 |
| 265 | CD1 | ILE | 1090 | 84.429 | 32.877 | 63.701 | 1.00 | 19.81 |
| 266 | C | ILE | 1090 | 86.358 | 29.896 | 66.581 | 1.00 | 24.31 |
| 267 | O | ILE | 1090 | 86.924 | 30.289 | 67.611 | 1.00 | 25.80 |
| 268 | N | ALA | 1091 | 86.981 | 29.177 | 65.649 | 1.00 | 23.50 |
| 269 | CA | ALA | 1091 | 88.412 | 28.883 | 65.728 | 1.00 | 23.75 |
| 270 | CB | ALA | 1091 | 88.797 | 27.871 | 64.670 | 1.00 | 22.92 |
| 271 | C | ALA | 1091 | 89.267 | 30.147 | 65.589 | 1.00 | 25.79 |
| 272 | O | ALA | 1091 | 88.962 | 31.039 | 64.789 | 1.00 | 27.65 |
| 273 | N | SER | 1092 | 90.354 | 30.201 | 66.349 | 1.00 | 25.22 |
| 274 | CA | SER | 1092 | 91.271 | 31.335 | 66.345 | 1.00 | 24.64 |
| 275 | CB | SER | 1092 | 90.898 | 32.264 | 67.501 | 1.00 | 24.34 |
| 276 | OG | SER | 1092 | 91.981 | 33.043 | 67.962 | 1.00 | 27.32 |
| 277 | C | SER | 1092 | 92.686 | 30.778 | 66.518 | 1.00 | 26.18 |
| 278 | O | SER | 1092 | 92.859 | 29.722 | 67.129 | 1.00 | 28.18 |
| 279 | N | PRO | 1093 | 93.712 | 31.449 | 65.953 | 1.00 | 26.97 |
| 280 | CD | PRO | 1093 | 93.667 | 32.638 | 65.084 | 1.00 | 27.37 |
| 281 | CA | PRO | 1093 | 95.094 | 30.955 | 66.092 | 1.00 | 27.58 |
| 282 | CB | PRO | 1093 | 95.888 | 31.857 | 65.133 | 1.00 | 26.90 |
| 283 | CG | PRO | 1093 | 95.105 | 33.123 | 65.128 | 1.00 | 28.05 |
| 284 | C | PRO | 1093 | 95.618 | 31.011 | 67.533 | 1.00 | 27.01 |
| 285 | O | PRO | 1093 | 96.778 | 30.729 | 67.803 | 1.00 | 25.78 |
| 286 | N | LYS | 1094 | 94.742 | 31.398 | 68.447 | 1.00 | 28.06 |
| 287 | CA | LYS | 1094 | 95.060 | 31.469 | 69.858 | 1.00 | 29.03 |
| 288 | CB | LYS | 1094 | 94.935 | 32.901 | 70.355 | 1.00 | 27.19 |
| 289 | CG | LYS | 1094 | 96.041 | 33.832 | 69.933 | 1.00 | 30.62 |
| 290 | CD | LYS | 1094 | 95.763 | 35.182 | 70.569 | 1.00 | 34.13 |
| 291 | CE | LYS | 1094 | 96.891 | 36.178 | 70.407 | 1.00 | 36.40 |

FIG. 3A-7

| Atom | Atom Type | Resid | # | X | Y | Z | OCC | B |
|---|---|---|---|---|---|---|---|---|
| 292 | NZ | LYS | 1094 | 96.526 | 37.422 | 71.149 | 1.00 | 40.35 |
| 293 | C | LYS | 1094 | 94.058 | 30.599 | 70.617 | 1.00 | 29.44 |
| 294 | O | LYS | 1094 | 93.960 | 30.680 | 71.842 | 1.00 | 30.88 |
| 295 | N | GLY | 1095 | 93.298 | 29.787 | 69.889 | 1.00 | 30.20 |
| 296 | CA | GLY | 1095 | 92.310 | 28.930 | 70.523 | 1.00 | 30.19 |
| 297 | C | GLY | 1095 | 90.878 | 29.342 | 70.217 | 1.00 | 29.06 |
| 298 | O | GLY | 1095 | 90.654 | 30.374 | 69.580 | 1.00 | 28.17 |
| 299 | N | PRO | 1096 | 89.882 | 28.553 | 70.660 | 1.00 | 28.19 |
| 300 | CD | PRO | 1096 | 90.042 | 27.313 | 71.439 | 1.00 | 26.15 |
| 301 | CA | PRO | 1096 | 88.461 | 28.827 | 70.433 | 1.00 | 27.36 |
| 302 | CB | PRO | 1096 | 87.780 | 27.625 | 71.083 | 1.00 | 27.13 |
| 303 | CG | PRO | 1096 | 88.735 | 27.236 | 72.166 | 1.00 | 24.95 |
| 304 | C | PRO | 1096 | 87.977 | 30.124 | 71.047 | 1.00 | 26.27 |
| 305 | O | PRO | 1096 | 88.301 | 30.430 | 72.194 | 1.00 | 27.96 |
| 306 | N | VAL | 1097 | 87.173 | 30.862 | 70.294 | 1.00 | 24.47 |
| 307 | CA | VAL | 1097 | 86.627 | 32.130 | 70.755 | 1.00 | 24.49 |
| 308 | CB | VAL | 1097 | 86.875 | 33.243 | 69.719 | 1.00 | 22.40 |
| 309 | CG1 | VAL | 1097 | 86.522 | 34.605 | 70.300 | 1.00 | 20.17 |
| 310 | CG2 | VAL | 1097 | 88.314 | 33.214 | 69.269 | 1.00 | 20.81 |
| 311 | C | VAL | 1097 | 85.131 | 31.928 | 70.937 | 1.00 | 25.90 |
| 312 | O | VAL | 1097 | 84.464 | 31.381 | 70.065 | 1.00 | 27.10 |
| 313 | N | ILE | 1098 | 84.598 | 32.365 | 72.066 | 1.00 | 27.33 |
| 314 | CA | ILE | 1098 | 83.182 | 32.179 | 72.326 | 1.00 | 28.53 |
| 315 | CB | ILE | 1098 | 82.905 | 31.988 | 73.815 | 1.00 | 28.58 |
| 316 | CG2 | ILE | 1098 | 83.811 | 30.911 | 74.360 | 1.00 | 27.94 |
| 317 | CG1 | ILE | 1098 | 83.120 | 33.299 | 74.568 | 1.00 | 30.72 |
| 318 | CD1 | ILE | 1098 | 82.509 | 33.302 | 75.955 | 1.00 | 34.23 |
| 319 | C | ILE | 1098 | 82.278 | 33.277 | 71.785 | 1.00 | 29.52 |
| 320 | O | ILE | 1098 | 82.671 | 34.441 | 71.676 | 1.00 | 29.80 |
| 321 | N | GLN | 1099 | 81.050 | 32.886 | 71.471 | 1.00 | 29.40 |
| 322 | CA | GLN | 1099 | 80.064 | 33.804 | 70.933 | 1.00 | 28.62 |
| 323 | CB | GLN | 1099 | 78.738 | 33.078 | 70.717 | 1.00 | 26.55 |
| 324 | CG | GLN | 1099 | 78.850 | 31.815 | 69.887 | 1.00 | 23.75 |
| 325 | CD | GLN | 1099 | 77.506 | 31.260 | 69.498 | 1.00 | 23.24 |
| 326 | OE1 | GLN | 1099 | 76.475 | 31.676 | 70.018 | 1.00 | 24.67 |
| 327 | NE2 | GLN | 1099 | 77.507 | 30.317 | 68.570 | 1.00 | 25.50 |
| 328 | C | GLN | 1099 | 79.842 | 34.976 | 71.865 | 1.00 | 29.81 |
| 329 | O | GLN | 1099 | 79.799 | 34.803 | 73.081 | 1.00 | 30.77 |
| 330 | N | MET | 1100 | 79.802 | 36.175 | 71.293 | 1.00 | 30.86 |
| 331 | CA | MET | 1100 | 79.545 | 37.388 | 72.057 | 1.00 | 31.65 |
| 332 | CB | MET | 1100 | 79.942 | 38.628 | 71.260 | 1.00 | 33.79 |
| 333 | CG | MET | 1100 | 81.407 | 38.978 | 71.236 | 1.00 | 36.58 |
| 334 | SD | MET | 1100 | 81.638 | 40.325 | 70.061 | 1.00 | 40.15 |
| 335 | CE | MET | 1100 | 81.416 | 41.748 | 71.118 | 1.00 | 41.86 |
| 336 | C | MET | 1100 | 78.043 | 37.439 | 72.266 | 1.00 | 32.12 |
| 337 | O | MET | 1100 | 77.565 | 37.967 | 73.266 | 1.00 | 31.59 |
| 338 | N | TYR | 1101 | 77.305 | 36.926 | 71.281 | 1.00 | 32.79 |
| 339 | CA | TYR | 1101 | 75.847 | 36.914 | 71.320 | 1.00 | 32.46 |
| 340 | CB | TYR | 1101 | 75.277 | 38.034 | 70.446 | 1.00 | 31.02 |

FIG. 3A-8

| Atom | Atom Type | Resid | # | X | Y | Z | OCC | B |
|---|---|---|---|---|---|---|---|---|
| 341 | CG | TYR | 1101 | 75.930 | 39.378 | 70.636 | 1.00 | 31.88 |
| 342 | CD1 | TYR | 1101 | 76.961 | 39.795 | 69.792 | 1.00 | 34.30 |
| 343 | CE1 | TYR | 1101 | 77.591 | 41.018 | 69.973 | 1.00 | 33.36 |
| 344 | CD2 | TYR | 1101 | 75.540 | 40.224 | 71.667 | 1.00 | 30.84 |
| 345 | CE2 | TYR | 1101 | 76.162 | 41.446 | 71.857 | 1.00 | 31.48 |
| 346 | CZ | TYR | 1101 | 77.186 | 41.833 | 71.008 | 1.00 | 34.27 |
| 347 | OH | TYR | 1101 | 77.828 | 43.035 | 71.205 | 1.00 | 40.40 |
| 348 | C | TYR | 1101 | 75.300 | 35.593 | 70.802 | 1.00 | 33.51 |
| 349 | O | TYR | 1101 | 75.825 | 35.025 | 69.852 | 1.00 | 32.08 |
| 350 | N | THR | 1102 | 74.247 | 35.113 | 71.449 | 1.00 | 35.21 |
| 351 | CA | THR | 1102 | 73.571 | 33.889 | 71.063 | 1.00 | 36.92 |
| 352 | CB | THR | 1102 | 73.904 | 32.722 | 71.996 | 1.00 | 35.96 |
| 353 | OG1 | THR | 1102 | 75.323 | 32.600 | 72.131 | 1.00 | 38.23 |
| 354 | CG2 | THR | 1102 | 73.356 | 31.429 | 71.426 | 1.00 | 37.30 |
| 355 | C | THR | 1102 | 72.102 | 34.232 | 71.220 | 1.00 | 39.19 |
| 356 | O | THR | 1102 | 71.663 | 34.661 | 72.292 | 1.00 | 39.17 |
| 357 | N | ASN | 1103 | 71.351 | 34.079 | 70.140 | 1.00 | 42.34 |
| 358 | CA | ASN | 1103 | 69.932 | 34.395 | 70.139 | 1.00 | 45.00 |
| 359 | CB | ASN | 1103 | 69.708 | 35.765 | 69.491 | 1.00 | 47.82 |
| 360 | CG | ASN | 1103 | 68.276 | 36.248 | 69.622 | 1.00 | 50.28 |
| 361 | OD1 | ASN | 1103 | 67.325 | 35.471 | 69.499 | 1.00 | 50.88 |
| 362 | ND2 | ASN | 1103 | 68.114 | 37.536 | 69.889 | 1.00 | 51.98 |
| 363 | C | ASN | 1103 | 69.198 | 33.315 | 69.356 | 1.00 | 46.48 |
| 364 | O | ASN | 1103 | 68.956 | 33.457 | 68.157 | 1.00 | 47.79 |
| 365 | N | VAL | 1104 | 68.862 | 32.227 | 70.038 | 1.00 | 47.60 |
| 366 | CA | VAL | 1104 | 68.170 | 31.115 | 69.407 | 1.00 | 48.19 |
| 367 | CB | VAL | 1104 | 67.859 | 30.009 | 70.423 | 1.00 | 48.12 |
| 368 | CG1 | VAL | 1104 | 67.298 | 28.787 | 69.713 | 1.00 | 48.17 |
| 369 | CG2 | VAL | 1104 | 69.120 | 29.646 | 71.196 | 1.00 | 48.35 |
| 370 | C | VAL | 1104 | 66.882 | 31.549 | 68.711 | 1.00 | 49.41 |
| 371 | O | VAL | 1104 | 66.608 | 31.095 | 67.602 | 1.00 | 49.88 |
| 372 | N | ASP | 1105 | 66.115 | 32.437 | 69.343 | 1.00 | 50.15 |
| 373 | CA | ASP | 1105 | 64.856 | 32.921 | 68.770 | 1.00 | 51.06 |
| 374 | CB | ASP | 1105 | 64.190 | 33.946 | 69.697 | 1.00 | 54.26 |
| 375 | CG | ASP | 1105 | 63.123 | 33.329 | 70.588 | 1.00 | 57.62 |
| 376 | OD1 | ASP | 1105 | 62.581 | 34.062 | 71.446 | 1.00 | 59.65 |
| 377 | OD2 | ASP | 1105 | 62.819 | 32.125 | 70.428 | 1.00 | 59.74 |
| 378 | C | ASP | 1105 | 65.023 | 33.537 | 67.394 | 1.00 | 50.07 |
| 379 | O | ASP | 1105 | 64.264 | 33.238 | 66.467 | 1.00 | 52.01 |
| 380 | N | GLN | 1106 | 66.022 | 34.397 | 67.262 | 1.00 | 47.71 |
| 381 | CA | GLN | 1106 | 66.276 | 35.061 | 65.997 | 1.00 | 45.61 |
| 382 | CB | GLN | 1106 | 66.844 | 36.452 | 66.252 | 1.00 | 47.45 |
| 383 | CG | GLN | 1106 | 65.850 | 37.347 | 66.976 | 1.00 | 52.29 |
| 384 | CD | GLN | 1106 | 66.365 | 38.750 | 67.222 | 1.00 | 54.66 |
| 385 | OE1 | GLN | 1106 | 67.565 | 38.964 | 67.405 | 1.00 | 56.39 |
| 386 | NE2 | GLN | 1106 | 65.455 | 39.719 | 67.233 | 1.00 | 54.76 |
| 387 | C | GLN | 1106 | 67.161 | 34.281 | 65.034 | 1.00 | 43.29 |
| 388 | O | GLN | 1106 | 67.370 | 34.715 | 63.904 | 1.00 | 44.19 |
| 389 | N | ASP | 1107 | 67.629 | 33.110 | 65.458 | 1.00 | 40.90 |

FIG. 3A-9

| Atom | Atom Type | Resid | # | X | Y | Z | OCC | B |
|---|---|---|---|---|---|---|---|---|
| 390 | CA | ASP | 1107 | 68.503 | 32.279 | 64.630 | 1.00 | 39.02 |
| 391 | CB | ASP | 1107 | 67.818 | 31.993 | 63.288 | 1.00 | 36.53 |
| 392 | CG | ASP | 1107 | 68.386 | 30.779 | 62.580 | 1.00 | 38.24 |
| 393 | OD1 | ASP | 1107 | 69.035 | 29.937 | 63.233 | 1.00 | 39.97 |
| 394 | OD2 | ASP | 1107 | 68.156 | 30.655 | 61.363 | 1.00 | 39.42 |
| 395 | C | ASP | 1107 | 69.813 | 33.045 | 64.407 | 1.00 | 38.47 |
| 396 | O | ASP | 1107 | 70.500 | 32.848 | 63.406 | 1.00 | 38.85 |
| 397 | N | LEU | 1108 | 70.192 | 33.845 | 65.400 | 1.00 | 37.86 |
| 398 | CA | LEU | 1108 | 71.369 | 34.702 | 65.316 | 1.00 | 37.42 |
| 399 | CB | LEU | 1108 | 70.901 | 36.155 | 65.431 | 1.00 | 35.72 |
| 400 | CG | LEU | 1108 | 71.902 | 37.299 | 65.315 | 1.00 | 33.41 |
| 401 | CD1 | LEU | 1108 | 72.538 | 37.304 | 63.944 | 1.00 | 33.86 |
| 402 | CD2 | LEU | 1108 | 71.163 | 38.594 | 65.539 | 1.00 | 35.77 |
| 403 | C | LEU | 1108 | 72.445 | 34.471 | 66.366 | 1.00 | 37.37 |
| 404 | O | LEU | 1108 | 72.145 | 34.391 | 67.558 | 1.00 | 38.07 |
| 405 | N | VAL | 1109 | 73.698 | 34.388 | 65.924 | 1.00 | 35.09 |
| 406 | CA | VAL | 1109 | 74.830 | 34.228 | 66.838 | 1.00 | 33.17 |
| 407 | CB | VAL | 1109 | 75.296 | 32.744 | 67.025 | 1.00 | 32.32 |
| 408 | CG1 | VAL | 1109 | 74.117 | 31.841 | 67.272 | 1.00 | 32.33 |
| 409 | CG2 | VAL | 1109 | 76.119 | 32.264 | 65.860 | 1.00 | 31.84 |
| 410 | C | VAL | 1109 | 75.972 | 35.070 | 66.296 | 1.00 | 31.38 |
| 411 | O | VAL | 1109 | 76.080 | 35.272 | 65.087 | 1.00 | 32.93 |
| 412 | N | GLY | 1110 | 76.815 | 35.570 | 67.183 | 1.00 | 29.70 |
| 413 | CA | GLY | 1110 | 77.917 | 36.394 | 66.743 | 1.00 | 26.58 |
| 414 | C | GLY | 1110 | 79.129 | 36.273 | 67.627 | 1.00 | 25.55 |
| 415 | O | GLY | 1110 | 79.008 | 36.097 | 68.840 | 1.00 | 25.57 |
| 416 | N | TRP | 1111 | 80.300 | 36.317 | 67.004 | 1.00 | 24.66 |
| 417 | CA | TRP | 1111 | 81.574 | 36.241 | 67.713 | 1.00 | 23.97 |
| 418 | CB | TRP | 1111 | 82.415 | 35.077 | 67.186 | 1.00 | 22.57 |
| 419 | CG | TRP | 1111 | 81.754 | 33.720 | 67.136 | 1.00 | 22.78 |
| 420 | CD2 | TRP | 1111 | 81.163 | 33.091 | 65.987 | 1.00 | 20.85 |
| 421 | CE2 | TRP | 1111 | 80.824 | 31.772 | 66.360 | 1.00 | 19.39 |
| 422 | CE3 | TRP | 1111 | 80.906 | 33.510 | 64.674 | 1.00 | 18.90 |
| 423 | CD1 | TRP | 1111 | 81.725 | 32.785 | 68.135 | 1.00 | 21.78 |
| 424 | NE1 | TRP | 1111 | 81.175 | 31.614 | 67.675 | 1.00 | 21.65 |
| 425 | CZ2 | TRP | 1111 | 80.240 | 30.870 | 65.474 | 1.00 | 19.81 |
| 426 | CZ3 | TRP | 1111 | 80.324 | 32.613 | 63.790 | 1.00 | 18.79 |
| 427 | CH2 | TRP | 1111 | 80.001 | 31.306 | 64.193 | 1.00 | 20.56 |
| 428 | C | TRP | 1111 | 82.298 | 37.532 | 67.355 | 1.00 | 25.16 |
| 429 | O | TRP | 1111 | 81.788 | 38.321 | 66.563 | 1.00 | 25.20 |
| 430 | N | PRO | 1112 | 83.451 | 37.813 | 67.989 | 1.00 | 25.84 |
| 431 | CD | PRO | 1112 | 84.090 | 37.167 | 69.149 | 1.00 | 25.27 |
| 432 | CA | PRO | 1112 | 84.159 | 39.048 | 67.627 | 1.00 | 24.42 |
| 433 | CB | PRO | 1112 | 85.322 | 39.063 | 68.611 | 1.00 | 23.55 |
| 434 | CG | PRO | 1112 | 84.768 | 38.329 | 69.801 | 1.00 | 23.65 |
| 435 | C | PRO | 1112 | 84.666 | 38.826 | 66.194 | 1.00 | 25.76 |
| 436 | O | PRO | 1112 | 84.988 | 37.693 | 65.829 | 1.00 | 27.02 |
| 437 | N | ALA | 1113 | 84.697 | 39.863 | 65.366 | 1.00 | 23.75 |
| 438 | CA | ALA | 1113 | 85.159 | 39.686 | 63.995 | 1.00 | 22.81 |

FIG. 3A-10

| Atom | Atom Type | Resid | # | X | Y | Z | OCC | B |
|---|---|---|---|---|---|---|---|---|
| 439 | CB | ALA | 1113 | 85.051 | 40.980 | 63.239 | 1.00 | 25.86 |
| 440 | C | ALA | 1113 | 86.592 | 39.158 | 63.959 | 1.00 | 23.10 |
| 441 | O | ALA | 1113 | 87.491 | 39.730 | 64.567 | 1.00 | 25.15 |
| 442 | N | PRO | 1114 | 86.826 | 38.071 | 63.212 | 1.00 | 23.57 |
| 443 | CD | PRO | 1114 | 85.827 | 37.384 | 62.375 | 1.00 | 24.85 |
| 444 | CA | PRO | 1114 | 88.135 | 37.433 | 63.074 | 1.00 | 24.09 |
| 445 | CB | PRO | 1114 | 87.790 | 36.144 | 62.340 | 1.00 | 23.05 |
| 446 | CG | PRO | 1114 | 86.691 | 36.587 | 61.430 | 1.00 | 23.55 |
| 447 | C | PRO | 1114 | 89.160 | 38.250 | 62.296 | 1.00 | 27.35 |
| 448 | O | PRO | 1114 | 88.904 | 39.390 | 61.896 | 1.00 | 28.70 |
| 449 | N | GLN | 1115 | 90.324 | 37.654 | 62.078 | 1.00 | 28.98 |
| 450 | CA | GLN | 1115 | 91.380 | 38.312 | 61.331 | 1.00 | 32.07 |
| 451 | CB | GLN | 1115 | 92.747 | 37.751 | 61.726 | 1.00 | 35.02 |
| 452 | CG | GLN | 1115 | 93.188 | 38.161 | 63.107 | 1.00 | 40.55 |
| 453 | CD | GLN | 1115 | 94.606 | 37.721 | 63.422 | 1.00 | 43.24 |
| 454 | OE1 | GLN | 1115 | 94.851 | 36.571 | 63.793 | 1.00 | 41.11 |
| 455 | NE2 | GLN | 1115 | 95.547 | 38.649 | 63.308 | 1.00 | 45.52 |
| 456 | C | GLN | 1115 | 91.168 | 38.171 | 59.821 | 1.00 | 31.93 |
| 457 | O | GLN | 1115 | 90.705 | 37.137 | 59.329 | 1.00 | 30.69 |
| 458 | N | GLY | 1116 | 91.512 | 39.225 | 59.093 | 1.00 | 31.14 |
| 459 | CA | GLY | 1116 | 91.354 | 39.206 | 57.653 | 1.00 | 29.19 |
| 460 | C | GLY | 1116 | 89.973 | 39.686 | 57.271 | 1.00 | 27.79 |
| 461 | O | GLY | 1116 | 89.578 | 39.579 | 56.109 | 1.00 | 28.10 |
| 462 | N | SER | 1117 | 89.249 | 40.247 | 58.237 | 1.00 | 25.03 |
| 463 | CA | SER | 1117 | 87.909 | 40.729 | 57.973 | 1.00 | 24.84 |
| 464 | CB | SER | 1117 | 86.904 | 40.042 | 58.899 | 1.00 | 23.52 |
| 465 | OG | SER | 1117 | 86.986 | 40.560 | 60.214 | 1.00 | 21.42 |
| 466 | C | SER | 1117 | 87.800 | 42.226 | 58.161 | 1.00 | 25.97 |
| 467 | O | SER | 1117 | 88.671 | 42.846 | 58.768 | 1.00 | 27.89 |
| 468 | N | ARG | 1118 | 86.742 | 42.796 | 57.591 | 1.00 | 26.62 |
| 469 | CA | ARG | 1118 | 86.416 | 44.208 | 57.719 | 1.00 | 25.45 |
| 470 | CB | ARG | 1118 | 86.940 | 45.048 | 56.545 | 1.00 | 28.49 |
| 471 | CG | ARG | 1118 | 86.095 | 45.116 | 55.292 | 1.00 | 32.87 |
| 472 | CD | ARG | 1118 | 86.240 | 46.504 | 54.632 | 1.00 | 40.52 |
| 473 | NE | ARG | 1118 | 85.263 | 47.482 | 55.135 | 1.00 | 46.91 |
| 474 | CZ | ARG | 1118 | 84.084 | 47.729 | 54.558 | 1.00 | 48.20 |
| 475 | NH1 | ARG | 1118 | 83.741 | 47.085 | 53.444 | 1.00 | 49.22 |
| 476 | NH2 | ARG | 1118 | 83.217 | 48.567 | 55.114 | 1.00 | 50.55 |
| 477 | C | ARG | 1118 | 84.894 | 44.224 | 57.812 | 1.00 | 24.87 |
| 478 | O | ARG | 1118 | 84.224 | 43.400 | 57.192 | 1.00 | 23.66 |
| 479 | N | SER | 1119 | 84.354 | 45.088 | 58.659 | 1.00 | 24.12 |
| 480 | CA | SER | 1119 | 82.917 | 45.142 | 58.848 | 1.00 | 21.38 |
| 481 | CB | SER | 1119 | 82.566 | 45.698 | 60.221 | 1.00 | 19.53 |
| 482 | OG | SER | 1119 | 82.806 | 44.732 | 61.235 | 1.00 | 18.13 |
| 483 | C | SER | 1119 | 82.134 | 45.881 | 57.789 | 1.00 | 22.88 |
| 484 | O | SER | 1119 | 82.661 | 46.738 | 57.076 | 1.00 | 22.56 |
| 485 | N | LEU | 1120 | 80.872 | 45.486 | 57.682 | 1.00 | 23.25 |
| 486 | CA | LEU | 1120 | 79.915 | 46.057 | 56.758 | 1.00 | 24.37 |
| 487 | CB | LEU | 1120 | 78.950 | 44.979 | 56.290 | 1.00 | 23.76 |

FIG. 3A-11

| Atom | Atom Type | Resid | # | X | Y | Z | OCC | B |
|---|---|---|---|---|---|---|---|---|
| 488 | CG | LEU | 1120 | 78.911 | 44.542 | 54.840 | 1.00 | 23.49 |
| 489 | CD1 | LEU | 1120 | 77.753 | 43.571 | 54.701 | 1.00 | 21.66 |
| 490 | CD2 | LEU | 1120 | 78.726 | 45.752 | 53.934 | 1.00 | 22.71 |
| 491 | C | LEU | 1120 | 79.107 | 47.107 | 57.510 | 1.00 | 27.32 |
| 492 | O | LEU | 1120 | 78.891 | 46.994 | 58.725 | 1.00 | 28.09 |
| 493 | N | THR | 1121 | 78.618 | 48.096 | 56.771 | 1.00 | 30.14 |
| 494 | CA | THR | 1121 | 77.821 | 49.176 | 57.334 | 1.00 | 29.30 |
| 495 | CB | THR | 1121 | 78.065 | 50.474 | 56.574 | 1.00 | 29.90 |
| 496 | OG1 | THR | 1121 | 79.457 | 50.575 | 56.236 | 1.00 | 32.57 |
| 497 | CG2 | THR | 1121 | 77.650 | 51.656 | 57.415 | 1.00 | 28.80 |
| 498 | C | THR | 1121 | 76.361 | 48.835 | 57.150 | 1.00 | 30.05 |
| 499 | O | THR | 1121 | 75.955 | 48.396 | 56.075 | 1.00 | 32.34 |
| 500 | N | PRO | 1122 | 75.546 | 49.021 | 58.190 | 1.00 | 29.89 |
| 501 | CD | PRO | 1122 | 75.910 | 49.352 | 59.571 | 1.00 | 29.08 |
| 502 | CA | PRO | 1122 | 74.118 | 48.717 | 58.088 | 1.00 | 29.25 |
| 503 | CB | PRO | 1122 | 73.637 | 48.907 | 59.517 | 1.00 | 28.58 |
| 504 | CG | PRO | 1122 | 74.856 | 48.613 | 60.323 | 1.00 | 30.38 |
| 505 | C | PRO | 1122 | 73.427 | 49.703 | 57.145 | 1.00 | 30.47 |
| 506 | O | PRO | 1122 | 73.874 | 50.839 | 56.986 | 1.00 | 32.91 |
| 507 | N | CYS | 1123 | 72.346 | 49.271 | 56.511 | 1.00 | 30.63 |
| 508 | CA | CYS | 1123 | 71.621 | 50.136 | 55.596 | 1.00 | 30.60 |
| 509 | CB | CYS | 1123 | 70.614 | 49.332 | 54.778 | 1.00 | 29.72 |
| 510 | SG | CYS | 1123 | 69.790 | 50.297 | 53.488 | 1.00 | 25.00 |
| 511 | C | CYS | 1123 | 70.906 | 51.235 | 56.384 | 1.00 | 32.65 |
| 512 | O | CYS | 1123 | 70.541 | 51.047 | 57.546 | 1.00 | 31.99 |
| 513 | N | THR | 1124 | 70.744 | 52.393 | 55.755 | 1.00 | 34.65 |
| 514 | CA | THR | 1124 | 70.082 | 53.533 | 56.377 | 1.00 | 36.02 |
| 515 | CB | THR | 1124 | 71.118 | 54.557 | 56.908 | 1.00 | 36.13 |
| 516 | OG1 | THR | 1124 | 71.877 | 55.082 | 55.810 | 1.00 | 36.33 |
| 517 | CG2 | THR | 1124 | 72.074 | 53.903 | 57.908 | 1.00 | 34.16 |
| 518 | C | THR | 1124 | 69.208 | 54.236 | 55.337 | 1.00 | 37.69 |
| 519 | O | THR | 1124 | 68.718 | 55.341 | 55.576 | 1.00 | 40.17 |
| 520 | N | CYS | 1125 | 69.040 | 53.609 | 54.174 | 1.00 | 37.56 |
| 521 | CA | CYS | 1125 | 68.243 | 54.202 | 53.110 | 1.00 | 35.40 |
| 522 | CB | CYS | 1125 | 69.001 | 54.161 | 51.775 | 1.00 | 36.85 |
| 523 | SG | CYS | 1125 | 69.270 | 52.512 | 51.083 | 1.00 | 37.80 |
| 524 | C | CYS | 1125 | 66.884 | 53.548 | 52.958 | 1.00 | 34.49 |
| 525 | O | CYS | 1125 | 66.079 | 53.974 | 52.139 | 1.00 | 36.12 |
| 526 | N | GLY | 1126 | 66.637 | 52.496 | 53.725 | 1.00 | 34.32 |
| 527 | CA | GLY | 1126 | 65.358 | 51.813 | 53.650 | 1.00 | 33.36 |
| 528 | C | GLY | 1126 | 64.953 | 51.332 | 52.271 | 1.00 | 32.12 |
| 529 | O | GLY | 1126 | 63.764 | 51.212 | 51.976 | 1.00 | 33.53 |
| 530 | N | SER | 1127 | 65.931 | 51.066 | 51.417 | 1.00 | 30.17 |
| 531 | CA | SER | 1127 | 65.636 | 50.584 | 50.082 | 1.00 | 30.11 |
| 532 | CB | SER | 1127 | 66.886 | 50.595 | 49.220 | 1.00 | 30.14 |
| 533 | OG | SER | 1127 | 66.565 | 50.233 | 47.893 | 1.00 | 31.03 |
| 534 | C | SER | 1127 | 65.090 | 49.165 | 50.154 | 1.00 | 31.51 |
| 535 | O | SER | 1127 | 65.455 | 48.392 | 51.042 | 1.00 | 33.06 |
| 536 | N | SER | 1128 | 64.232 | 48.823 | 49.201 | 1.00 | 32.01 |

FIG. 3A-12

| Atom | Atom Type | Resid | # | X | Y | Z | OCC | B |
|---|---|---|---|---|---|---|---|---|
| 537 | CA | SER | 1128 | 63.625 | 47.501 | 49.140 | 1.00 | 32.06 |
| 538 | CB | SER | 1128 | 62.125 | 47.633 | 48.916 | 1.00 | 33.84 |
| 539 | OG | SER | 1128 | 61.868 | 48.596 | 47.908 | 1.00 | 39.40 |
| 540 | C | SER | 1128 | 64.246 | 46.652 | 48.042 | 1.00 | 31.04 |
| 541 | O | SER | 1128 | 63.892 | 45.490 | 47.866 | 1.00 | 30.15 |
| 542 | N | ASP | 1129 | 65.153 | 47.244 | 47.281 | 1.00 | 31.57 |
| 543 | CA | ASP | 1129 | 65.838 | 46.521 | 46.221 | 1.00 | 30.82 |
| 544 | CB | ASP | 1129 | 66.170 | 47.478 | 45.071 | 1.00 | 32.94 |
| 545 | CG | ASP | 1129 | 64.925 | 48.168 | 44.512 | 1.00 | 37.09 |
| 546 | OD1 | ASP | 1129 | 64.087 | 47.488 | 43.876 | 1.00 | 38.85 |
| 547 | OD2 | ASP | 1129 | 64.769 | 49.388 | 44.731 | 1.00 | 40.93 |
| 548 | C | ASP | 1129 | 67.101 | 45.931 | 46.838 | 1.00 | 28.43 |
| 549 | O | ASP | 1129 | 68.110 | 46.617 | 46.966 | 1.00 | 28.53 |
| 550 | N | LEU | 1130 | 67.006 | 44.679 | 47.280 | 1.00 | 28.60 |
| 551 | CA | LEU | 1130 | 68.114 | 43.965 | 47.922 | 1.00 | 27.20 |
| 552 | CB | LEU | 1130 | 67.570 | 43.060 | 49.026 | 1.00 | 25.89 |
| 553 | CG | LEU | 1130 | 66.449 | 43.614 | 49.910 | 1.00 | 27.61 |
| 554 | CD1 | LEU | 1130 | 66.230 | 42.644 | 51.049 | 1.00 | 30.67 |
| 555 | CD2 | LEU | 1130 | 66.781 | 44.991 | 50.455 | 1.00 | 26.86 |
| 556 | C | LEU | 1130 | 68.955 | 43.122 | 46.955 | 1.00 | 27.30 |
| 557 | O | LEU | 1130 | 68.524 | 42.812 | 45.847 | 1.00 | 29.26 |
| 558 | N | TYR | 1131 | 70.155 | 42.740 | 47.386 | 1.00 | 26.38 |
| 559 | CA | TYR | 1131 | 71.060 | 41.939 | 46.572 | 1.00 | 24.28 |
| 560 | CB | TYR | 1131 | 72.118 | 42.830 | 45.922 | 1.00 | 22.21 |
| 561 | CG | TYR | 1131 | 71.528 | 43.904 | 45.044 | 1.00 | 23.22 |
| 562 | CD1 | TYR | 1131 | 71.208 | 45.151 | 45.562 | 1.00 | 23.25 |
| 563 | CE1 | TYR | 1131 | 70.601 | 46.129 | 44.772 | 1.00 | 25.08 |
| 564 | CD2 | TYR | 1131 | 71.234 | 43.654 | 43.707 | 1.00 | 24.48 |
| 565 | CE2 | TYR | 1131 | 70.626 | 44.627 | 42.905 | 1.00 | 24.25 |
| 566 | CZ | TYR | 1131 | 70.311 | 45.860 | 43.447 | 1.00 | 25.18 |
| 567 | OH | TYR | 1131 | 69.697 | 46.824 | 42.673 | 1.00 | 26.26 |
| 568 | C | TYR | 1131 | 71.725 | 40.924 | 47.479 | 1.00 | 24.97 |
| 569 | O | TYR | 1131 | 72.462 | 41.293 | 48.386 | 1.00 | 27.58 |
| 570 | N | LEU | 1132 | 71.431 | 39.649 | 47.259 | 1.00 | 24.30 |
| 571 | CA | LEU | 1132 | 71.984 | 38.569 | 48.067 | 1.00 | 24.74 |
| 572 | CB | LEU | 1132 | 70.964 | 37.438 | 48.186 | 1.00 | 24.61 |
| 573 | CG | LEU | 1132 | 71.334 | 36.245 | 49.064 | 1.00 | 22.52 |
| 574 | CD1 | LEU | 1132 | 70.194 | 36.009 | 50.007 | 1.00 | 27.96 |
| 575 | CD2 | LEU | 1132 | 71.605 | 35.009 | 48.230 | 1.00 | 23.92 |
| 576 | C | LEU | 1132 | 73.276 | 38.023 | 47.489 | 1.00 | 25.14 |
| 577 | O | LEU | 1132 | 73.350 | 37.746 | 46.297 | 1.00 | 27.15 |
| 578 | N | VAL | 1133 | 74.288 | 37.857 | 48.333 | 1.00 | 25.08 |
| 579 | CA | VAL | 1133 | 75.577 | 37.327 | 47.890 | 1.00 | 24.16 |
| 580 | CB | VAL | 1133 | 76.757 | 38.156 | 48.445 | 1.00 | 23.60 |
| 581 | CG1 | VAL | 1133 | 78.076 | 37.629 | 47.872 | 1.00 | 19.70 |
| 582 | CG2 | VAL | 1133 | 76.556 | 39.645 | 48.134 | 1.00 | 18.12 |
| 583 | C | VAL | 1133 | 75.719 | 35.890 | 48.377 | 1.00 | 24.92 |
| 584 | O | VAL | 1133 | 75.573 | 35.620 | 49.572 | 1.00 | 25.15 |
| 585 | N | THR | 1134 | 75.987 | 34.969 | 47.456 | 1.00 | 24.88 |

FIG. 3A-13

| Atom | Atom Type | Resid | # | X | Y | Z | OCC | B |
|---|---|---|---|---|---|---|---|---|
| 586 | CA | THR | 1134 | 76.125 | 33.563 | 47.812 | 1.00 | 25.34 |
| 587 | CB | THR | 1134 | 75.611 | 32.638 | 46.677 | 1.00 | 27.21 |
| 588 | OG1 | THR | 1134 | 76.498 | 32.698 | 45.550 | 1.00 | 26.50 |
| 589 | CG2 | THR | 1134 | 74.204 | 33.054 | 46.236 | 1.00 | 24.71 |
| 590 | C | THR | 1134 | 77.566 | 33.205 | 48.150 | 1.00 | 25.73 |
| 591 | O | THR | 1134 | 78.476 | 34.010 | 47.944 | 1.00 | 26.83 |
| 592 | N | ARG | 1135 | 77.776 | 31.981 | 48.630 | 1.00 | 25.40 |
| 593 | CA | ARG | 1135 | 79.112 | 31.504 | 48.991 | 1.00 | 23.76 |
| 594 | CB | ARG | 1135 | 79.027 | 30.150 | 49.689 | 1.00 | 22.71 |
| 595 | CG | ARG | 1135 | 78.413 | 29.062 | 48.835 | 1.00 | 25.45 |
| 596 | CD | ARG | 1135 | 78.383 | 27.742 | 49.566 | 1.00 | 26.50 |
| 597 | NE | ARG | 1135 | 79.722 | 27.265 | 49.897 | 1.00 | 27.92 |
| 598 | CZ | ARG | 1135 | 80.174 | 27.097 | 51.135 | 1.00 | 27.79 |
| 599 | NH1 | ARG | 1135 | 79.405 | 27.366 | 52.180 | 1.00 | 28.04 |
| 600 | NH2 | ARG | 1135 | 81.404 | 26.652 | 51.327 | 1.00 | 30.59 |
| 601 | C | ARG | 1135 | 80.038 | 31.382 | 47.792 | 1.00 | 24.58 |
| 602 | O | ARG | 1135 | 81.219 | 31.091 | 47.950 | 1.00 | 25.10 |
| 603 | N | HIS | 1136 | 79.496 | 31.546 | 46.589 | 1.00 | 25.35 |
| 604 | CA | HIS | 1136 | 80.303 | 31.451 | 45.378 | 1.00 | 26.27 |
| 605 | CB | HIS | 1136 | 79.618 | 30.551 | 44.348 | 1.00 | 26.38 |
| 606 | CG | HIS | 1136 | 79.283 | 29.194 | 44.872 | 1.00 | 27.82 |
| 607 | CD2 | HIS | 1136 | 78.091 | 28.629 | 45.174 | 1.00 | 28.51 |
| 608 | ND1 | HIS | 1136 | 80.242 | 28.264 | 45.213 | 1.00 | 29.89 |
| 609 | CE1 | HIS | 1136 | 79.657 | 27.188 | 45.710 | 1.00 | 29.44 |
| 610 | NE2 | HIS | 1136 | 78.353 | 27.387 | 45.697 | 1.00 | 31.77 |
| 611 | C | HIS | 1136 | 80.540 | 32.834 | 44.794 | 1.00 | 26.66 |
| 612 | O | HIS | 1136 | 81.064 | 32.966 | 43.686 | 1.00 | 27.04 |
| 613 | N | ALA | 1137 | 80.126 | 33.850 | 45.552 | 1.00 | 26.65 |
| 614 | CA | ALA | 1137 | 80.265 | 35.253 | 45.179 | 1.00 | 25.32 |
| 615 | CB | ALA | 1137 | 81.675 | 35.532 | 44.664 | 1.00 | 26.21 |
| 616 | C | ALA | 1137 | 79.219 | 35.743 | 44.177 | 1.00 | 25.87 |
| 617 | O | ALA | 1137 | 79.280 | 36.890 | 43.724 | 1.00 | 24.80 |
| 618 | N | ASP | 1138 | 78.256 | 34.887 | 43.837 | 1.00 | 24.81 |
| 619 | CA | ASP | 1138 | 77.203 | 35.277 | 42.903 | 1.00 | 23.77 |
| 620 | CB | ASP | 1138 | 76.301 | 34.091 | 42.536 | 1.00 | 26.17 |
| 621 | CG | ASP | 1138 | 77.038 | 32.962 | 41.827 | 1.00 | 27.49 |
| 622 | OD1 | ASP | 1138 | 77.712 | 33.214 | 40.807 | 1.00 | 27.61 |
| 623 | OD2 | ASP | 1138 | 76.891 | 31.801 | 42.268 | 1.00 | 28.37 |
| 624 | C | ASP | 1138 | 76.344 | 36.301 | 43.629 | 1.00 | 22.53 |
| 625 | O | ASP | 1138 | 76.282 | 36.302 | 44.856 | 1.00 | 23.66 |
| 626 | N | VAL | 1139 | 75.699 | 37.180 | 42.881 | 1.00 | 21.63 |
| 627 | CA | VAL | 1139 | 74.828 | 38.178 | 43.477 | 1.00 | 22.35 |
| 628 | CB | VAL | 1139 | 75.287 | 39.627 | 43.161 | 1.00 | 20.65 |
| 629 | CG1 | VAL | 1139 | 74.385 | 40.625 | 43.854 | 1.00 | 17.61 |
| 630 | CG2 | VAL | 1139 | 76.736 | 39.841 | 43.607 | 1.00 | 16.25 |
| 631 | C | VAL | 1139 | 73.438 | 37.908 | 42.915 | 1.00 | 24.89 |
| 632 | O | VAL | 1139 | 73.270 | 37.696 | 41.706 | 1.00 | 27.94 |
| 633 | N | ILE | 1140 | 72.447 | 37.895 | 43.796 | 1.00 | 24.15 |
| 634 | CA | ILE | 1140 | 71.071 | 37.606 | 43.425 | 1.00 | 21.78 |

FIG. 3A-14

| Atom | Atom Type | Resid | # | X | Y | Z | OCC | B |
|---|---|---|---|---|---|---|---|---|
| 635 | CB | ILE | 1140 | 70.588 | 36.338 | 44.156 | 1.00 | 19.13 |
| 636 | CG2 | ILE | 1140 | 69.104 | 36.166 | 43.999 | 1.00 | 19.57 |
| 637 | CG1 | ILE | 1140 | 71.329 | 35.104 | 43.647 | 1.00 | 17.97 |
| 638 | CD1 | ILE | 1140 | 71.069 | 33.877 | 44.498 | 1.00 | 16.36 |
| 639 | C | ILE | 1140 | 70.149 | 38.748 | 43.816 | 1.00 | 22.53 |
| 640 | O | ILE | 1140 | 69.979 | 39.038 | 44.995 | 1.00 | 23.66 |
| 641 | N | PRO | 1141 | 69.546 | 39.422 | 42.832 | 1.00 | 23.25 |
| 642 | CD | PRO | 1141 | 69.768 | 39.320 | 41.383 | 1.00 | 22.90 |
| 643 | CA | PRO | 1141 | 68.638 | 40.530 | 43.144 | 1.00 | 23.97 |
| 644 | CB | PRO | 1141 | 68.328 | 41.111 | 41.770 | 1.00 | 24.50 |
| 645 | CG | PRO | 1141 | 69.549 | 40.730 | 40.952 | 1.00 | 24.13 |
| 646 | C | PRO | 1141 | 67.372 | 40.003 | 43.835 | 1.00 | 26.14 |
| 647 | O | PRO | 1141 | 66.692 | 39.095 | 43.341 | 1.00 | 27.20 |
| 648 | N | VAL | 1142 | 67.085 | 40.556 | 44.999 | 1.00 | 26.19 |
| 649 | CA | VAL | 1142 | 65.936 | 40.161 | 45.788 | 1.00 | 27.02 |
| 650 | CB | VAL | 1142 | 66.406 | 39.499 | 47.096 | 1.00 | 25.62 |
| 651 | CG1 | VAL | 1142 | 65.263 | 39.348 | 48.074 | 1.00 | 24.17 |
| 652 | CG2 | VAL | 1142 | 67.036 | 38.155 | 46.787 | 1.00 | 24.42 |
| 653 | C | VAL | 1142 | 65.136 | 41.422 | 46.087 | 1.00 | 29.57 |
| 654 | O | VAL | 1142 | 65.703 | 42.462 | 46.413 | 1.00 | 30.26 |
| 655 | N | ARG | 1143 | 63.827 | 41.358 | 45.896 | 1.00 | 31.86 |
| 656 | CA | ARG | 1143 | 62.989 | 42.512 | 46.166 | 1.00 | 35.28 |
| 657 | CB | ARG | 1143 | 61.964 | 42.715 | 45.053 | 1.00 | 38.62 |
| 658 | CG | ARG | 1143 | 61.555 | 44.152 | 44.880 | 1.00 | 40.15 |
| 659 | CD | ARG | 1143 | 60.377 | 44.489 | 45.748 | 1.00 | 44.51 |
| 660 | NE | ARG | 1143 | 60.308 | 45.904 | 46.106 | 1.00 | 51.14 |
| 661 | CZ | ARG | 1143 | 60.485 | 46.926 | 45.269 | 1.00 | 55.15 |
| 662 | NH1 | ARG | 1143 | 60.759 | 46.731 | 43.983 | 1.00 | 57.46 |
| 663 | NH2 | ARG | 1143 | 60.355 | 48.166 | 45.723 | 1.00 | 57.00 |
| 664 | C | ARG | 1143 | 62.316 | 42.243 | 47.497 | 1.00 | 36.53 |
| 665 | O | ARG | 1143 | 61.696 | 41.197 | 47.695 | 1.00 | 39.63 |
| 666 | N | ARG | 1144 | 62.474 | 43.171 | 48.425 | 1.00 | 36.31 |
| 667 | CA | ARG | 1144 | 61.917 | 43.010 | 49.750 | 1.00 | 36.40 |
| 668 | CB | ARG | 1144 | 62.448 | 44.090 | 50.673 | 1.00 | 35.36 |
| 669 | CG | ARG | 1144 | 62.311 | 43.749 | 52.125 | 1.00 | 35.23 |
| 670 | CD | ARG | 1144 | 62.817 | 44.882 | 52.953 | 1.00 | 36.19 |
| 671 | NE | ARG | 1144 | 62.992 | 44.497 | 54.346 | 1.00 | 39.02 |
| 672 | CZ | ARG | 1144 | 63.660 | 45.233 | 55.223 | 1.00 | 40.02 |
| 673 | NH1 | ARG | 1144 | 63.786 | 44.834 | 56.481 | 1.00 | 38.46 |
| 674 | NH2 | ARG | 1144 | 64.205 | 46.377 | 54.831 | 1.00 | 42.18 |
| 675 | C | ARG | 1144 | 60.405 | 43.041 | 49.742 | 1.00 | 38.06 |
| 676 | O | ARG | 1144 | 59.784 | 43.800 | 48.995 | 1.00 | 37.65 |
| 677 | N | ARG | 1145 | 59.820 | 42.193 | 50.575 | 1.00 | 40.25 |
| 678 | CA | ARG | 1145 | 58.377 | 42.107 | 50.689 | 1.00 | 41.89 |
| 679 | CB | ARG | 1145 | 57.897 | 40.717 | 50.278 | 1.00 | 40.89 |
| 680 | CG | ARG | 1145 | 58.127 | 40.425 | 48.805 | 1.00 | 40.67 |
| 681 | CD | ARG | 1145 | 57.432 | 41.454 | 47.960 | 1.00 | 40.17 |
| 682 | NE | ARG | 1145 | 57.599 | 41.235 | 46.530 | 1.00 | 41.36 |
| 683 | CZ | ARG | 1145 | 57.295 | 42.146 | 45.612 | 1.00 | 45.08 |

FIG. 3A-15

| Atom | Atom Type | Resid | # | X | Y | Z | OCC | B |
|---|---|---|---|---|---|---|---|---|
| 684 | NH1 | ARG | 1145 | 56.814 | 43.332 | 45.982 | 1.00 | 47.79 |
| 685 | NH2 | ARG | 1145 | 57.465 | 41.878 | 44.324 | 1.00 | 45.53 |
| 686 | C | ARG | 1145 | 57.903 | 42.458 | 52.090 | 1.00 | 42.89 |
| 687 | O | ARG | 1145 | 56.720 | 42.725 | 52.295 | 1.00 | 44.14 |
| 688 | N | GLY | 1146 | 58.832 | 42.493 | 53.043 | 1.00 | 43.96 |
| 689 | CA | GLY | 1146 | 58.483 | 42.832 | 54.412 | 1.00 | 44.02 |
| 690 | C | GLY | 1146 | 59.699 | 42.813 | 55.312 | 1.00 | 43.54 |
| 691 | O | GLY | 1146 | 60.795 | 42.495 | 54.847 | 1.00 | 44.52 |
| 692 | N | ASP | 1147 | 59.499 | 43.110 | 56.595 | 1.00 | 42.52 |
| 693 | CA | ASP | 1147 | 60.570 | 43.134 | 57.596 | 1.00 | 40.57 |
| 694 | CB | ASP | 1147 | 59.987 | 43.005 | 59.013 | 1.00 | 45.28 |
| 695 | CG | ASP | 1147 | 59.051 | 44.151 | 59.382 | 1.00 | 51.16 |
| 696 | OD1 | ASP | 1147 | 58.092 | 43.897 | 60.151 | 1.00 | 53.15 |
| 697 | OD2 | ASP | 1147 | 59.271 | 45.296 | 58.916 | 1.00 | 54.39 |
| 698 | C | ASP | 1147 | 61.665 | 42.080 | 57.424 | 1.00 | 37.05 |
| 699 | O | ASP | 1147 | 62.845 | 42.387 | 57.552 | 1.00 | 37.14 |
| 700 | N | SER | 1148 | 61.283 | 40.840 | 57.150 | 1.00 | 32.32 |
| 701 | CA | SER | 1148 | 62.278 | 39.794 | 56.996 | 1.00 | 30.82 |
| 702 | CB | SER | 1148 | 62.436 | 39.055 | 58.321 | 1.00 | 32.46 |
| 703 | OG | SER | 1148 | 61.246 | 38.376 | 58.667 | 1.00 | 35.71 |
| 704 | C | SER | 1148 | 62.013 | 38.801 | 55.866 | 1.00 | 28.99 |
| 705 | O | SER | 1148 | 62.313 | 37.619 | 56.003 | 1.00 | 26.58 |
| 706 | N | ARG | 1149 | 61.504 | 39.288 | 54.736 | 1.00 | 29.34 |
| 707 | CA | ARG | 1149 | 61.211 | 38.426 | 53.589 | 1.00 | 30.00 |
| 708 | CB | ARG | 1149 | 59.760 | 37.914 | 53.663 | 1.00 | 33.43 |
| 709 | CG | ARG | 1149 | 59.363 | 36.826 | 52.655 | 1.00 | 36.36 |
| 710 | CD | ARG | 1149 | 58.733 | 37.418 | 51.389 | 1.00 | 42.94 |
| 711 | NE | ARG | 1149 | 57.958 | 36.444 | 50.610 | 1.00 | 46.67 |
| 712 | CZ | ARG | 1149 | 57.764 | 36.514 | 49.291 | 1.00 | 46.83 |
| 713 | NH1 | ARG | 1149 | 58.288 | 37.506 | 48.594 | 1.00 | 45.95 |
| 714 | NH2 | ARG | 1149 | 57.021 | 35.603 | 48.668 | 1.00 | 47.58 |
| 715 | C | ARG | 1149 | 61.442 | 39.191 | 52.290 | 1.00 | 28.92 |
| 716 | O | ARG | 1149 | 61.181 | 40.401 | 52.206 | 1.00 | 27.96 |
| 717 | N | GLY | 1150 | 61.921 | 38.471 | 51.282 | 1.00 | 27.08 |
| 718 | CA | GLY | 1150 | 62.190 | 39.065 | 49.986 | 1.00 | 25.77 |
| 719 | C | GLY | 1150 | 61.983 | 38.029 | 48.900 | 1.00 | 25.52 |
| 720 | O | GLY | 1150 | 62.093 | 36.831 | 49.147 | 1.00 | 24.50 |
| 721 | N | SER | 1151 | 61.672 | 38.479 | 47.694 | 1.00 | 25.63 |
| 722 | CA | SER | 1151 | 61.441 | 37.572 | 46.583 | 1.00 | 27.27 |
| 723 | CB | SER | 1151 | 60.076 | 37.859 | 45.960 | 1.00 | 29.08 |
| 724 | OG | SER | 1151 | 59.833 | 39.257 | 45.883 | 1.00 | 29.83 |
| 725 | C | SER | 1151 | 62.528 | 37.718 | 45.533 | 1.00 | 27.69 |
| 726 | O | SER | 1151 | 62.885 | 38.837 | 45.150 | 1.00 | 28.46 |
| 727 | N | LEU | 1152 | 63.093 | 36.592 | 45.109 | 1.00 | 26.82 |
| 728 | CA | LEU | 1152 | 64.129 | 36.609 | 44.089 | 1.00 | 27.90 |
| 729 | CB | LEU | 1152 | 64.658 | 35.202 | 43.828 | 1.00 | 24.63 |
| 730 | CG | LEU | 1152 | 65.784 | 34.643 | 44.686 | 1.00 | 23.94 |
| 731 | CD1 | LEU | 1152 | 65.377 | 34.577 | 46.139 | 1.00 | 22.37 |
| 732 | CD2 | LEU | 1152 | 66.145 | 33.273 | 44.155 | 1.00 | 19.80 |

FIG. 3A-16

| Atom | Atom Type | Resid | # | X | Y | Z | OCC | B |
|---|---|---|---|---|---|---|---|---|
| 733 | C | LEU | 1152 | 63.501 | 37.127 | 42.811 | 1.00 | 29.83 |
| 734 | O | LEU | 1152 | 62.394 | 36.722 | 42.463 | 1.00 | 33.35 |
| 735 | N | LEU | 1153 | 64.199 | 38.009 | 42.107 | 1.00 | 30.33 |
| 736 | CA | LEU | 1153 | 63.676 | 38.538 | 40.858 | 1.00 | 29.78 |
| 737 | CB | LEU | 1153 | 64.521 | 39.716 | 40.379 | 1.00 | 26.59 |
| 738 | CG | LEU | 1153 | 64.020 | 41.065 | 40.896 | 1.00 | 25.76 |
| 739 | CD1 | LEU | 1153 | 63.897 | 41.039 | 42.394 | 1.00 | 24.26 |
| 740 | CD2 | LEU | 1153 | 64.940 | 42.176 | 40.444 | 1.00 | 26.30 |
| 741 | C | LEU | 1153 | 63.643 | 37.433 | 39.808 | 1.00 | 31.23 |
| 742 | O | LEU | 1153 | 62.853 | 37.474 | 38.869 | 1.00 | 33.74 |
| 743 | N | SER | 1154 | 64.503 | 36.440 | 39.987 | 1.00 | 32.78 |
| 744 | CA | SER | 1154 | 64.596 | 35.309 | 39.081 | 1.00 | 34.85 |
| 745 | CB | SER | 1154 | 65.780 | 35.481 | 38.132 | 1.00 | 36.29 |
| 746 | OG | SER | 1154 | 65.855 | 36.805 | 37.636 | 1.00 | 43.91 |
| 747 | C | SER | 1154 | 64.846 | 34.107 | 39.961 | 1.00 | 35.31 |
| 748 | O | SER | 1154 | 65.943 | 33.949 | 40.505 | 1.00 | 37.17 |
| 749 | N | PRO | 1155 | 63.807 | 33.291 | 40.190 | 1.00 | 35.71 |
| 750 | CD | PRO | 1155 | 62.401 | 33.474 | 39.780 | 1.00 | 36.01 |
| 751 | CA | PRO | 1155 | 63.949 | 32.101 | 41.031 | 1.00 | 34.86 |
| 752 | CB | PRO | 1155 | 62.599 | 31.419 | 40.871 | 1.00 | 35.84 |
| 753 | CG | PRO | 1155 | 61.670 | 32.598 | 40.777 | 1.00 | 36.09 |
| 754 | C | PRO | 1155 | 65.101 | 31.245 | 40.540 | 1.00 | 33.69 |
| 755 | O | PRO | 1155 | 65.426 | 31.254 | 39.352 | 1.00 | 33.22 |
| 756 | N | ARG | 1156 | 65.726 | 30.525 | 41.459 | 1.00 | 33.17 |
| 757 | CA | ARG | 1156 | 66.873 | 29.700 | 41.124 | 1.00 | 35.02 |
| 758 | CB | ARG | 1156 | 68.173 | 30.405 | 41.566 | 1.00 | 37.90 |
| 759 | CG | ARG | 1156 | 68.856 | 31.265 | 40.505 | 1.00 | 40.72 |
| 760 | CD | ARG | 1156 | 68.739 | 32.740 | 40.813 | 1.00 | 43.82 |
| 761 | NE | ARG | 1156 | 69.536 | 33.543 | 39.886 | 1.00 | 49.55 |
| 762 | CZ | ARG | 1156 | 69.696 | 34.864 | 39.972 | 1.00 | 51.56 |
| 763 | NH1 | ARG | 1156 | 69.117 | 35.551 | 40.943 | 1.00 | 52.24 |
| 764 | NH2 | ARG | 1156 | 70.452 | 35.502 | 39.089 | 1.00 | 53.76 |
| 765 | C | ARG | 1156 | 66.799 | 28.348 | 41.804 | 1.00 | 34.39 |
| 766 | O | ARG | 1156 | 66.115 | 28.193 | 42.811 | 1.00 | 35.64 |
| 767 | N | PRO | 1157 | 67.501 | 27.344 | 41.258 | 1.00 | 34.78 |
| 768 | CD | PRO | 1157 | 68.361 | 27.376 | 40.063 | 1.00 | 36.56 |
| 769 | CA | PRO | 1157 | 67.495 | 26.008 | 41.859 | 1.00 | 35.76 |
| 770 | CB | PRO | 1157 | 68.577 | 25.277 | 41.066 | 1.00 | 35.08 |
| 771 | CG | PRO | 1157 | 68.488 | 25.916 | 39.721 | 1.00 | 36.87 |
| 772 | C | PRO | 1157 | 67.930 | 26.189 | 43.305 | 1.00 | 36.38 |
| 773 | O | PRO | 1157 | 68.824 | 26.993 | 43.579 | 1.00 | 38.01 |
| 774 | N | ILE | 1158 | 67.317 | 25.456 | 44.226 | 1.00 | 35.10 |
| 775 | CA | ILE | 1158 | 67.675 | 25.599 | 45.629 | 1.00 | 33.87 |
| 776 | CB | ILE | 1158 | 66.917 | 24.586 | 46.526 | 1.00 | 33.81 |
| 777 | CG2 | ILE | 1158 | 67.042 | 23.174 | 45.973 | 1.00 | 34.22 |
| 778 | CG1 | ILE | 1158 | 67.418 | 24.690 | 47.972 | 1.00 | 36.64 |
| 779 | CD1 | ILE | 1158 | 66.985 | 23.541 | 48.876 | 1.00 | 38.94 |
| 780 | C | ILE | 1158 | 69.185 | 25.486 | 45.834 | 1.00 | 32.49 |
| 781 | O | ILE | 1158 | 69.765 | 26.236 | 46.610 | 1.00 | 32.56 |

FIG. 3A-17

| Atom | Atom Type | Resid | # | X | Y | Z | OCC | B |
|---|---|---|---|---|---|---|---|---|
| 782 | N | SER | 1159 | 69.830 | 24.609 | 45.075 | 1.00 | 32.75 |
| 783 | CA | SER | 1159 | 71.271 | 24.418 | 45.203 | 1.00 | 33.76 |
| 784 | CB | SER | 1159 | 71.769 | 23.392 | 44.188 | 1.00 | 33.12 |
| 785 | OG | SER | 1159 | 71.450 | 23.816 | 42.875 | 1.00 | 38.29 |
| 786 | C | SER | 1159 | 72.035 | 25.722 | 45.028 | 1.00 | 32.08 |
| 787 | O | SER | 1159 | 73.003 | 25.971 | 45.737 | 1.00 | 31.63 |
| 788 | N | TYR | 1160 | 71.591 | 26.554 | 44.092 | 1.00 | 29.65 |
| 789 | CA | TYR | 1160 | 72.255 | 27.822 | 43.835 | 1.00 | 27.91 |
| 790 | CB | TYR | 1160 | 71.482 | 28.628 | 42.798 | 1.00 | 23.87 |
| 791 | CG | TYR | 1160 | 72.293 | 29.740 | 42.158 | 1.00 | 22.81 |
| 792 | CD1 | TYR | 1160 | 73.402 | 29.455 | 41.368 | 1.00 | 22.72 |
| 793 | CE1 | TYR | 1160 | 74.132 | 30.476 | 40.755 | 1.00 | 23.32 |
| 794 | CD2 | TYR | 1160 | 71.934 | 31.078 | 42.319 | 1.00 | 23.14 |
| 795 | CE2 | TYR | 1160 | 72.656 | 32.104 | 41.704 | 1.00 | 21.74 |
| 796 | CZ | TYR | 1160 | 73.749 | 31.793 | 40.928 | 1.00 | 22.91 |
| 797 | OH | TYR | 1160 | 74.454 | 32.793 | 40.307 | 1.00 | 24.05 |
| 798 | C | TYR | 1160 | 72.413 | 28.638 | 45.118 | 1.00 | 29.71 |
| 799 | O | TYR | 1160 | 73.381 | 29.400 | 45.258 | 1.00 | 32.87 |
| 800 | N | LEU | 1161 | 71.479 | 28.469 | 46.054 | 1.00 | 27.50 |
| 801 | CA | LEU | 1161 | 71.522 | 29.192 | 47.320 | 1.00 | 26.61 |
| 802 | CB | LEU | 1161 | 70.140 | 29.752 | 47.670 | 1.00 | 26.28 |
| 803 | CG | LEU | 1161 | 69.679 | 31.031 | 46.958 | 1.00 | 28.68 |
| 804 | CD1 | LEU | 1161 | 69.484 | 30.775 | 45.469 | 1.00 | 29.40 |
| 805 | CD2 | LEU | 1161 | 68.392 | 31.543 | 47.585 | 1.00 | 26.34 |
| 806 | C | LEU | 1161 | 72.054 | 28.374 | 48.495 | 1.00 | 26.66 |
| 807 | O | LEU | 1161 | 72.247 | 28.905 | 49.588 | 1.00 | 28.59 |
| 808 | N | ALA | 1162 | 72.297 | 27.089 | 48.275 | 1.00 | 26.43 |
| 809 | CA | ALA | 1162 | 72.790 | 26.213 | 49.330 | 1.00 | 26.08 |
| 810 | CB | ALA | 1162 | 72.854 | 24.773 | 48.833 | 1.00 | 27.54 |
| 811 | C | ALA | 1162 | 74.148 | 26.638 | 49.878 | 1.00 | 26.55 |
| 812 | O | ALA | 1162 | 75.035 | 27.049 | 49.132 | 1.00 | 25.22 |
| 813 | N | GLY | 1163 | 74.294 | 26.505 | 51.193 | 1.00 | 26.94 |
| 814 | CA | GLY | 1163 | 75.526 | 26.857 | 51.869 | 1.00 | 24.56 |
| 815 | C | GLY | 1163 | 75.724 | 28.351 | 52.043 | 1.00 | 25.00 |
| 816 | O | GLY | 1163 | 76.767 | 28.771 | 52.529 | 1.00 | 26.71 |
| 817 | N | SER | 1164 | 74.718 | 29.151 | 51.704 | 1.00 | 23.80 |
| 818 | CA | SER | 1164 | 74.839 | 30.597 | 51.805 | 1.00 | 23.26 |
| 819 | CB | SER | 1164 | 74.376 | 31.267 | 50.503 | 1.00 | 23.11 |
| 820 | OG | SER | 1164 | 75.068 | 30.759 | 49.372 | 1.00 | 25.78 |
| 821 | C | SER | 1164 | 74.115 | 31.243 | 52.968 | 1.00 | 23.96 |
| 822 | O | SER | 1164 | 74.153 | 32.466 | 53.102 | 1.00 | 26.14 |
| 823 | N | SER | 1165 | 73.412 | 30.474 | 53.789 | 1.00 | 25.28 |
| 824 | CA | SER | 1165 | 72.719 | 31.113 | 54.905 | 1.00 | 26.92 |
| 825 | CB | SER | 1165 | 71.788 | 30.142 | 55.647 | 1.00 | 29.04 |
| 826 | OG | SER | 1165 | 72.468 | 28.977 | 56.096 | 1.00 | 35.95 |
| 827 | C | SER | 1165 | 73.790 | 31.695 | 55.820 | 1.00 | 24.96 |
| 828 | O | SER | 1165 | 74.785 | 31.036 | 56.126 | 1.00 | 25.60 |
| 829 | N | GLY | 1166 | 73.610 | 32.951 | 56.193 | 1.00 | 23.93 |
| 830 | CA | GLY | 1166 | 74.582 | 33.630 | 57.026 | 1.00 | 22.49 |

FIG. 3A-18

| Atom | Atom Type | Resid | # | X | Y | Z | OCC | B |
|---|---|---|---|---|---|---|---|---|
| 831 | C | GLY | 1166 | 75.176 | 34.762 | 56.207 | 1.00 | 22.45 |
| 832 | O | GLY | 1166 | 75.788 | 35.677 | 56.752 | 1.00 | 20.96 |
| 833 | N | GLY | 1167 | 74.965 | 34.692 | 54.892 | 1.00 | 22.45 |
| 834 | CA | GLY | 1167 | 75.452 | 35.697 | 53.964 | 1.00 | 22.73 |
| 835 | C | GLY | 1167 | 74.687 | 37.003 | 54.055 | 1.00 | 21.55 |
| 836 | O | GLY | 1167 | 73.648 | 37.067 | 54.712 | 1.00 | 21.50 |
| 837 | N | PRO | 1168 | 75.161 | 38.061 | 53.384 | 1.00 | 20.49 |
| 838 | CD | PRO | 1168 | 76.450 | 38.180 | 52.673 | 1.00 | 18.54 |
| 839 | CA | PRO | 1168 | 74.478 | 39.354 | 53.439 | 1.00 | 20.96 |
| 840 | CB | PRO | 1168 | 75.638 | 40.333 | 53.300 | 1.00 | 17.41 |
| 841 | CG | PRO | 1168 | 76.463 | 39.663 | 52.235 | 1.00 | 16.92 |
| 842 | C | PRO | 1168 | 73.424 | 39.644 | 52.368 | 1.00 | 21.87 |
| 843 | O | PRO | 1168 | 73.480 | 39.127 | 51.251 | 1.00 | 23.31 |
| 844 | N | LEU | 1169 | 72.472 | 40.496 | 52.731 | 1.00 | 20.95 |
| 845 | CA | LEU | 1169 | 71.441 | 40.950 | 51.818 | 1.00 | 20.67 |
| 846 | CB | LEU | 1169 | 70.045 | 40.673 | 52.381 | 1.00 | 22.16 |
| 847 | CG | LEU | 1169 | 69.367 | 39.460 | 51.733 | 1.00 | 23.29 |
| 848 | CD1 | LEU | 1169 | 68.426 | 38.826 | 52.686 | 1.00 | 25.16 |
| 849 | CD2 | LEU | 1169 | 68.652 | 39.858 | 50.459 | 1.00 | 24.84 |
| 850 | C | LEU | 1169 | 71.751 | 42.432 | 51.781 | 1.00 | 20.26 |
| 851 | O | LEU | 1169 | 71.537 | 43.142 | 52.761 | 1.00 | 20.99 |
| 852 | N | LEU | 1170 | 72.369 | 42.855 | 50.686 | 1.00 | 20.65 |
| 853 | CA | LEU | 1170 | 72.812 | 44.230 | 50.477 | 1.00 | 20.86 |
| 854 | CB | LEU | 1170 | 74.097 | 44.217 | 49.647 | 1.00 | 18.73 |
| 855 | CG | LEU | 1170 | 75.246 | 43.277 | 50.028 | 1.00 | 19.61 |
| 856 | CD1 | LEU | 1170 | 76.349 | 43.392 | 48.987 | 1.00 | 17.63 |
| 857 | CD2 | LEU | 1170 | 75.772 | 43.597 | 51.419 | 1.00 | 15.34 |
| 858 | C | LEU | 1170 | 71.820 | 45.149 | 49.774 | 1.00 | 22.02 |
| 859 | O | LEU | 1170 | 71.111 | 44.729 | 48.868 | 1.00 | 25.14 |
| 860 | N | CYS | 1171 | 71.801 | 46.414 | 50.171 | 1.00 | 22.01 |
| 861 | CA | CYS | 1171 | 70.930 | 47.395 | 49.543 | 1.00 | 22.45 |
| 862 | CB | CYS | 1171 | 70.628 | 48.524 | 50.531 | 1.00 | 22.30 |
| 863 | SG | CYS | 1171 | 71.982 | 49.681 | 50.780 | 1.00 | 26.39 |
| 864 | C | CYS | 1171 | 71.712 | 47.929 | 48.332 | 1.00 | 23.53 |
| 865 | O | CYS | 1171 | 72.858 | 47.527 | 48.110 | 1.00 | 22.06 |
| 866 | N | PRO | 1172 | 71.124 | 48.850 | 47.542 | 1.00 | 25.28 |
| 867 | CD | PRO | 1172 | 69.721 | 49.317 | 47.553 | 1.00 | 23.57 |
| 868 | CA | PRO | 1172 | 71.830 | 49.396 | 46.371 | 1.00 | 23.81 |
| 869 | CB | PRO | 1172 | 70.831 | 50.418 | 45.834 | 1.00 | 22.44 |
| 870 | CG | PRO | 1172 | 69.517 | 49.769 | 46.131 | 1.00 | 21.24 |
| 871 | C | PRO | 1172 | 73.188 | 50.054 | 46.661 | 1.00 | 24.42 |
| 872 | O | PRO | 1172 | 73.981 | 50.288 | 45.746 | 1.00 | 25.44 |
| 873 | N | ALA | 1173 | 73.446 | 50.366 | 47.927 | 1.00 | 23.25 |
| 874 | CA | ALA | 1173 | 74.691 | 51.010 | 48.333 | 1.00 | 22.05 |
| 875 | CB | ALA | 1173 | 74.381 | 52.102 | 49.356 | 1.00 | 19.70 |
| 876 | C | ALA | 1173 | 75.731 | 50.033 | 48.903 | 1.00 | 21.83 |
| 877 | O | ALA | 1173 | 76.794 | 50.449 | 49.365 | 1.00 | 21.56 |
| 878 | N | GLY | 1174 | 75.402 | 48.745 | 48.911 | 1.00 | 20.69 |
| 879 | CA | GLY | 1174 | 76.313 | 47.746 | 49.444 | 1.00 | 20.88 |

FIG. 3A-19

| Atom | Atom Type | Resid | # | X | Y | Z | OCC | B |
|---|---|---|---|---|---|---|---|---|
| 880 | C | GLY | 1174 | 76.286 | 47.625 | 50.962 | 1.00 | 21.00 |
| 881 | O | GLY | 1174 | 77.148 | 46.975 | 51.549 | 1.00 | 22.80 |
| 882 | N | HIS | 1175 | 75.310 | 48.261 | 51.599 | 1.00 | 20.13 |
| 883 | CA | HIS | 1175 | 75.170 | 48.218 | 53.052 | 1.00 | 19.74 |
| 884 | CB | HIS | 1175 | 74.585 | 49.533 | 53.569 | 1.00 | 20.08 |
| 885 | CG | HIS | 1175 | 75.465 | 50.726 | 53.336 | 1.00 | 21.55 |
| 886 | CD2 | HIS | 1175 | 76.660 | 50.845 | 52.714 | 1.00 | 23.16 |
| 887 | ND1 | HIS | 1175 | 75.134 | 51.990 | 53.775 | 1.00 | 22.98 |
| 888 | CE1 | HIS | 1175 | 76.088 | 52.837 | 53.433 | 1.00 | 23.40 |
| 889 | NE2 | HIS | 1175 | 77.026 | 52.168 | 52.787 | 1.00 | 22.42 |
| 890 | C | HIS | 1175 | 74.277 | 47.049 | 53.481 | 1.00 | 20.52 |
| 891 | O | HIS | 1175 | 73.344 | 46.679 | 52.770 | 1.00 | 21.87 |
| 892 | N | ALA | 1176 | 74.553 | 46.492 | 54.653 | 1.00 | 19.06 |
| 893 | CA | ALA | 1176 | 73.809 | 45.362 | 55.182 | 1.00 | 18.89 |
| 894 | CB | ALA | 1176 | 74.470 | 44.863 | 56.442 | 1.00 | 18.59 |
| 895 | C | ALA | 1176 | 72.353 | 45.643 | 55.475 | 1.00 | 21.37 |
| 896 | O | ALA | 1176 | 72.031 | 46.496 | 56.304 | 1.00 | 21.49 |
| 897 | N | VAL | 1177 | 71.473 | 44.897 | 54.817 | 1.00 | 22.39 |
| 898 | CA | VAL | 1177 | 70.035 | 45.024 | 55.023 | 1.00 | 21.72 |
| 899 | CB | VAL | 1177 | 69.246 | 44.821 | 53.703 | 1.00 | 22.74 |
| 900 | CG1 | VAL | 1177 | 67.741 | 44.788 | 53.975 | 1.00 | 22.68 |
| 901 | CG2 | VAL | 1177 | 69.582 | 45.930 | 52.720 | 1.00 | 20.67 |
| 902 | C | VAL | 1177 | 69.634 | 43.949 | 56.027 | 1.00 | 21.01 |
| 903 | O | VAL | 1177 | 68.814 | 44.182 | 56.915 | 1.00 | 22.35 |
| 904 | N | GLY | 1178 | 70.245 | 42.777 | 55.891 | 1.00 | 20.58 |
| 905 | CA | GLY | 1178 | 69.968 | 41.668 | 56.782 | 1.00 | 19.29 |
| 906 | C | GLY | 1178 | 70.865 | 40.491 | 56.460 | 1.00 | 20.72 |
| 907 | O | GLY | 1178 | 71.693 | 40.564 | 55.545 | 1.00 | 20.77 |
| 908 | N | LEU | 1179 | 70.752 | 39.436 | 57.260 | 1.00 | 23.38 |
| 909 | CA | LEU | 1179 | 71.521 | 38.208 | 57.066 | 1.00 | 24.90 |
| 910 | CB | LEU | 1179 | 72.001 | 37.651 | 58.408 | 1.00 | 27.14 |
| 911 | CG | LEU | 1179 | 73.435 | 37.842 | 58.896 | 1.00 | 27.77 |
| 912 | CD1 | LEU | 1179 | 73.765 | 39.313 | 58.996 | 1.00 | 29.16 |
| 913 | CD2 | LEU | 1179 | 73.573 | 37.177 | 60.250 | 1.00 | 27.55 |
| 914 | C | LEU | 1179 | 70.578 | 37.189 | 56.461 | 1.00 | 25.10 |
| 915 | O | LEU | 1179 | 69.475 | 37.000 | 56.964 | 1.00 | 26.82 |
| 916 | N | PHE | 1180 | 70.987 | 36.552 | 55.375 | 1.00 | 25.52 |
| 917 | CA | PHE | 1180 | 70.163 | 35.536 | 54.744 | 1.00 | 26.02 |
| 918 | CB | PHE | 1180 | 70.861 | 35.030 | 53.485 | 1.00 | 26.33 |
| 919 | CG | PHE | 1180 | 70.193 | 33.858 | 52.841 | 1.00 | 25.63 |
| 920 | CD1 | PHE | 1180 | 68.809 | 33.754 | 52.804 | 1.00 | 24.18 |
| 921 | CD2 | PHE | 1180 | 70.961 | 32.855 | 52.258 | 1.00 | 26.86 |
| 922 | CE1 | PHE | 1180 | 68.203 | 32.669 | 52.196 | 1.00 | 26.34 |
| 923 | CE2 | PHE | 1180 | 70.359 | 31.760 | 51.646 | 1.00 | 28.46 |
| 924 | CZ | PHE | 1180 | 68.978 | 31.667 | 51.614 | 1.00 | 27.68 |
| 925 | C | PHE | 1180 | 69.947 | 34.403 | 55.751 | 1.00 | 27.04 |
| 926 | O | PHE | 1180 | 70.904 | 33.763 | 56.200 | 1.00 | 28.87 |
| 927 | N | ARG | 1181 | 68.692 | 34.197 | 56.135 | 1.00 | 27.75 |
| 928 | CA | ARG | 1181 | 68.335 | 33.168 | 57.105 | 1.00 | 28.04 |

FIG. 3A-20

| Atom | Atom Type | Resid | # | X | Y | Z | OCC | B |
|---|---|---|---|---|---|---|---|---|
| 929 | CB | ARG | 1181 | 67.193 | 33.647 | 58.014 | 1.00 | 28.31 |
| 930 | CG | ARG | 1181 | 66.773 | 32.609 | 59.047 | 1.00 | 30.17 |
| 931 | CD | ARG | 1181 | 65.340 | 32.795 | 59.494 | 1.00 | 33.18 |
| 932 | NE | ARG | 1181 | 65.225 | 33.558 | 60.730 | 1.00 | 37.63 |
| 933 | CZ | ARG | 1181 | 64.538 | 34.694 | 60.858 | 1.00 | 40.99 |
| 934 | NH1 | ARG | 1181 | 63.900 | 35.226 | 59.818 | 1.00 | 40.68 |
| 935 | NH2 | ARG | 1181 | 64.455 | 35.281 | 62.048 | 1.00 | 42.67 |
| 936 | C | ARG | 1181 | 67.962 | 31.827 | 56.477 | 1.00 | 28.46 |
| 937 | O | ARG | 1181 | 68.499 | 30.784 | 56.872 | 1.00 | 30.26 |
| 938 | N | ALA | 1182 | 67.046 | 31.838 | 55.514 | 1.00 | 27.65 |
| 939 | CA | ALA | 1182 | 66.637 | 30.589 | 54.887 | 1.00 | 26.77 |
| 940 | CB | ALA | 1182 | 65.686 | 29.841 | 55.794 | 1.00 | 28.57 |
| 941 | C | ALA | 1182 | 66.002 | 30.777 | 53.529 | 1.00 | 26.90 |
| 942 | O | ALA | 1182 | 65.457 | 31.842 | 53.223 | 1.00 | 24.79 |
| 943 | N | ALA | 1183 | 66.085 | 29.727 | 52.720 | 1.00 | 27.64 |
| 944 | CA | ALA | 1183 | 65.519 | 29.714 | 51.382 | 1.00 | 29.29 |
| 945 | CB | ALA | 1183 | 66.356 | 28.821 | 50.469 | 1.00 | 28.99 |
| 946 | C | ALA | 1183 | 64.080 | 29.207 | 51.433 | 1.00 | 31.69 |
| 947 | O | ALA | 1183 | 63.803 | 28.136 | 51.992 | 1.00 | 31.90 |
| 948 | N | VAL | 1184 | 63.170 | 30.012 | 50.893 | 1.00 | 32.81 |
| 949 | CA | VAL | 1184 | 61.751 | 29.681 | 50.833 | 1.00 | 32.42 |
| 950 | CB | VAL | 1184 | 60.893 | 30.928 | 51.005 | 1.00 | 30.12 |
| 951 | CG1 | VAL | 1184 | 59.440 | 30.583 | 50.781 | 1.00 | 32.26 |
| 952 | CG2 | VAL | 1184 | 61.106 | 31.522 | 52.380 | 1.00 | 30.64 |
| 953 | C | VAL | 1184 | 61.498 | 29.131 | 49.441 | 1.00 | 33.36 |
| 954 | O | VAL | 1184 | 61.370 | 29.894 | 48.478 | 1.00 | 32.09 |
| 955 | N | CYS | 1185 | 61.403 | 27.816 | 49.326 | 1.00 | 35.08 |
| 956 | CA | CYS | 1185 | 61.211 | 27.215 | 48.017 | 1.00 | 39.13 |
| 957 | CB | CYS | 1185 | 62.486 | 26.482 | 47.601 | 1.00 | 41.48 |
| 958 | SG | CYS | 1185 | 63.419 | 25.872 | 48.998 | 1.00 | 44.16 |
| 959 | C | CYS | 1185 | 60.020 | 26.297 | 47.822 | 1.00 | 38.16 |
| 960 | O | CYS | 1185 | 59.487 | 25.720 | 48.772 | 1.00 | 36.83 |
| 961 | N | THR | 1186 | 59.574 | 26.236 | 46.571 | 1.00 | 38.73 |
| 962 | CA | THR | 1186 | 58.469 | 25.385 | 46.185 | 1.00 | 37.64 |
| 963 | CB | THR | 1186 | 57.582 | 26.052 | 45.133 | 1.00 | 33.24 |
| 964 | OG1 | THR | 1186 | 57.162 | 27.327 | 45.617 | 1.00 | 31.32 |
| 965 | CG2 | THR | 1186 | 56.340 | 25.228 | 44.896 | 1.00 | 35.61 |
| 966 | C | THR | 1186 | 59.040 | 24.049 | 45.703 | 1.00 | 40.01 |
| 967 | O | THR | 1186 | 59.763 | 23.394 | 46.453 | 1.00 | 43.80 |
| 968 | N | ARG | 1187 | 58.815 | 23.666 | 44.454 | 1.00 | 40.59 |
| 969 | CA | ARG | 1187 | 59.313 | 22.371 | 44.016 | 1.00 | 42.08 |
| 970 | CB | ARG | 1187 | 58.452 | 21.812 | 42.879 | 1.00 | 44.63 |
| 971 | CG | ARG | 1187 | 56.993 | 21.591 | 43.280 | 1.00 | 45.00 |
| 972 | CD | ARG | 1187 | 56.253 | 20.703 | 42.298 | 1.00 | 45.42 |
| 973 | NE | ARG | 1187 | 56.736 | 19.327 | 42.361 | 1.00 | 47.14 |
| 974 | CZ | ARG | 1187 | 57.309 | 18.683 | 41.348 | 1.00 | 48.66 |
| 975 | NH1 | ARG | 1187 | 57.475 | 19.287 | 40.175 | 1.00 | 49.91 |
| 976 | NH2 | ARG | 1187 | 57.731 | 17.433 | 41.511 | 1.00 | 49.91 |
| 977 | C | ARG | 1187 | 60.788 | 22.349 | 43.668 | 1.00 | 42.04 |

FIG. 3A-21

| Atom | Atom Type | Resid | # | X | Y | Z | OCC | B |
|---|---|---|---|---|---|---|---|---|
| 978 | O | ARG | 1187 | 61.165 | 22.021 | 42.545 | 1.00 | 44.12 |
| 979 | N | GLY | 1188 | 61.623 | 22.687 | 44.647 | 1.00 | 41.58 |
| 980 | CA | GLY | 1188 | 63.060 | 22.692 | 44.435 | 1.00 | 40.35 |
| 981 | C | GLY | 1188 | 63.591 | 24.022 | 43.935 | 1.00 | 39.09 |
| 982 | O | GLY | 1188 | 64.800 | 24.235 | 43.881 | 1.00 | 40.73 |
| 983 | N | VAL | 1189 | 62.692 | 24.921 | 43.561 | 1.00 | 36.60 |
| 984 | CA | VAL | 1189 | 63.097 | 26.220 | 43.069 | 1.00 | 35.55 |
| 985 | CB | VAL | 1189 | 62.290 | 26.614 | 41.837 | 1.00 | 34.59 |
| 986 | CG1 | VAL | 1189 | 62.634 | 28.026 | 41.401 | 1.00 | 36.44 |
| 987 | CG2 | VAL | 1189 | 62.579 | 25.646 | 40.716 | 1.00 | 35.37 |
| 988 | C | VAL | 1189 | 62.928 | 27.276 | 44.145 | 1.00 | 36.38 |
| 989 | O | VAL | 1189 | 61.834 | 27.450 | 44.677 | 1.00 | 37.93 |
| 990 | N | ALA | 1190 | 64.027 | 27.928 | 44.510 | 1.00 | 35.83 |
| 991 | CA | ALA | 1190 | 64.002 | 28.983 | 45.513 | 1.00 | 34.95 |
| 992 | CB | ALA | 1190 | 65.400 | 29.240 | 46.045 | 1.00 | 34.41 |
| 993 | C | ALA | 1190 | 63.465 | 30.228 | 44.827 | 1.00 | 35.05 |
| 994 | O | ALA | 1190 | 64.062 | 30.715 | 43.865 | 1.00 | 35.76 |
| 995 | N | LYS | 1191 | 62.321 | 30.717 | 45.292 | 1.00 | 34.34 |
| 996 | CA | LYS | 1191 | 61.710 | 31.907 | 44.709 | 1.00 | 33.55 |
| 997 | CB | LYS | 1191 | 60.252 | 31.636 | 44.321 | 1.00 | 36.37 |
| 998 | CG | LYS | 1191 | 60.037 | 30.443 | 43.404 | 1.00 | 38.02 |
| 999 | CD | LYS | 1191 | 58.577 | 30.318 | 43.028 | 1.00 | 41.03 |
| 1000 | CE | LYS | 1191 | 58.333 | 29.133 | 42.108 | 1.00 | 45.01 |
| 1001 | NZ | LYS | 1191 | 56.902 | 29.078 | 41.674 | 1.00 | 45.80 |
| 1002 | C | LYS | 1191 | 61.761 | 33.071 | 45.692 | 1.00 | 33.05 |
| 1003 | O | LYS | 1191 | 61.652 | 34.231 | 45.298 | 1.00 | 36.29 |
| 1004 | N | ALA | 1192 | 61.896 | 32.767 | 46.976 | 1.00 | 30.97 |
| 1005 | CA | ALA | 1192 | 61.955 | 33.809 | 47.985 | 1.00 | 28.85 |
| 1006 | CB | ALA | 1192 | 60.615 | 33.971 | 48.684 | 1.00 | 28.99 |
| 1007 | C | ALA | 1192 | 63.051 | 33.494 | 48.984 | 1.00 | 28.42 |
| 1008 | O | ALA | 1192 | 63.596 | 32.384 | 49.009 | 1.00 | 27.40 |
| 1009 | N | VAL | 1193 | 63.299 | 34.452 | 49.863 | 1.00 | 27.93 |
| 1010 | CA | VAL | 1193 | 64.355 | 34.356 | 50.847 | 1.00 | 27.23 |
| 1011 | CB | VAL | 1193 | 65.569 | 35.180 | 50.329 | 1.00 | 27.43 |
| 1012 | CG1 | VAL | 1193 | 66.002 | 36.251 | 51.317 | 1.00 | 26.78 |
| 1013 | CG2 | VAL | 1193 | 66.696 | 34.258 | 49.948 | 1.00 | 26.32 |
| 1014 | C | VAL | 1193 | 63.858 | 34.863 | 52.204 | 1.00 | 28.65 |
| 1015 | O | VAL | 1193 | 63.059 | 35.803 | 52.281 | 1.00 | 29.70 |
| 1016 | N | ASP | 1194 | 64.336 | 34.233 | 53.268 | 1.00 | 29.83 |
| 1017 | CA | ASP | 1194 | 63.961 | 34.593 | 54.634 | 1.00 | 31.77 |
| 1018 | CB | ASP | 1194 | 63.611 | 33.308 | 55.403 | 1.00 | 35.32 |
| 1019 | CG | ASP | 1194 | 62.533 | 33.513 | 56.461 | 1.00 | 39.12 |
| 1020 | OD1 | ASP | 1194 | 62.701 | 32.961 | 57.574 | 1.00 | 40.47 |
| 1021 | OD2 | ASP | 1194 | 61.508 | 34.176 | 56.169 | 1.00 | 39.60 |
| 1022 | C | ASP | 1194 | 65.218 | 35.227 | 55.226 | 1.00 | 29.50 |
| 1023 | O | ASP | 1194 | 66.317 | 34.724 | 54.995 | 1.00 | 30.45 |
| 1024 | N | PHE | 1195 | 65.092 | 36.322 | 55.966 | 1.00 | 27.58 |
| 1025 | CA | PHE | 1195 | 66.292 | 36.927 | 56.537 | 1.00 | 25.93 |
| 1026 | CB | PHE | 1195 | 66.981 | 37.869 | 55.532 | 1.00 | 21.65 |

FIG. 3A-22

| Atom | Atom Type | Resid | # | X | Y | Z | OCC | B |
|---|---|---|---|---|---|---|---|---|
| 1027 | CG | PHE | 1195 | 66.204 | 39.118 | 55.204 | 1.00 | 17.29 |
| 1028 | CD1 | PHE | 1195 | 66.358 | 40.267 | 55.969 | 1.00 | 17.07 |
| 1029 | CD2 | PHE | 1195 | 65.363 | 39.162 | 54.100 | 1.00 | 17.69 |
| 1030 | CE1 | PHE | 1195 | 65.689 | 41.447 | 55.644 | 1.00 | 17.82 |
| 1031 | CE2 | PHE | 1195 | 64.685 | 40.343 | 53.761 | 1.00 | 19.76 |
| 1032 | CZ | PHE | 1195 | 64.849 | 41.491 | 54.538 | 1.00 | 18.59 |
| 1033 | C | PHE | 1195 | 66.140 | 37.590 | 57.897 | 1.00 | 25.99 |
| 1034 | O | PHE | 1195 | 65.034 | 37.746 | 58.404 | 1.00 | 27.20 |
| 1035 | N | ILE | 1196 | 67.283 | 37.916 | 58.496 | 1.00 | 26.69 |
| 1036 | CA | ILE | 1196 | 67.389 | 38.562 | 59.804 | 1.00 | 25.40 |
| 1037 | CB | ILE | 1196 | 68.535 | 37.900 | 60.617 | 1.00 | 23.91 |
| 1038 | CG2 | ILE | 1196 | 68.599 | 38.457 | 62.027 | 1.00 | 22.64 |
| 1039 | CG1 | ILE | 1196 | 68.357 | 36.381 | 60.645 | 1.00 | 20.68 |
| 1040 | CD1 | ILE | 1196 | 69.570 | 35.656 | 61.152 | 1.00 | 20.36 |
| 1041 | C | ILE | 1196 | 67.777 | 40.026 | 59.548 | 1.00 | 28.07 |
| 1042 | O | ILE | 1196 | 68.907 | 40.309 | 59.147 | 1.00 | 31.19 |
| 1043 | N | PRO | 1197 | 66.853 | 40.972 | 59.757 | 1.00 | 28.04 |
| 1044 | CD | PRO | 1197 | 65.466 | 40.830 | 60.225 | 1.00 | 27.62 |
| 1045 | CA | PRO | 1197 | 67.187 | 42.382 | 59.521 | 1.00 | 29.04 |
| 1046 | CB | PRO | 1197 | 65.851 | 43.087 | 59.764 | 1.00 | 27.29 |
| 1047 | CG | PRO | 1197 | 65.177 | 42.204 | 60.758 | 1.00 | 27.91 |
| 1048 | C | PRO | 1197 | 68.296 | 42.924 | 60.437 | 1.00 | 30.39 |
| 1049 | O | PRO | 1197 | 68.445 | 42.469 | 61.571 | 1.00 | 30.42 |
| 1050 | N | VAL | 1198 | 69.060 | 43.904 | 59.950 | 1.00 | 32.28 |
| 1051 | CA | VAL | 1198 | 70.149 | 44.497 | 60.738 | 1.00 | 32.71 |
| 1052 | CB | VAL | 1198 | 70.968 | 45.569 | 59.977 | 1.00 | 31.13 |
| 1053 | CG1 | VAL | 1198 | 71.893 | 44.906 | 58.992 | 1.00 | 32.44 |
| 1054 | CG2 | VAL | 1198 | 70.060 | 46.576 | 59.294 | 1.00 | 30.27 |
| 1055 | C | VAL | 1198 | 69.706 | 45.106 | 62.046 | 1.00 | 33.07 |
| 1056 | O | VAL | 1198 | 70.494 | 45.192 | 62.982 | 1.00 | 34.24 |
| 1057 | N | GLU | 1199 | 68.459 | 45.557 | 62.112 | 1.00 | 34.76 |
| 1058 | CA | GLU | 1199 | 67.942 | 46.133 | 63.348 | 1.00 | 35.58 |
| 1059 | CB | GLU | 1199 | 66.502 | 46.601 | 63.167 | 1.00 | 38.30 |
| 1060 | CG | GLU | 1199 | 66.347 | 47.817 | 62.251 | 1.00 | 43.36 |
| 1061 | CD | GLU | 1199 | 66.682 | 47.546 | 60.781 | 1.00 | 44.71 |
| 1062 | OE1 | GLU | 1199 | 67.295 | 48.437 | 60.157 | 1.00 | 46.89 |
| 1063 | OE2 | GLU | 1199 | 66.319 | 46.470 | 60.248 | 1.00 | 43.96 |
| 1064 | C | GLU | 1199 | 68.035 | 45.092 | 64.465 | 1.00 | 35.11 |
| 1065 | O | GLU | 1199 | 68.357 | 45.424 | 65.599 | 1.00 | 35.89 |
| 1066 | N | ASN | 1200 | 67.827 | 43.823 | 64.126 | 1.00 | 34.53 |
| 1067 | CA | ASN | 1200 | 67.918 | 42.750 | 65.108 | 1.00 | 34.98 |
| 1068 | CB | ASN | 1200 | 67.515 | 41.414 | 64.486 | 1.00 | 36.70 |
| 1069 | CG | ASN | 1200 | 66.017 | 41.289 | 64.286 | 1.00 | 40.49 |
| 1070 | OD1 | ASN | 1200 | 65.442 | 40.231 | 64.528 | 1.00 | 43.89 |
| 1071 | ND2 | ASN | 1200 | 65.377 | 42.358 | 63.827 | 1.00 | 40.79 |
| 1072 | C | ASN | 1200 | 69.345 | 42.663 | 65.640 | 1.00 | 35.32 |
| 1073 | O | ASN | 1200 | 69.561 | 42.654 | 66.852 | 1.00 | 35.57 |
| 1074 | N | LEU | 1201 | 70.319 | 42.635 | 64.733 | 1.00 | 34.45 |
| 1075 | CA | LEU | 1201 | 71.727 | 42.568 | 65.124 | 1.00 | 32.80 |

FIG. 3A-23

| Atom | Atom Type | Resid | # | X | Y | Z | OCC | B |
|---|---|---|---|---|---|---|---|---|
| 1076 | CB | LEU | 1201 | 72.643 | 42.631 | 63.900 | 1.00 | 31.13 |
| 1077 | CG | LEU | 1201 | 72.856 | 41.383 | 63.053 | 1.00 | 30.40 |
| 1078 | CD1 | LEU | 1201 | 71.547 | 40.751 | 62.648 | 1.00 | 31.05 |
| 1079 | CD2 | LEU | 1201 | 73.654 | 41.764 | 61.833 | 1.00 | 30.17 |
| 1080 | C | LEU | 1201 | 72.026 | 43.749 | 66.028 | 1.00 | 33.31 |
| 1081 | O | LEU | 1201 | 72.535 | 43.585 | 67.135 | 1.00 | 33.72 |
| 1082 | N | GLU | 1202 | 71.653 | 44.933 | 65.558 | 1.00 | 33.90 |
| 1083 | CA | GLU | 1202 | 71.861 | 46.171 | 66.294 | 1.00 | 35.75 |
| 1084 | CB | GLU | 1202 | 71.292 | 47.351 | 65.500 | 1.00 | 34.70 |
| 1085 | CG | GLU | 1202 | 72.029 | 47.574 | 64.190 | 1.00 | 37.02 |
| 1086 | CD | GLU | 1202 | 71.347 | 48.547 | 63.247 | 1.00 | 40.33 |
| 1087 | OE1 | GLU | 1202 | 71.990 | 48.934 | 62.256 | 1.00 | 43.28 |
| 1088 | OE2 | GLU | 1202 | 70.175 | 48.924 | 63.462 | 1.00 | 44.53 |
| 1089 | C | GLU | 1202 | 71.285 | 46.122 | 67.713 | 1.00 | 37.01 |
| 1090 | O | GLU | 1202 | 71.977 | 46.459 | 68.673 | 1.00 | 38.58 |
| 1091 | N | THR | 1203 | 70.043 | 45.672 | 67.855 | 1.00 | 36.83 |
| 1092 | CA | THR | 1203 | 69.435 | 45.592 | 69.174 | 1.00 | 38.22 |
| 1093 | CB | THR | 1203 | 67.956 | 45.209 | 69.099 | 1.00 | 38.67 |
| 1094 | OG1 | THR | 1203 | 67.828 | 43.951 | 68.434 | 1.00 | 42.02 |
| 1095 | CG2 | THR | 1203 | 67.168 | 46.264 | 68.352 | 1.00 | 38.87 |
| 1096 | C | THR | 1203 | 70.156 | 44.548 | 70.001 | 1.00 | 39.56 |
| 1097 | O | THR | 1203 | 70.425 | 44.764 | 71.180 | 1.00 | 40.65 |
| 1098 | N | THR | 1204 | 70.479 | 43.421 | 69.370 | 1.00 | 40.29 |
| 1099 | CA | THR | 1204 | 71.180 | 42.328 | 70.040 | 1.00 | 40.51 |
| 1100 | CB | THR | 1204 | 71.409 | 41.146 | 69.075 | 1.00 | 39.96 |
| 1101 | OG1 | THR | 1204 | 70.150 | 40.520 | 68.785 | 1.00 | 37.72 |
| 1102 | CG2 | THR | 1204 | 72.353 | 40.120 | 69.677 | 1.00 | 41.21 |
| 1103 | C | THR | 1204 | 72.492 | 42.818 | 70.648 | 1.00 | 41.33 |
| 1104 | O | THR | 1204 | 72.932 | 42.322 | 71.684 | 1.00 | 42.16 |
| 1105 | N | MET | 1205 | 73.101 | 43.810 | 70.012 | 1.00 | 42.92 |
| 1106 | CA | MET | 1205 | 74.338 | 44.395 | 70.510 | 1.00 | 44.88 |
| 1107 | CB | MET | 1205 | 75.064 | 45.136 | 69.388 | 1.00 | 43.43 |
| 1108 | CG | MET | 1205 | 75.778 | 44.265 | 68.388 | 1.00 | 41.30 |
| 1109 | SD | MET | 1205 | 76.649 | 45.304 | 67.195 | 1.00 | 38.98 |
| 1110 | CE | MET | 1205 | 75.690 | 45.025 | 65.732 | 1.00 | 39.73 |
| 1111 | C | MET | 1205 | 74.008 | 45.401 | 71.612 | 1.00 | 48.30 |
| 1112 | O | MET | 1205 | 74.680 | 46.434 | 71.732 | 1.00 | 50.45 |
| 1113 | N | ALA | 1206 | 72.985 | 45.106 | 72.415 | 1.00 | 51.29 |
| 1114 | CA | ALA | 1206 | 72.560 | 46.001 | 73.494 | 1.00 | 52.72 |
| 1115 | CB | ALA | 1206 | 71.741 | 47.167 | 72.919 | 1.00 | 51.79 |
| 1116 | C | ALA | 1206 | 71.746 | 45.253 | 74.550 | 1.00 | 52.50 |
| 1117 | O | ALA | 1206 | 70.842 | 44.487 | 74.147 | 1.00 | 52.28 | sNS4A COORDINATES (Complex A)

| Atom | Atom Type | Resid | # | X | Y | Z | OCC | B |
|---|---|---|---|---|---|---|---|---|
| 2427 | N | GLY | 1678 | 82.660 | 20.678 | 69.142 | 1.00 | 47.82 |

FIG. 3A-24

|  | Atom | | | | | | |
|---|---|---|---|---|---|---|---|
| Atom | Type | Resid | # | X | Y | Z | OCC | B |
| 2428 | CA | GLY | 1678 | 83.325 | 21.195 | 67.901 | 1.00 | 47.45 |
| 2429 | C | GLY | 1678 | 83.444 | 22.729 | 67.863 | 1.00 | 42.58 |
| 2430 | O | GLY | 1678 | 83.086 | 23.435 | 68.815 | 1.00 | 46.32 |
| 2431 | N | SER | 1679 | 83.951 | 23.237 | 66.745 | 1.00 | 39.26 |
| 2432 | CA | SER | 1679 | 84.188 | 24.669 | 66.594 | 1.00 | 35.38 |
| 2433 | CB | SER | 1679 | 85.628 | 24.981 | 67.011 | 1.00 | 34.24 |
| 2434 | OG | SER | 1679 | 85.746 | 26.265 | 67.587 | 1.00 | 33.09 |
| 2435 | C | SER | 1679 | 83.965 | 25.057 | 65.134 | 1.00 | 32.76 |
| 2436 | O | SER | 1679 | 84.084 | 24.218 | 64.240 | 1.00 | 34.29 |
| 2437 | N | VAL | 1680 | 83.594 | 26.307 | 64.894 | 1.00 | 29.61 |
| 2438 | CA | VAL | 1680 | 83.365 | 26.784 | 63.533 | 1.00 | 27.92 |
| 2439 | CB | VAL | 1680 | 82.341 | 27.936 | 63.495 | 1.00 | 27.03 |
| 2440 | CG1 | VAL | 1680 | 81.995 | 28.277 | 62.069 | 1.00 | 26.39 |
| 2441 | CG2 | VAL | 1680 | 81.099 | 27.569 | 64.277 | 1.00 | 27.69 |
| 2442 | C | VAL | 1680 | 84.692 | 27.311 | 63.007 | 1.00 | 26.65 |
| 2443 | O | VAL | 1680 | 85.349 | 28.115 | 63.666 | 1.00 | 28.02 |
| 2444 | N | VAL | 1681 | 85.108 | 26.844 | 61.842 | 1.00 | 24.80 |
| 2445 | CA | VAL | 1681 | 86.364 | 27.300 | 61.278 | 1.00 | 23.49 |
| 2446 | CB | VAL | 1681 | 87.331 | 26.117 | 61.027 | 1.00 | 23.05 |
| 2447 | CG1 | VAL | 1681 | 87.591 | 25.384 | 62.314 | 1.00 | 21.97 |
| 2448 | CG2 | VAL | 1681 | 86.751 | 25.153 | 60.018 | 1.00 | 24.91 |
| 2449 | C | VAL | 1681 | 86.106 | 28.061 | 59.985 | 1.00 | 22.71 |
| 2450 | O | VAL | 1681 | 85.156 | 27.762 | 59.261 | 1.00 | 22.32 |
| 2451 | N | ILE | 1682 | 86.923 | 29.077 | 59.729 | 1.00 | 22.79 |
| 2452 | CA | ILE | 1682 | 86.809 | 29.899 | 58.528 | 1.00 | 19.66 |
| 2453 | CB | ILE | 1682 | 87.309 | 31.332 | 58.811 | 1.00 | 16.80 |
| 2454 | CG2 | ILE | 1682 | 87.324 | 32.164 | 57.540 | 1.00 | 16.76 |
| 2455 | CG1 | ILE | 1682 | 86.417 | 31.981 | 59.875 | 1.00 | 13.77 |
| 2456 | CD1 | ILE | 1682 | 86.965 | 33.244 | 60.432 | 1.00 | 9.56 |
| 2457 | C | ILE | 1682 | 87.627 | 29.247 | 57.418 | 1.00 | 19.97 |
| 2458 | O | ILE | 1682 | 88.844 | 29.115 | 57.522 | 1.00 | 20.81 |
| 2459 | N | VAL | 1683 | 86.946 | 28.826 | 56.361 | 1.00 | 20.17 |
| 2460 | CA | VAL | 1683 | 87.599 | 28.157 | 55.253 | 1.00 | 18.67 |
| 2461 | CB | VAL | 1683 | 86.827 | 26.867 | 54.857 | 1.00 | 20.13 |
| 2462 | CG1 | VAL | 1683 | 86.595 | 25.992 | 56.091 | 1.00 | 19.43 |
| 2463 | CG2 | VAL | 1683 | 85.511 | 27.205 | 54.188 | 1.00 | 21.44 |
| 2464 | C | VAL | 1683 | 87.785 | 29.039 | 54.027 | 1.00 | 17.87 |
| 2465 | O | VAL | 1683 | 88.279 | 28.592 | 52.993 | 1.00 | 19.88 |
| 2466 | N | GLY | 1684 | 87.400 | 30.297 | 54.135 | 1.00 | 16.04 |
| 2467 | CA | GLY | 1684 | 87.547 | 31.186 | 53.005 | 1.00 | 13.85 |
| 2468 | C | GLY | 1684 | 87.006 | 32.540 | 53.374 | 1.00 | 14.18 |
| 2469 | O | GLY | 1684 | 86.476 | 32.709 | 54.473 | 1.00 | 11.33 |
| 2470 | N | ARG | 1685 | 87.119 | 33.492 | 52.452 | 1.00 | 16.02 |
| 2471 | CA | ARG | 1685 | 86.660 | 34.861 | 52.660 | 1.00 | 16.38 |
| 2472 | CB | ARG | 1685 | 87.800 | 35.715 | 53.219 | 1.00 | 17.53 |
| 2473 | CG | ARG | 1685 | 88.339 | 35.249 | 54.559 | 1.00 | 18.90 |
| 2474 | CD | ARG | 1685 | 89.566 | 36.039 | 54.945 | 1.00 | 20.79 |
| 2475 | NE | ARG | 1685 | 90.609 | 35.890 | 53.940 | 1.00 | 21.09 |
| 2476 | CZ | ARG | 1685 | 91.532 | 36.808 | 53.676 | 1.00 | 22.64 |

FIG. 3A-25

| Atom | Atom Type | Resid | # | X | Y | Z | OCC | B |
|---|---|---|---|---|---|---|---|---|
| 2477 | NH1 | ARG | 1685 | 91.552 | 37.957 | 54.348 | 1.00 | 21.65 |
| 2478 | NH2 | ARG | 1685 | 92.426 | 36.581 | 52.722 | 1.00 | 21.05 |
| 2479 | C | ARG | 1685 | 86.180 | 35.460 | 51.343 | 1.00 | 15.81 |
| 2480 | O | ARG | 1685 | 86.606 | 35.034 | 50.273 | 1.00 | 17.35 |
| 2481 | N | ILE | 1686 | 85.313 | 36.464 | 51.432 | 1.00 | 14.82 |
| 2482 | CA | ILE | 1686 | 84.761 | 37.142 | 50.267 | 1.00 | 13.14 |
| 2483 | CB | ILE | 1686 | 83.249 | 36.799 | 50.100 | 1.00 | 14.91 |
| 2484 | CG2 | ILE | 1686 | 82.530 | 37.816 | 49.216 | 1.00 | 9.50 |
| 2485 | CG1 | ILE | 1686 | 83.098 | 35.380 | 49.543 | 1.00 | 16.63 |
| 2486 | CD1 | ILE | 1686 | 81.686 | 34.958 | 49.338 | 1.00 | 16.16 |
| 2487 | C | ILE | 1686 | 84.909 | 38.637 | 50.472 | 1.00 | 13.59 |
| 2488 | O | ILE | 1686 | 84.614 | 39.142 | 51.549 | 1.00 | 14.05 |
| 2489 | N | VAL | 1687 | 85.412 | 39.333 | 49.458 | 1.00 | 15.01 |
| 2490 | CA | VAL | 1687 | 85.575 | 40.786 | 49.508 | 1.00 | 15.16 |
| 2491 | CB | VAL | 1687 | 86.997 | 41.223 | 49.052 | 1.00 | 15.36 |
| 2492 | CG1 | VAL | 1687 | 87.290 | 40.797 | 47.611 | 1.00 | 12.78 |
| 2493 | CG2 | VAL | 1687 | 87.155 | 42.702 | 49.214 | 1.00 | 15.07 |
| 2494 | C | VAL | 1687 | 84.500 | 41.372 | 48.588 | 1.00 | 16.77 |
| 2495 | O | VAL | 1687 | 84.556 | 41.212 | 47.372 | 1.00 | 18.75 |
| 2496 | N | LEU | 1688 | 83.500 | 42.017 | 49.174 | 1.00 | 16.57 |
| 2497 | CA | LEU | 1688 | 82.394 | 42.576 | 48.411 | 1.00 | 16.18 |
| 2498 | CB | LEU | 1688 | 81.400 | 43.254 | 49.344 | 1.00 | 15.30 |
| 2499 | CG | LEU | 1688 | 80.742 | 42.326 | 50.369 | 1.00 | 14.41 |
| 2500 | CD1 | LEU | 1688 | 79.737 | 43.122 | 51.173 | 1.00 | 12.70 |
| 2501 | CD2 | LEU | 1688 | 80.083 | 41.142 | 49.672 | 1.00 | 10.09 |
| 2502 | C | LEU | 1688 | 82.737 | 43.502 | 47.260 | 1.00 | 19.55 |
| 2503 | O | LEU | 1688 | 82.047 | 43.504 | 46.243 | 1.00 | 23.25 |
| 2504 | N | SER | 1689 | 83.803 | 44.277 | 47.401 | 1.00 | 23.03 |
| 2505 | CA | SER | 1689 | 84.209 | 45.213 | 46.353 | 1.00 | 21.96 |
| 2506 | CB | SER | 1689 | 84.999 | 46.366 | 46.968 | 1.00 | 21.45 |
| 2507 | OG | SER | 1689 | 86.151 | 45.888 | 47.643 | 1.00 | 24.53 |
| 2508 | C | SER | 1689 | 85.031 | 44.593 | 45.238 | 1.00 | 22.42 |
| 2509 | O | SER | 1689 | 85.306 | 45.252 | 44.239 | 1.00 | 25.52 |
| 2510 | N | GLY | 1690 | 85.430 | 43.337 | 45.409 | 1.00 | 21.46 |
| 2511 | CA | GLY | 1690 | 86.242 | 42.676 | 44.406 | 1.00 | 21.23 |
| 2512 | C | GLY | 1690 | 87.690 | 43.130 | 44.463 | 1.00 | 23.65 |
| 2513 | O | GLY | 1690 | 88.451 | 42.922 | 43.521 | 1.00 | 25.98 |
| 2514 | N | LYS | 1691 | 88.082 | 43.738 | 45.577 | 1.00 | 23.43 |
| 2515 | CA | LYS | 1691 | 89.445 | 44.224 | 45.746 | 1.00 | 23.50 |
| 2516 | CB | LYS | 1691 | 89.561 | 44.980 | 47.067 | 1.00 | 21.39 |
| 2517 | CG | LYS | 1691 | 90.907 | 45.621 | 47.286 | 1.00 | 21.65 |
| 2518 | CD | LYS | 1691 | 90.888 | 46.513 | 48.507 | 1.00 | 22.73 |
| 2519 | CE | LYS | 1691 | 92.193 | 47.269 | 48.654 | 1.00 | 23.13 |
| 2520 | NZ | LYS | 1691 | 92.079 | 48.318 | 49.700 | 1.00 | 27.11 |
| 2521 | C | LYS | 1691 | 90.503 | 43.116 | 45.680 | 1.00 | 24.67 |
| 2522 | O | LYS | 1691 | 90.440 | 42.133 | 46.424 | 1.00 | 26.46 |
| 2523 | N | PRO | 1692 | 91.475 | 43.249 | 44.765 | 1.00 | 25.07 |
| 2524 | CD | PRO | 1692 | 91.517 | 44.246 | 43.682 | 1.00 | 24.13 |
| 2525 | CA | PRO | 1692 | 92.549 | 42.270 | 44.598 | 1.00 | 25.54 |

FIG. 3A-26

| Atom | Atom Type | Resid | # | X | Y | Z | OCC | B |
|---|---|---|---|---|---|---|---|---|
| 2526 | CB | PRO | 1692 | 92.933 | 42.456 | 43.143 | 1.00 | 22.92 |
| 2527 | CG | PRO | 1692 | 92.815 | 43.920 | 42.986 | 1.00 | 23.88 |
| 2528 | C | PRO | 1692 | 93.716 | 42.601 | 45.516 | 1.00 | 27.60 |
| 2529 | O | PRO | 1692 | 93.810 | 43.716 | 46.029 | 1.00 | 29.48 |
| 2530 | N | ALA | 1693 | 94.570 | 41.620 | 45.770 | 1.00 | 31.04 |
| 2531 | CA | ALA | 1693 | 95.736 | 41.833 | 46.621 | 1.00 | 34.86 |
| 2532 | CB | ALA | 1693 | 96.112 | 40.543 | 47.326 | 1.00 | 35.21 |
| 2533 | C | ALA | 1693 | 96.915 | 42.354 | 45.798 | 1.00 | 35.37 |
| 2534 | O | ALA | 1693 | 96.891 | 42.145 | 44.559 | 1.00 | 35.58 | tNS3 COORDINATES (Complex B)

| Atom | Atom Type | Resid | # | X | Y | Z | OCC | B |
|---|---|---|---|---|---|---|---|---|
| 1118 | N | PRO | 1028 | 74.820 | 45.651 | 43.675 | 1.00 | 28.69 |
| 1119 | CD | PRO | 1028 | 75.076 | 44.493 | 44.550 | 1.00 | 28.33 |
| 1120 | CA | PRO | 1028 | 74.869 | 46.897 | 44.441 | 1.00 | 28.80 |
| 1121 | CB | PRO | 1028 | 74.807 | 46.400 | 45.883 | 1.00 | 28.68 |
| 1122 | CG | PRO | 1028 | 75.597 | 45.138 | 45.819 | 1.00 | 27.37 |
| 1123 | C | PRO | 1028 | 76.163 | 47.662 | 44.173 | 1.00 | 28.69 |
| 1124 | O | PRO | 1028 | 77.141 | 47.094 | 43.666 | 1.00 | 30.88 |
| 1125 | N | ILE | 1029 | 76.172 | 48.950 | 44.500 | 1.00 | 25.65 |
| 1126 | CA | ILE | 1029 | 77.359 | 49.763 | 44.288 | 1.00 | 22.21 |
| 1127 | CB | ILE | 1029 | 77.029 | 51.251 | 44.319 | 1.00 | 19.66 |
| 1128 | CG2 | ILE | 1029 | 78.254 | 52.059 | 43.933 | 1.00 | 21.71 |
| 1129 | CG1 | ILE | 1029 | 75.883 | 51.554 | 43.355 | 1.00 | 19.62 |
| 1130 | CD1 | ILE | 1029 | 75.398 | 52.960 | 43.428 | 1.00 | 14.82 |
| 1131 | C | ILE | 1029 | 78.383 | 49.463 | 45.371 | 1.00 | 23.25 |
| 1132 | O | ILE | 1029 | 78.094 | 49.586 | 46.559 | 1.00 | 25.52 |
| 1133 | N | THR | 1030 | 79.561 | 49.023 | 44.951 | 1.00 | 23.20 |
| 1134 | CA | THR | 1030 | 80.651 | 48.725 | 45.860 | 1.00 | 23.22 |
| 1135 | CB | THR | 1030 | 80.916 | 47.207 | 45.958 | 1.00 | 23.28 |
| 1136 | OG1 | THR | 1030 | 81.077 | 46.659 | 44.641 | 1.00 | 27.79 |
| 1137 | CG2 | THR | 1030 | 79.764 | 46.508 | 46.652 | 1.00 | 24.32 |
| 1138 | C | THR | 1030 | 81.879 | 49.406 | 45.277 | 1.00 | 23.10 |
| 1139 | O | THR | 1030 | 81.982 | 49.562 | 44.059 | 1.00 | 24.23 |
| 1140 | N | ALA | 1031 | 82.821 | 49.779 | 46.134 | 1.00 | 20.99 |
| 1141 | CA | ALA | 1031 | 84.024 | 50.456 | 45.675 | 1.00 | 18.06 |
| 1142 | CB | ALA | 1031 | 83.776 | 51.946 | 45.635 | 1.00 | 19.68 |
| 1143 | C | ALA | 1031 | 85.205 | 50.172 | 46.579 | 1.00 | 17.02 |
| 1144 | O | ALA | 1031 | 85.036 | 49.858 | 47.751 | 1.00 | 17.50 |
| 1145 | N | TYR | 1032 | 86.404 | 50.250 | 46.028 | 1.00 | 16.80 |
| 1146 | CA | TYR | 1032 | 87.597 | 50.064 | 46.837 | 1.00 | 18.55 |
| 1147 | CB | TYR | 1032 | 88.127 | 48.633 | 46.786 | 1.00 | 18.83 |
| 1148 | CG | TYR | 1032 | 88.710 | 48.185 | 45.466 | 1.00 | 15.88 |
| 1149 | CD1 | TYR | 1032 | 89.997 | 48.545 | 45.088 | 1.00 | 13.44 |
| 1150 | CE1 | TYR | 1032 | 90.540 | 48.083 | 43.899 | 1.00 | 15.11 |
| 1151 | CD2 | TYR | 1032 | 87.982 | 47.360 | 44.619 | 1.00 | 15.92 |

FIG. 3A-27

| Atom | Atom Type | Resid | # | X | Y | Z | OCC | B |
|---|---|---|---|---|---|---|---|---|
| 1152 | CE2 | TYR | 1032 | 88.514 | 46.893 | 43.436 | 1.00 | 15.01 |
| 1153 | CZ | TYR | 1032 | 89.788 | 47.255 | 43.075 | 1.00 | 15.25 |
| 1154 | OH | TYR | 1032 | 90.298 | 46.766 | 41.894 | 1.00 | 16.61 |
| 1155 | C | TYR | 1032 | 88.645 | 51.045 | 46.368 | 1.00 | 18.69 |
| 1156 | O | TYR | 1032 | 88.632 | 51.462 | 45.211 | 1.00 | 19.25 |
| 1157 | N | ALA | 1033 | 89.525 | 51.443 | 47.274 | 1.00 | 19.62 |
| 1158 | CA | ALA | 1033 | 90.567 | 52.394 | 46.944 | 1.00 | 20.61 |
| 1159 | CB | ALA | 1033 | 90.539 | 53.545 | 47.922 | 1.00 | 18.51 |
| 1160 | C | ALA | 1033 | 91.941 | 51.738 | 46.933 | 1.00 | 22.70 |
| 1161 | O | ALA | 1033 | 92.142 | 50.670 | 47.525 | 1.00 | 24.65 |
| 1162 | N | GLN | 1034 | 92.869 | 52.361 | 46.215 | 1.00 | 23.10 |
| 1163 | CA | GLN | 1034 | 94.236 | 51.880 | 46.120 | 1.00 | 21.69 |
| 1164 | CB | GLN | 1034 | 94.432 | 50.971 | 44.899 | 1.00 | 22.35 |
| 1165 | CG | GLN | 1034 | 93.643 | 49.679 | 44.895 | 1.00 | 23.27 |
| 1166 | CD | GLN | 1034 | 93.927 | 48.834 | 43.666 | 1.00 | 26.53 |
| 1167 | OE1 | GLN | 1034 | 93.982 | 49.341 | 42.544 | 1.00 | 27.77 |
| 1168 | NE2 | GLN | 1034 | 94.119 | 47.537 | 43.872 | 1.00 | 27.16 |
| 1169 | C | GLN | 1034 | 95.111 | 53.103 | 45.955 | 1.00 | 22.49 |
| 1170 | O | GLN | 1034 | 94.780 | 54.005 | 45.186 | 1.00 | 21.85 |
| 1171 | N | GLN | 1035 | 96.194 | 53.156 | 46.722 | 1.00 | 25.39 |
| 1172 | CA | GLN | 1035 | 97.151 | 54.253 | 46.648 | 1.00 | 26.92 |
| 1173 | CB | GLN | 1035 | 97.779 | 54.498 | 48.013 | 1.00 | 29.66 |
| 1174 | CG | GLN | 1035 | 98.985 | 55.414 | 47.971 | 1.00 | 37.10 |
| 1175 | CD | GLN | 1035 | 98.983 | 56.413 | 49.112 | 1.00 | 43.12 |
| 1176 | OE1 | GLN | 1035 | 98.743 | 56.056 | 50.271 | 1.00 | 44.84 |
| 1177 | NE2 | GLN | 1035 | 99.238 | 57.678 | 48.790 | 1.00 | 45.69 |
| 1178 | C | GLN | 1035 | 98.234 | 53.851 | 45.655 | 1.00 | 27.03 |
| 1179 | O | GLN | 1035 | 98.750 | 52.741 | 45.726 | 1.00 | 29.15 |
| 1180 | N | THR | 1036 | 98.582 | 54.745 | 44.738 | 1.00 | 26.03 |
| 1181 | CA | THR | 1036 | 99.584 | 54.437 | 43.735 | 1.00 | 25.05 |
| 1182 | CB | THR | 1036 | 99.094 | 54.813 | 42.363 | 1.00 | 24.90 |
| 1183 | OG1 | THR | 1036 | 98.718 | 56.192 | 42.375 | 1.00 | 25.74 |
| 1184 | CG2 | THR | 1036 | 97.901 | 53.967 | 41.988 | 1.00 | 23.85 |
| 1185 | C | THR | 1036 | 100.911 | 55.131 | 43.976 | 1.00 | 26.04 |
| 1186 | O | THR | 1036 | 101.933 | 54.712 | 43.427 | 1.00 | 27.67 |
| 1187 | N | ARG | 1037 | 100.895 | 56.232 | 44.719 | 1.00 | 25.73 |
| 1188 | CA | ARG | 1037 | 102.137 | 56.928 | 45.023 | 1.00 | 25.76 |
| 1189 | CB | ARG | 1037 | 102.596 | 57.805 | 43.873 | 1.00 | 25.31 |
| 1190 | CG | ARG | 1037 | 101.623 | 58.844 | 43.446 | 1.00 | 27.06 |
| 1191 | CD | ARG | 1037 | 102.326 | 59.847 | 42.575 | 1.00 | 27.29 |
| 1192 | NE | ARG | 1037 | 103.303 | 59.215 | 41.696 | 1.00 | 25.59 |
| 1193 | CZ | ARG | 1037 | 103.077 | 58.933 | 40.421 | 1.00 | 27.51 |
| 1194 | NH1 | ARG | 1037 | 101.893 | 59.223 | 39.877 | 1.00 | 27.27 |
| 1195 | NH2 | ARG | 1037 | 104.048 | 58.402 | 39.685 | 1.00 | 23.57 |
| 1196 | C | ARG | 1037 | 102.088 | 57.727 | 46.303 | 1.00 | 26.18 |
| 1197 | O | ARG | 1037 | 101.011 | 58.021 | 46.813 | 1.00 | 26.32 |
| 1198 | N | GLY | 1038 | 103.266 | 58.059 | 46.823 | 1.00 | 26.76 |
| 1199 | CA | GLY | 1038 | 103.348 | 58.806 | 48.064 | 1.00 | 28.78 |
| 1200 | C | GLY | 1038 | 103.715 | 60.268 | 47.914 | 1.00 | 29.65 |

FIG. 3A-28

| Atom | Atom Type | Resid | # | X | Y | Z | OCC | B |
|---|---|---|---|---|---|---|---|---|
| 1201 | O | GLY | 1038 | 103.913 | 60.769 | 46.805 | 1.00 | 30.89 |
| 1202 | N | LEU | 1039 | 103.865 | 60.929 | 49.054 | 1.00 | 29.52 |
| 1203 | CA | LEU | 1039 | 104.199 | 62.346 | 49.135 | 1.00 | 30.82 |
| 1204 | CB | LEU | 1039 | 104.550 | 62.670 | 50.582 | 1.00 | 34.94 |
| 1205 | CG | LEU | 1039 | 104.045 | 63.977 | 51.184 | 1.00 | 39.14 |
| 1206 | CD1 | LEU | 1039 | 103.634 | 63.744 | 52.648 | 1.00 | 41.57 |
| 1207 | CD2 | LEU | 1039 | 105.127 | 65.038 | 51.079 | 1.00 | 41.24 |
| 1208 | C | LEU | 1039 | 105.342 | 62.782 | 48.214 | 1.00 | 30.11 |
| 1209 | O | LEU | 1039 | 105.161 | 63.647 | 47.354 | 1.00 | 29.71 |
| 1210 | N | LEU | 1040 | 106.495 | 62.136 | 48.358 | 1.00 | 28.91 |
| 1211 | CA | LEU | 1040 | 107.676 | 62.463 | 47.568 | 1.00 | 27.58 |
| 1212 | CB | LEU | 1040 | 108.878 | 61.685 | 48.098 | 1.00 | 28.69 |
| 1213 | CG | LEU | 1040 | 110.213 | 62.413 | 47.959 | 1.00 | 30.89 |
| 1214 | CD1 | LEU | 1040 | 110.195 | 63.632 | 48.870 | 1.00 | 32.42 |
| 1215 | CD2 | LEU | 1040 | 111.358 | 61.492 | 48.325 | 1.00 | 30.06 |
| 1216 | C | LEU | 1040 | 107.524 | 62.221 | 46.061 | 1.00 | 26.74 |
| 1217 | O | LEU | 1040 | 107.899 | 63.068 | 45.242 | 1.00 | 28.09 |
| 1218 | N | GLY | 1041 | 106.994 | 61.062 | 45.695 | 1.00 | 24.50 |
| 1219 | CA | GLY | 1041 | 106.813 | 60.750 | 44.291 | 1.00 | 23.28 |
| 1220 | C | GLY | 1041 | 105.798 | 61.679 | 43.667 | 1.00 | 23.92 |
| 1221 | O | GLY | 1041 | 105.922 | 62.054 | 42.498 | 1.00 | 22.23 |
| 1222 | N | CYS | 1042 | 104.788 | 62.050 | 44.449 | 1.00 | 23.15 |
| 1223 | CA | CYS | 1042 | 103.751 | 62.955 | 43.981 | 1.00 | 23.53 |
| 1224 | CB | CYS | 1042 | 102.688 | 63.138 | 45.060 | 1.00 | 25.84 |
| 1225 | SG | CYS | 1042 | 101.422 | 64.376 | 44.680 | 1.00 | 27.73 |
| 1226 | C | CYS | 1042 | 104.398 | 64.289 | 43.627 | 1.00 | 23.74 |
| 1227 | O | CYS | 1042 | 104.253 | 64.771 | 42.507 | 1.00 | 25.62 |
| 1228 | N | ILE | 1043 | 105.183 | 64.835 | 44.555 | 1.00 | 23.35 |
| 1229 | CA | ILE | 1043 | 105.878 | 66.110 | 44.350 | 1.00 | 20.45 |
| 1230 | CB | ILE | 1043 | 106.720 | 66.484 | 45.593 | 1.00 | 20.32 |
| 1231 | CG2 | ILE | 1043 | 107.437 | 67.810 | 45.373 | 1.00 | 20.94 |
| 1232 | CG1 | ILE | 1043 | 105.815 | 66.571 | 46.831 | 1.00 | 18.68 |
| 1233 | CD1 | ILE | 1043 | 106.557 | 66.802 | 48.145 | 1.00 | 18.48 |
| 1234 | C | ILE | 1043 | 106.765 | 66.086 | 43.103 | 1.00 | 20.27 |
| 1235 | O | ILE | 1043 | 106.645 | 66.952 | 42.242 | 1.00 | 23.53 |
| 1236 | N | ILE | 1044 | 107.622 | 65.077 | 42.981 | 1.00 | 20.30 |
| 1237 | CA | ILE | 1044 | 108.502 | 64.965 | 41.817 | 1.00 | 19.23 |
| 1238 | CB | ILE | 1044 | 109.370 | 63.680 | 41.878 | 1.00 | 18.89 |
| 1239 | CG2 | ILE | 1044 | 110.205 | 63.532 | 40.616 | 1.00 | 15.12 |
| 1240 | CG1 | ILE | 1044 | 110.276 | 63.720 | 43.108 | 1.00 | 17.13 |
| 1241 | CD1 | ILE | 1044 | 110.979 | 62.422 | 43.383 | 1.00 | 19.28 |
| 1242 | C | ILE | 1044 | 107.673 | 64.942 | 40.541 | 1.00 | 20.68 |
| 1243 | O | ILE | 1044 | 107.921 | 65.721 | 39.621 | 1.00 | 21.41 |
| 1244 | N | THR | 1045 | 106.647 | 64.094 | 40.513 | 1.00 | 23.02 |
| 1245 | CA | THR | 1045 | 105.779 | 63.968 | 39.340 | 1.00 | 22.82 |
| 1246 | CB | THR | 1045 | 104.744 | 62.848 | 39.515 | 1.00 | 22.67 |
| 1247 | OG1 | THR | 1045 | 105.415 | 61.631 | 39.874 | 1.00 | 23.02 |
| 1248 | CG2 | THR | 1045 | 103.985 | 62.630 | 38.219 | 1.00 | 21.21 |
| 1249 | C | THR | 1045 | 105.044 | 65.260 | 39.055 | 1.00 | 23.69 |

FIG. 3A-29

| Atom | Atom Type | Resid | # | X | Y | Z | OCC | B |
|---|---|---|---|---|---|---|---|---|
| 1250 | O | THR | 1045 | 104.773 | 65.583 | 37.903 | 1.00 | 26.48 |
| 1251 | N | SER | 1046 | 104.750 | 66.013 | 40.106 | 1.00 | 23.58 |
| 1252 | CA | SER | 1046 | 104.043 | 67.273 | 39.960 | 1.00 | 24.58 |
| 1253 | CB | SER | 1046 | 103.691 | 67.852 | 41.331 | 1.00 | 25.34 |
| 1254 | OG | SER | 1046 | 102.926 | 69.034 | 41.195 | 1.00 | 26.40 |
| 1255 | C | SER | 1046 | 104.895 | 68.264 | 39.205 | 1.00 | 25.37 |
| 1256 | O | SER | 1046 | 104.397 | 69.000 | 38.355 | 1.00 | 25.66 |
| 1257 | N | LEU | 1047 | 106.183 | 68.281 | 39.521 | 1.00 | 25.73 |
| 1258 | CA | LEU | 1047 | 107.094 | 69.204 | 38.873 | 1.00 | 26.65 |
| 1259 | CB | LEU | 1047 | 108.316 | 69.450 | 39.759 | 1.00 | 26.72 |
| 1260 | CG | LEU | 1047 | 107.985 | 69.811 | 41.217 | 1.00 | 26.90 |
| 1261 | CD1 | LEU | 1047 | 109.237 | 70.265 | 41.944 | 1.00 | 25.51 |
| 1262 | CD2 | LEU | 1047 | 106.920 | 70.890 | 41.284 | 1.00 | 26.82 |
| 1263 | C | LEU | 1047 | 107.494 | 68.762 | 37.466 | 1.00 | 27.72 |
| 1264 | O | LEU | 1047 | 107.461 | 69.561 | 36.535 | 1.00 | 29.56 |
| 1265 | N | THR | 1048 | 107.806 | 67.483 | 37.288 | 1.00 | 28.48 |
| 1266 | CA | THR | 1048 | 108.203 | 66.992 | 35.968 | 1.00 | 27.84 |
| 1267 | CB | THR | 1048 | 108.815 | 65.591 | 36.046 | 1.00 | 26.24 |
| 1268 | OG1 | THR | 1048 | 107.818 | 64.666 | 36.495 | 1.00 | 28.13 |
| 1269 | CG2 | THR | 1048 | 110.002 | 65.580 | 37.001 | 1.00 | 23.61 |
| 1270 | C | THR | 1048 | 107.022 | 66.936 | 35.008 | 1.00 | 28.29 |
| 1271 | O | THR | 1048 | 107.167 | 67.168 | 33.802 | 1.00 | 28.96 |
| 1272 | N | GLY | 1049 | 105.860 | 66.592 | 35.553 | 1.00 | 29.55 |
| 1273 | CA | GLY | 1049 | 104.652 | 66.490 | 34.759 | 1.00 | 28.26 |
| 1274 | C | GLY | 1049 | 104.582 | 65.197 | 33.975 | 1.00 | 28.82 |
| 1275 | O | GLY | 1049 | 103.734 | 65.051 | 33.096 | 1.00 | 27.69 |
| 1276 | N | ARG | 1050 | 105.447 | 64.242 | 34.304 | 1.00 | 29.15 |
| 1277 | CA | ARG | 1050 | 105.464 | 62.968 | 33.595 | 1.00 | 30.31 |
| 1278 | CB | ARG | 1050 | 106.852 | 62.709 | 33.002 | 1.00 | 32.91 |
| 1279 | CG | ARG | 1050 | 106.864 | 61.866 | 31.728 | 1.00 | 39.62 |
| 1280 | CD | ARG | 1050 | 108.295 | 61.494 | 31.320 | 1.00 | 46.14 |
| 1281 | NE | ARG | 1050 | 108.577 | 60.054 | 31.442 | 1.00 | 52.84 |
| 1282 | CZ | ARG | 1050 | 109.518 | 59.516 | 32.227 | 1.00 | 55.48 |
| 1283 | NH1 | ARG | 1050 | 110.290 | 60.283 | 32.990 | 1.00 | 58.74 |
| 1284 | NH2 | ARG | 1050 | 109.730 | 58.204 | 32.208 | 1.00 | 55.47 |
| 1285 | C | ARG | 1050 | 105.085 | 61.875 | 34.586 | 1.00 | 29.07 |
| 1286 | O | ARG | 1050 | 105.691 | 61.751 | 35.643 | 1.00 | 29.25 |
| 1287 | N | ASP | 1051 | 104.040 | 61.123 | 34.267 | 1.00 | 28.54 |
| 1288 | CA | ASP | 1051 | 103.572 | 60.054 | 35.133 | 1.00 | 27.21 |
| 1289 | CB | ASP | 1051 | 102.214 | 60.412 | 35.729 | 1.00 | 28.72 |
| 1290 | CG | ASP | 1051 | 101.694 | 59.357 | 36.684 | 1.00 | 27.51 |
| 1291 | OD1 | ASP | 1051 | 102.495 | 58.544 | 37.189 | 1.00 | 29.23 |
| 1292 | OD2 | ASP | 1051 | 100.478 | 59.354 | 36.941 | 1.00 | 27.37 |
| 1293 | C | ASP | 1051 | 103.446 | 58.790 | 34.320 | 1.00 | 28.42 |
| 1294 | O | ASP | 1051 | 102.531 | 58.658 | 33.513 | 1.00 | 29.82 |
| 1295 | N | LYS | 1052 | 104.359 | 57.857 | 34.551 | 1.00 | 29.39 |
| 1296 | CA | LYS | 1052 | 104.369 | 56.596 | 33.830 | 1.00 | 30.29 |
| 1297 | CB | LYS | 1052 | 105.808 | 56.117 | 33.647 | 1.00 | 32.22 |
| 1298 | CG | LYS | 1052 | 106.598 | 56.878 | 32.577 | 1.00 | 35.28 |

FIG. 3A-30

| Atom | Atom Type | Resid | # | X | Y | Z | OCC | B |
|---|---|---|---|---|---|---|---|---|
| 1299 | CD | LYS | 1052 | 106.059 | 56.579 | 31.175 | 1.00 | 38.64 |
| 1300 | CE | LYS | 1052 | 106.089 | 55.073 | 30.869 | 1.00 | 41.17 |
| 1301 | NZ | LYS | 1052 | 105.403 | 54.714 | 29.588 | 1.00 | 42.32 |
| 1302 | C | LYS | 1052 | 103.512 | 55.485 | 34.447 | 1.00 | 31.22 |
| 1303 | O | LYS | 1052 | 103.356 | 54.424 | 33.841 | 1.00 | 33.64 |
| 1304 | N | ASN | 1053 | 102.965 | 55.718 | 35.641 | 1.00 | 29.10 |
| 1305 | CA | ASN | 1053 | 102.123 | 54.718 | 36.301 | 1.00 | 26.26 |
| 1306 | CB | ASN | 1053 | 101.581 | 55.233 | 37.631 | 1.00 | 25.64 |
| 1307 | CG | ASN | 1053 | 102.609 | 55.207 | 38.727 | 1.00 | 23.95 |
| 1308 | OD1 | ASN | 1053 | 103.801 | 55.064 | 38.468 | 1.00 | 26.76 |
| 1309 | ND2 | ASN | 1053 | 102.161 | 55.363 | 39.963 | 1.00 | 22.69 |
| 1310 | C | ASN | 1053 | 100.942 | 54.380 | 35.427 | 1.00 | 26.87 |
| 1311 | O | ASN | 1053 | 100.483 | 55.222 | 34.649 | 1.00 | 26.93 |
| 1312 | N | ALA | 1054 | 100.457 | 53.147 | 35.545 | 1.00 | 27.34 |
| 1313 | CA | ALA | 1054 | 99.301 | 52.713 | 34.766 | 1.00 | 27.38 |
| 1314 | CB | ALA | 1054 | 99.275 | 51.196 | 34.623 | 1.00 | 29.92 |
| 1315 | C | ALA | 1054 | 98.056 | 53.200 | 35.487 | 1.00 | 26.71 |
| 1316 | O | ALA | 1054 | 98.049 | 53.329 | 36.720 | 1.00 | 26.64 |
| 1317 | N | VAL | 1055 | 97.009 | 53.474 | 34.716 | 1.00 | 25.91 |
| 1318 | CA | VAL | 1055 | 95.761 | 53.978 | 35.269 | 1.00 | 24.92 |
| 1319 | CB | VAL | 1055 | 95.262 | 55.216 | 34.476 | 1.00 | 22.35 |
| 1320 | CG1 | VAL | 1055 | 93.954 | 55.731 | 35.052 | 1.00 | 22.08 |
| 1321 | CG2 | VAL | 1055 | 96.296 | 56.310 | 34.517 | 1.00 | 20.14 |
| 1322 | C | VAL | 1055 | 94.681 | 52.908 | 35.257 | 1.00 | 24.94 |
| 1323 | O | VAL | 1055 | 94.641 | 52.064 | 34.367 | 1.00 | 24.51 |
| 1324 | N | GLU | 1056 | 93.826 | 52.938 | 36.269 | 1.00 | 25.14 |
| 1325 | CA | GLU | 1056 | 92.720 | 52.008 | 36.377 | 1.00 | 25.82 |
| 1326 | CB | GLU | 1056 | 93.123 | 50.767 | 37.163 | 1.00 | 28.83 |
| 1327 | CG | GLU | 1056 | 93.973 | 49.772 | 36.406 | 1.00 | 36.03 |
| 1328 | CD | GLU | 1056 | 93.831 | 48.360 | 36.961 | 1.00 | 42.08 |
| 1329 | OE1 | GLU | 1056 | 93.640 | 48.210 | 38.191 | 1.00 | 43.57 |
| 1330 | OE2 | GLU | 1056 | 93.889 | 47.398 | 36.159 | 1.00 | 46.03 |
| 1331 | C | GLU | 1056 | 91.614 | 52.702 | 37.131 | 1.00 | 24.57 |
| 1332 | O | GLU | 1056 | 91.856 | 53.700 | 37.810 | 1.00 | 26.39 |
| 1333 | N | GLY | 1057 | 90.399 | 52.189 | 37.006 | 1.00 | 22.01 |
| 1334 | CA | GLY | 1057 | 89.293 | 52.773 | 37.737 | 1.00 | 20.85 |
| 1335 | C | GLY | 1057 | 88.552 | 53.902 | 37.067 | 1.00 | 19.15 |
| 1336 | O | GLY | 1057 | 89.013 | 54.476 | 36.079 | 1.00 | 19.49 |
| 1337 | N | GLU | 1058 | 87.385 | 54.203 | 37.631 | 1.00 | 19.23 |
| 1338 | CA | GLU | 1058 | 86.479 | 55.239 | 37.141 | 1.00 | 16.31 |
| 1339 | CB | GLU | 1058 | 85.026 | 54.871 | 37.479 | 1.00 | 15.32 |
| 1340 | CG | GLU | 1058 | 84.457 | 53.613 | 36.792 | 1.00 | 15.36 |
| 1341 | CD | GLU | 1058 | 85.101 | 52.303 | 37.238 | 1.00 | 18.10 |
| 1342 | OE1 | GLU | 1058 | 85.591 | 52.192 | 38.377 | 1.00 | 20.29 |
| 1343 | OE2 | GLU | 1058 | 85.118 | 51.359 | 36.434 | 1.00 | 24.06 |
| 1344 | C | GLU | 1058 | 86.804 | 56.561 | 37.803 | 1.00 | 15.32 |
| 1345 | O | GLU | 1058 | 86.610 | 57.623 | 37.224 | 1.00 | 15.89 |
| 1346 | N | VAL | 1059 | 87.292 | 56.485 | 39.034 | 1.00 | 14.97 |
| 1347 | CA | VAL | 1059 | 87.629 | 57.661 | 39.818 | 1.00 | 12.63 |

FIG. 3A-31

| Atom | Atom Type | Resid | # | X | Y | Z | OCC | B |
|---|---|---|---|---|---|---|---|---|
| 1348 | CB | VAL | 1059 | 86.813 | 57.684 | 41.136 | 1.00 | 9.72 |
| 1349 | CG1 | VAL | 1059 | 86.972 | 59.015 | 41.839 | 1.00 | 10.00 |
| 1350 | CG2 | VAL | 1059 | 85.345 | 57.395 | 40.862 | 1.00 | 7.03 |
| 1351 | C | VAL | 1059 | 89.121 | 57.661 | 40.156 | 1.00 | 14.78 |
| 1352 | O | VAL | 1059 | 89.656 | 56.673 | 40.648 | 1.00 | 15.26 |
| 1353 | N | GLN | 1060 | 89.796 | 58.759 | 39.845 | 1.00 | 16.52 |
| 1354 | CA | GLN | 1060 | 91.212 | 58.894 | 40.140 | 1.00 | 16.47 |
| 1355 | CB | GLN | 1060 | 91.936 | 59.556 | 38.967 | 1.00 | 15.66 |
| 1356 | CG | GLN | 1060 | 91.816 | 58.816 | 37.670 | 1.00 | 17.53 |
| 1357 | CD | GLN | 1060 | 92.215 | 57.361 | 37.809 | 1.00 | 20.63 |
| 1358 | OE1 | GLN | 1060 | 93.215 | 57.037 | 38.448 | 1.00 | 22.69 |
| 1359 | NE2 | GLN | 1060 | 91.424 | 56.474 | 37.229 | 1.00 | 22.24 |
| 1360 | C | GLN | 1060 | 91.367 | 59.775 | 41.372 | 1.00 | 18.64 |
| 1361 | O | GLN | 1060 | 90.702 | 60.801 | 41.496 | 1.00 | 21.76 |
| 1362 | N | ILE | 1061 | 92.175 | 59.345 | 42.326 | 1.00 | 19.32 |
| 1363 | CA | ILE | 1061 | 92.410 | 60.171 | 43.499 | 1.00 | 19.78 |
| 1364 | CB | ILE | 1061 | 92.838 | 59.329 | 44.718 | 1.00 | 18.89 |
| 1365 | CG2 | ILE | 1061 | 93.064 | 60.225 | 45.926 | 1.00 | 18.02 |
| 1366 | CG1 | ILE | 1061 | 91.759 | 58.289 | 45.033 | 1.00 | 16.75 |
| 1367 | CD1 | ILE | 1061 | 92.138 | 57.352 | 46.120 | 1.00 | 14.36 |
| 1368 | C | ILE | 1061 | 93.552 | 61.068 | 43.030 | 1.00 | 21.51 |
| 1369 | O | ILE | 1061 | 94.615 | 60.579 | 42.626 | 1.00 | 22.71 |
| 1370 | N | VAL | 1062 | 93.305 | 62.370 | 42.979 | 1.00 | 21.91 |
| 1371 | CA | VAL | 1062 | 94.321 | 63.294 | 42.515 | 1.00 | 19.92 |
| 1372 | CB | VAL | 1062 | 93.858 | 64.075 | 41.278 | 1.00 | 18.17 |
| 1373 | CG1 | VAL | 1062 | 93.500 | 63.117 | 40.166 | 1.00 | 15.34 |
| 1374 | CG2 | VAL | 1062 | 92.692 | 64.977 | 41.622 | 1.00 | 15.73 |
| 1375 | C | VAL | 1062 | 94.776 | 64.252 | 43.588 | 1.00 | 21.02 |
| 1376 | O | VAL | 1062 | 94.099 | 64.449 | 44.593 | 1.00 | 22.09 |
| 1377 | N | SER | 1063 | 95.937 | 64.850 | 43.367 | 1.00 | 22.93 |
| 1378 | CA | SER | 1063 | 96.500 | 65.776 | 44.324 | 1.00 | 23.94 |
| 1379 | CB | SER | 1063 | 97.290 | 64.996 | 45.370 | 1.00 | 25.73 |
| 1380 | OG | SER | 1063 | 97.794 | 65.862 | 46.369 | 1.00 | 32.24 |
| 1381 | C | SER | 1063 | 97.413 | 66.795 | 43.673 | 1.00 | 23.42 |
| 1382 | O | SER | 1063 | 97.944 | 66.587 | 42.578 | 1.00 | 20.31 |
| 1383 | N | THR | 1064 | 97.587 | 67.897 | 44.382 | 1.00 | 26.57 |
| 1384 | CA | THR | 1064 | 98.446 | 69.005 | 43.978 | 1.00 | 29.88 |
| 1385 | CB | THR | 1064 | 97.629 | 70.305 | 43.763 | 1.00 | 27.45 |
| 1386 | OG1 | THR | 1064 | 97.036 | 70.707 | 45.004 | 1.00 | 25.21 |
| 1387 | CG2 | THR | 1064 | 96.523 | 70.086 | 42.751 | 1.00 | 26.09 |
| 1388 | C | THR | 1064 | 99.358 | 69.202 | 45.194 | 1.00 | 32.85 |
| 1389 | O | THR | 1064 | 99.408 | 68.350 | 46.086 | 1.00 | 34.87 |
| 1390 | N | ALA | 1065 | 100.055 | 70.326 | 45.252 | 1.00 | 35.39 |
| 1391 | CA | ALA | 1065 | 100.924 | 70.604 | 46.388 | 1.00 | 35.88 |
| 1392 | CB | ALA | 1065 | 101.866 | 71.747 | 46.051 | 1.00 | 37.88 |
| 1393 | C | ALA | 1065 | 100.052 | 70.978 | 47.578 | 1.00 | 35.60 |
| 1394 | O | ALA | 1065 | 100.275 | 70.537 | 48.698 | 1.00 | 35.43 |
| 1395 | N | THR | 1066 | 99.028 | 71.772 | 47.307 | 1.00 | 36.74 |
| 1396 | CA | THR | 1066 | 98.119 | 72.240 | 48.339 | 1.00 | 37.72 |

FIG. 3A-32

| Atom | Atom Type | Resid | # | X | Y | Z | OCC | B |
|---|---|---|---|---|---|---|---|---|
| 1397 | CB | THR | 1066 | 97.434 | 73.583 | 47.895 | 1.00 | 39.54 |
| 1398 | OG1 | THR | 1066 | 96.431 | 73.973 | 48.844 | 1.00 | 41.76 |
| 1399 | CG2 | THR | 1066 | 96.792 | 73.444 | 46.514 | 1.00 | 40.92 |
| 1400 | C | THR | 1066 | 97.043 | 71.261 | 48.808 | 1.00 | 36.34 |
| 1401 | O | THR | 1066 | 96.641 | 71.307 | 49.975 | 1.00 | 36.42 |
| 1402 | N | GLN | 1067 | 96.608 | 70.340 | 47.952 | 1.00 | 34.64 |
| 1403 | CA | GLN | 1067 | 95.517 | 69.461 | 48.367 | 1.00 | 34.70 |
| 1404 | CB | GLN | 1067 | 94.235 | 70.290 | 48.381 | 1.00 | 36.42 |
| 1405 | CG | GLN | 1067 | 93.980 | 70.953 | 47.033 | 1.00 | 40.18 |
| 1406 | CD | GLN | 1067 | 92.844 | 71.952 | 47.052 | 1.00 | 42.84 |
| 1407 | OE1 | GLN | 1067 | 91.783 | 71.704 | 47.632 | 1.00 | 44.48 |
| 1408 | NE2 | GLN | 1067 | 93.048 | 73.080 | 46.383 | 1.00 | 45.42 |
| 1409 | C | GLN | 1067 | 95.263 | 68.210 | 47.536 | 1.00 | 32.18 |
| 1410 | O | GLN | 1067 | 95.813 | 68.051 | 46.449 | 1.00 | 32.90 |
| 1411 | N | THR | 1068 | 94.379 | 67.357 | 48.054 | 1.00 | 29.91 |
| 1412 | CA | THR | 1068 | 93.972 | 66.108 | 47.413 | 1.00 | 27.99 |
| 1413 | CB | THR | 1068 | 94.296 | 64.860 | 48.291 | 1.00 | 28.36 |
| 1414 | OG1 | THR | 1068 | 95.710 | 64.751 | 48.488 | 1.00 | 30.82 |
| 1415 | CG2 | THR | 1068 | 93.788 | 63.581 | 47.636 | 1.00 | 26.64 |
| 1416 | C | THR | 1068 | 92.460 | 66.158 | 47.248 | 1.00 | 25.47 |
| 1417 | O | THR | 1068 | 91.745 | 66.644 | 48.126 | 1.00 | 25.64 |
| 1418 | N | PHE | 1069 | 91.988 | 65.670 | 46.112 | 1.00 | 23.13 |
| 1419 | CA | PHE | 1069 | 90.565 | 65.621 | 45.801 | 1.00 | 20.30 |
| 1420 | CB | PHE | 1069 | 90.060 | 66.960 | 45.222 | 1.00 | 19.44 |
| 1421 | CG | PHE | 1069 | 91.012 | 67.618 | 44.258 | 1.00 | 18.91 |
| 1422 | CD1 | PHE | 1069 | 90.765 | 67.593 | 42.890 | 1.00 | 16.69 |
| 1423 | CD2 | PHE | 1069 | 92.174 | 68.237 | 44.720 | 1.00 | 16.99 |
| 1424 | CE1 | PHE | 1069 | 91.663 | 68.165 | 41.998 | 1.00 | 17.12 |
| 1425 | CE2 | PHE | 1069 | 93.075 | 68.811 | 43.838 | 1.00 | 15.95 |
| 1426 | CZ | PHE | 1069 | 92.822 | 68.775 | 42.475 | 1.00 | 17.86 |
| 1427 | C | PHE | 1069 | 90.340 | 64.454 | 44.840 | 1.00 | 19.50 |
| 1428 | O | PHE | 1069 | 91.216 | 63.590 | 44.687 | 1.00 | 18.25 |
| 1429 | N | LEU | 1070 | 89.171 | 64.402 | 44.216 | 1.00 | 17.14 |
| 1430 | CA | LEU | 1070 | 88.872 | 63.320 | 43.297 | 1.00 | 16.12 |
| 1431 | CB | LEU | 1070 | 87.699 | 62.499 | 43.806 | 1.00 | 15.63 |
| 1432 | CG | LEU | 1070 | 87.908 | 61.837 | 45.157 | 1.00 | 13.76 |
| 1433 | CD1 | LEU | 1070 | 86.650 | 61.104 | 45.531 | 1.00 | 16.70 |
| 1434 | CD2 | LEU | 1070 | 89.072 | 60.890 | 45.082 | 1.00 | 15.02 |
| 1435 | C | LEU | 1070 | 88.545 | 63.848 | 41.926 | 1.00 | 16.35 |
| 1436 | O | LEU | 1070 | 88.181 | 65.011 | 41.774 | 1.00 | 18.69 |
| 1437 | N | ALA | 1071 | 88.703 | 62.989 | 40.929 | 1.00 | 15.91 |
| 1438 | CA | ALA | 1071 | 88.417 | 63.323 | 39.544 | 1.00 | 15.63 |
| 1439 | CB | ALA | 1071 | 89.701 | 63.547 | 38.773 | 1.00 | 14.74 |
| 1440 | C | ALA | 1071 | 87.717 | 62.086 | 39.050 | 1.00 | 16.11 |
| 1441 | O | ALA | 1071 | 88.194 | 60.981 | 39.278 | 1.00 | 16.97 |
| 1442 | N | THR | 1072 | 86.572 | 62.273 | 38.410 | 1.00 | 17.64 |
| 1443 | CA | THR | 1072 | 85.764 | 61.171 | 37.914 | 1.00 | 15.73 |
| 1444 | CB | THR | 1072 | 84.329 | 61.312 | 38.416 | 1.00 | 15.97 |
| 1445 | OG1 | THR | 1072 | 84.344 | 61.551 | 39.827 | 1.00 | 18.30 |

FIG. 3A-33

| Atom | Atom Type | Resid | # | X | Y | Z | OCC | B |
|---|---|---|---|---|---|---|---|---|
| 1446 | CG2 | THR | 1072 | 83.539 | 60.052 | 38.134 | 1.00 | 18.15 |
| 1447 | C | THR | 1072 | 85.725 | 61.166 | 36.405 | 1.00 | 14.68 |
| 1448 | O | THR | 1072 | 85.511 | 62.197 | 35.786 | 1.00 | 16.38 |
| 1449 | N | CYS | 1073 | 85.890 | 59.998 | 35.808 | 1.00 | 14.37 |
| 1450 | CA | CYS | 1073 | 85.856 | 59.895 | 34.364 | 1.00 | 15.72 |
| 1451 | CB | CYS | 1073 | 86.814 | 58.807 | 33.889 | 1.00 | 17.69 |
| 1452 | SG | CYS | 1073 | 88.536 | 59.069 | 34.384 | 1.00 | 23.22 |
| 1453 | C | CYS | 1073 | 84.450 | 59.591 | 33.878 | 1.00 | 16.21 |
| 1454 | O | CYS | 1073 | 83.850 | 58.601 | 34.286 | 1.00 | 15.04 |
| 1455 | N | ILE | 1074 | 83.907 | 60.472 | 33.044 | 1.00 | 17.51 |
| 1456 | CA | ILE | 1074 | 82.578 | 60.294 | 32.475 | 1.00 | 20.31 |
| 1457 | CB | ILE | 1074 | 81.560 | 61.315 | 33.050 | 1.00 | 20.77 |
| 1458 | CG2 | ILE | 1074 | 80.171 | 61.053 | 32.472 | 1.00 | 20.99 |
| 1459 | CG1 | ILE | 1074 | 81.509 | 61.221 | 34.580 | 1.00 | 19.74 |
| 1460 | CD1 | ILE | 1074 | 80.686 | 62.297 | 35.259 | 1.00 | 16.17 |
| 1461 | C | ILE | 1074 | 82.716 | 60.504 | 30.963 | 1.00 | 24.53 |
| 1462 | O | ILE | 1074 | 83.299 | 61.493 | 30.521 | 1.00 | 28.24 |
| 1463 | N | ASN | 1075 | 82.236 | 59.543 | 30.176 | 1.00 | 27.13 |
| 1464 | CA | ASN | 1075 | 82.297 | 59.601 | 28.708 | 1.00 | 25.19 |
| 1465 | CB | ASN | 1075 | 81.193 | 60.502 | 28.146 | 1.00 | 24.15 |
| 1466 | CG | ASN | 1075 | 79.836 | 59.845 | 28.180 | 1.00 | 20.59 |
| 1467 | OD1 | ASN | 1075 | 79.635 | 58.844 | 28.858 | 1.00 | 22.02 |
| 1468 | ND2 | ASN | 1075 | 78.894 | 60.406 | 27.453 | 1.00 | 23.38 |
| 1469 | C | ASN | 1075 | 83.642 | 59.983 | 28.092 | 1.00 | 26.07 |
| 1470 | O | ASN | 1075 | 83.707 | 60.798 | 27.164 | 1.00 | 29.28 |
| 1471 | N | GLY | 1076 | 84.718 | 59.394 | 28.602 | 1.00 | 26.05 |
| 1472 | CA | GLY | 1076 | 86.040 | 59.670 | 28.059 | 1.00 | 23.82 |
| 1473 | C | GLY | 1076 | 86.737 | 60.935 | 28.512 | 1.00 | 22.44 |
| 1474 | O | GLY | 1076 | 87.779 | 61.292 | 27.959 | 1.00 | 23.12 |
| 1475 | N | VAL | 1077 | 86.202 | 61.595 | 29.534 | 1.00 | 22.15 |
| 1476 | CA | VAL | 1077 | 86.799 | 62.820 | 30.048 | 1.00 | 21.41 |
| 1477 | CB | VAL | 1077 | 85.933 | 64.056 | 29.706 | 1.00 | 22.29 |
| 1478 | CG1 | VAL | 1077 | 86.555 | 65.329 | 30.281 | 1.00 | 22.38 |
| 1479 | CG2 | VAL | 1077 | 85.767 | 64.180 | 28.200 | 1.00 | 22.13 |
| 1480 | C | VAL | 1077 | 86.950 | 62.729 | 31.558 | 1.00 | 20.92 |
| 1481 | O | VAL | 1077 | 86.036 | 62.291 | 32.256 | 1.00 | 22.56 |
| 1482 | N | CYS | 1078 | 88.120 | 63.112 | 32.053 | 1.00 | 19.00 |
| 1483 | CA | CYS | 1078 | 88.399 | 63.090 | 33.482 | 1.00 | 18.18 |
| 1484 | CB | CYS | 1078 | 89.886 | 62.832 | 33.736 | 1.00 | 17.52 |
| 1485 | SG | CYS | 1078 | 90.338 | 62.568 | 35.461 | 1.00 | 16.09 |
| 1486 | C | CYS | 1078 | 88.008 | 64.441 | 34.045 | 1.00 | 17.95 |
| 1487 | O | CYS | 1078 | 88.768 | 65.402 | 33.962 | 1.00 | 21.44 |
| 1488 | N | TRP | 1079 | 86.802 | 64.513 | 34.589 | 1.00 | 18.33 |
| 1489 | CA | TRP | 1079 | 86.267 | 65.737 | 35.164 | 1.00 | 14.96 |
| 1490 | CB | TRP | 1079 | 84.744 | 65.736 | 35.066 | 1.00 | 15.12 |
| 1491 | CG | TRP | 1079 | 84.213 | 65.817 | 33.677 | 1.00 | 17.41 |
| 1492 | CD2 | TRP | 1079 | 84.023 | 67.007 | 32.903 | 1.00 | 18.04 |
| 1493 | CE2 | TRP | 1079 | 83.465 | 66.619 | 31.668 | 1.00 | 19.10 |
| 1494 | CE3 | TRP | 1079 | 84.268 | 68.369 | 33.137 | 1.00 | 17.65 |

FIG. 3A-34

| Atom | Atom Type | Resid | # | X | Y | Z | OCC | B |
|---|---|---|---|---|---|---|---|---|
| 1495 | CD1 | TRP | 1079 | 83.780 | 64.781 | 32.904 | 1.00 | 16.78 |
| 1496 | NE1 | TRP | 1079 | 83.325 | 65.254 | 31.693 | 1.00 | 19.80 |
| 1497 | CZ2 | TRP | 1079 | 83.146 | 67.545 | 30.664 | 1.00 | 19.19 |
| 1498 | CZ3 | TRP | 1079 | 83.949 | 69.291 | 32.139 | 1.00 | 15.70 |
| 1499 | CH2 | TRP | 1079 | 83.395 | 68.873 | 30.921 | 1.00 | 16.14 |
| 1500 | C | TRP | 1079 | 86.631 | 65.895 | 36.619 | 1.00 | 15.06 |
| 1501 | O | TRP | 1079 | 86.701 | 64.926 | 37.363 | 1.00 | 14.95 |
| 1502 | N | THR | 1080 | 86.851 | 67.129 | 37.034 | 1.00 | 17.34 |
| 1503 | CA | THR | 1080 | 87.148 | 67.390 | 38.421 | 1.00 | 19.67 |
| 1504 | CB | THR | 1080 | 88.636 | 67.201 | 38.762 | 1.00 | 19.66 |
| 1505 | OG1 | THR | 1080 | 88.794 | 67.207 | 40.187 | 1.00 | 18.69 |
| 1506 | CG2 | THR | 1080 | 89.475 | 68.299 | 38.162 | 1.00 | 21.67 |
| 1507 | C | THR | 1080 | 86.663 | 68.781 | 38.780 | 1.00 | 21.24 |
| 1508 | O | THR | 1080 | 86.113 | 69.499 | 37.938 | 1.00 | 20.94 |
| 1509 | N | VAL | 1081 | 86.867 | 69.141 | 40.039 | 1.00 | 23.41 |
| 1510 | CA | VAL | 1081 | 86.444 | 70.417 | 40.588 | 1.00 | 23.97 |
| 1511 | CB | VAL | 1081 | 86.053 | 70.200 | 42.076 | 1.00 | 22.41 |
| 1512 | CG1 | VAL | 1081 | 87.258 | 70.300 | 42.987 | 1.00 | 21.40 |
| 1513 | CG2 | VAL | 1081 | 84.918 | 71.094 | 42.474 | 1.00 | 23.79 |
| 1514 | C | VAL | 1081 | 87.519 | 71.520 | 40.384 | 1.00 | 25.41 |
| 1515 | O | VAL | 1081 | 88.715 | 71.316 | 40.632 | 1.00 | 24.93 |
| 1516 | N | TYR | 1082 | 87.093 | 72.683 | 39.903 | 1.00 | 25.72 |
| 1517 | CA | TYR | 1082 | 88.016 | 73.785 | 39.643 | 1.00 | 25.46 |
| 1518 | CB | TYR | 1082 | 87.321 | 74.892 | 38.840 | 1.00 | 26.17 |
| 1519 | CG | TYR | 1082 | 88.245 | 76.005 | 38.392 | 1.00 | 26.30 |
| 1520 | CD1 | TYR | 1082 | 88.538 | 77.075 | 39.240 | 1.00 | 26.95 |
| 1521 | CE1 | TYR | 1082 | 89.411 | 78.092 | 38.852 | 1.00 | 28.63 |
| 1522 | CD2 | TYR | 1082 | 88.846 | 75.973 | 37.138 | 1.00 | 26.52 |
| 1523 | CE2 | TYR | 1082 | 89.724 | 76.982 | 36.735 | 1.00 | 29.11 |
| 1524 | CZ | TYR | 1082 | 90.006 | 78.038 | 37.600 | 1.00 | 30.48 |
| 1525 | OH | TYR | 1082 | 90.886 | 79.038 | 37.222 | 1.00 | 31.27 |
| 1526 | C | TYR | 1082 | 88.665 | 74.349 | 40.910 | 1.00 | 25.31 |
| 1527 | O | TYR | 1082 | 89.793 | 74.845 | 40.863 | 1.00 | 22.94 |
| 1528 | N | HIS | 1083 | 87.986 | 74.239 | 42.049 | 1.00 | 24.48 |
| 1529 | CA | HIS | 1083 | 88.568 | 74.748 | 43.283 | 1.00 | 25.01 |
| 1530 | CB | HIS | 1083 | 87.514 | 74.963 | 44.378 | 1.00 | 23.89 |
| 1531 | CG | HIS | 1083 | 86.984 | 73.707 | 44.999 | 1.00 | 27.06 |
| 1532 | CD2 | HIS | 1083 | 87.505 | 72.888 | 45.948 | 1.00 | 28.89 |
| 1533 | ND1 | HIS | 1083 | 85.723 | 73.216 | 44.727 | 1.00 | 29.27 |
| 1534 | CE1 | HIS | 1083 | 85.488 | 72.155 | 45.479 | 1.00 | 28.81 |
| 1535 | NE2 | HIS | 1083 | 86.554 | 71.936 | 46.229 | 1.00 | 30.38 |
| 1536 | C | HIS | 1083 | 89.701 | 73.853 | 43.766 | 1.00 | 26.93 |
| 1537 | O | HIS | 1083 | 90.266 | 74.073 | 44.837 | 1.00 | 29.65 |
| 1538 | N | GLY | 1084 | 90.008 | 72.823 | 42.985 | 1.00 | 25.81 |
| 1539 | CA | GLY | 1084 | 91.082 | 71.922 | 43.336 | 1.00 | 23.74 |
| 1540 | C | GLY | 1084 | 92.153 | 71.987 | 42.266 | 1.00 | 21.87 |
| 1541 | O | GLY | 1084 | 93.286 | 72.360 | 42.540 | 1.00 | 22.00 |
| 1542 | N | ALA | 1085 | 91.771 | 71.667 | 41.035 | 1.00 | 21.01 |
| 1543 | CA | ALA | 1085 | 92.696 | 71.662 | 39.911 | 1.00 | 20.52 |

FIG. 3A-35

| Atom | Atom Type | Resid | # | X | Y | Z | OCC | B |
|---|---|---|---|---|---|---|---|---|
| 1544 | CB | ALA | 1085 | 92.103 | 70.883 | 38.752 | 1.00 | 18.56 |
| 1545 | C | ALA | 1085 | 93.143 | 73.034 | 39.436 | 1.00 | 21.49 |
| 1546 | O | ALA | 1085 | 94.273 | 73.192 | 39.000 | 1.00 | 23.82 |
| 1547 | N | GLY | 1086 | 92.265 | 74.025 | 39.498 | 1.00 | 22.93 |
| 1548 | CA | GLY | 1086 | 92.641 | 75.344 | 39.033 | 1.00 | 22.64 |
| 1549 | C | GLY | 1086 | 92.791 | 75.264 | 37.526 | 1.00 | 25.01 |
| 1550 | O | GLY | 1086 | 91.981 | 74.631 | 36.851 | 1.00 | 25.80 |
| 1551 | N | THR | 1087 | 93.830 | 75.876 | 36.984 | 1.00 | 26.41 |
| 1552 | CA | THR | 1087 | 94.032 | 75.829 | 35.544 | 1.00 | 29.05 |
| 1553 | CB | THR | 1087 | 94.450 | 77.204 | 35.003 | 1.00 | 32.46 |
| 1554 | OG1 | THR | 1087 | 95.572 | 77.683 | 35.758 | 1.00 | 34.46 |
| 1555 | CG2 | THR | 1087 | 93.292 | 78.209 | 35.086 | 1.00 | 33.93 |
| 1556 | C | THR | 1087 | 95.127 | 74.846 | 35.159 | 1.00 | 28.61 |
| 1557 | O | THR | 1087 | 95.422 | 74.679 | 33.971 | 1.00 | 30.95 |
| 1558 | N | ARG | 1088 | 95.689 | 74.145 | 36.138 | 1.00 | 27.72 |
| 1559 | CA | ARG | 1088 | 96.793 | 73.247 | 35.837 | 1.00 | 26.27 |
| 1560 | CB | ARG | 1088 | 97.606 | 72.923 | 37.083 | 1.00 | 25.05 |
| 1561 | CG | ARG | 1088 | 96.830 | 72.482 | 38.249 | 1.00 | 22.82 |
| 1562 | CD | ARG | 1088 | 97.651 | 72.707 | 39.472 | 1.00 | 22.84 |
| 1563 | NE | ARG | 1088 | 96.964 | 73.601 | 40.382 | 1.00 | 26.47 |
| 1564 | CZ | ARG | 1088 | 97.386 | 73.875 | 41.607 | 1.00 | 28.75 |
| 1565 | NH1 | ARG | 1088 | 98.505 | 73.324 | 42.068 | 1.00 | 31.62 |
| 1566 | NH2 | ARG | 1088 | 96.677 | 74.691 | 42.375 | 1.00 | 29.37 |
| 1567 | C | ARG | 1088 | 96.577 | 72.014 | 34.993 | 1.00 | 25.66 |
| 1568 | O | ARG | 1088 | 95.448 | 71.583 | 34.752 | 1.00 | 28.07 |
| 1569 | N | THR | 1089 | 97.694 | 71.509 | 34.487 | 1.00 | 23.84 |
| 1570 | CA | THR | 1089 | 97.736 | 70.343 | 33.633 | 1.00 | 23.41 |
| 1571 | CB | THR | 1089 | 99.014 | 70.390 | 32.769 | 1.00 | 23.85 |
| 1572 | OG1 | THR | 1089 | 100.146 | 70.668 | 33.602 | 1.00 | 24.27 |
| 1573 | CG2 | THR | 1089 | 98.916 | 71.474 | 31.715 | 1.00 | 21.97 |
| 1574 | C | THR | 1089 | 97.742 | 69.085 | 34.493 | 1.00 | 23.76 |
| 1575 | O | THR | 1089 | 97.876 | 69.172 | 35.717 | 1.00 | 24.27 |
| 1576 | N | ILE | 1090 | 97.546 | 67.925 | 33.869 | 1.00 | 21.48 |
| 1577 | CA | ILE | 1090 | 97.570 | 66.659 | 34.600 | 1.00 | 20.72 |
| 1578 | CB | ILE | 1090 | 96.251 | 65.811 | 34.409 | 1.00 | 19.48 |
| 1579 | CG2 | ILE | 1090 | 96.115 | 65.296 | 32.977 | 1.00 | 20.97 |
| 1580 | CG1 | ILE | 1090 | 96.216 | 64.642 | 35.405 | 1.00 | 19.86 |
| 1581 | CD1 | ILE | 1090 | 94.857 | 63.936 | 35.519 | 1.00 | 15.19 |
| 1582 | C | ILE | 1090 | 98.803 | 65.896 | 34.135 | 1.00 | 19.55 |
| 1583 | O | ILE | 1090 | 99.091 | 65.841 | 32.940 | 1.00 | 17.18 |
| 1584 | N | ALA | 1091 | 99.582 | 65.395 | 35.085 | 1.00 | 19.06 |
| 1585 | CA | ALA | 1091 | 100.786 | 64.648 | 34.750 | 1.00 | 17.95 |
| 1586 | CB | ALA | 1091 | 101.558 | 64.318 | 36.007 | 1.00 | 15.33 |
| 1587 | C | ALA | 1091 | 100.378 | 63.374 | 34.036 | 1.00 | 19.98 |
| 1588 | O | ALA | 1091 | 99.509 | 62.643 | 34.515 | 1.00 | 22.10 |
| 1589 | N | SER | 1092 | 100.978 | 63.116 | 32.882 | 1.00 | 21.44 |
| 1590 | CA | SER | 1092 | 100.667 | 61.913 | 32.128 | 1.00 | 24.34 |
| 1591 | CB | SER | 1092 | 99.759 | 62.244 | 30.941 | 1.00 | 24.98 |
| 1592 | OG | SER | 1092 | 100.517 | 62.642 | 29.817 | 1.00 | 26.24 |

FIG. 3A-36

| Atom | Atom Type | Resid | # | X | Y | Z | OCC | B |
|---|---|---|---|---|---|---|---|---|
| 1593 | C | SER | 1092 | 101.953 | 61.271 | 31.629 | 1.00 | 25.86 |
| 1594 | O | SER | 1092 | 103.030 | 61.838 | 31.771 | 1.00 | 27.85 |
| 1595 | N | PRO | 1093 | 101.862 | 60.064 | 31.060 | 1.00 | 27.32 |
| 1596 | CD | PRO | 1093 | 100.670 | 59.207 | 30.955 | 1.00 | 28.88 |
| 1597 | CA | PRO | 1093 | 103.038 | 59.366 | 30.544 | 1.00 | 29.05 |
| 1598 | CB | PRO | 1093 | 102.424 | 58.145 | 29.864 | 1.00 | 29.52 |
| 1599 | CG | PRO | 1093 | 101.270 | 57.843 | 30.734 | 1.00 | 30.09 |
| 1600 | C | PRO | 1093 | 103.807 | 60.199 | 29.532 | 1.00 | 29.67 |
| 1601 | O | PRO | 1093 | 105.029 | 60.101 | 29.450 | 1.00 | 31.90 |
| 1602 | N | LYS | 1094 | 103.081 | 61.014 | 28.767 | 1.00 | 29.17 |
| 1603 | CA | LYS | 1094 | 103.669 | 61.855 | 27.729 | 1.00 | 28.35 |
| 1604 | CB | LYS | 1094 | 102.769 | 61.857 | 26.492 | 1.00 | 25.80 |
| 1605 | CG | LYS | 1094 | 102.678 | 60.505 | 25.833 | 1.00 | 26.73 |
| 1606 | CD | LYS | 1094 | 102.036 | 60.568 | 24.467 | 1.00 | 28.73 |
| 1607 | CE | LYS | 1094 | 102.138 | 59.217 | 23.790 | 1.00 | 30.21 |
| 1608 | NZ | LYS | 1094 | 101.569 | 59.241 | 22.428 | 1.00 | 31.93 |
| 1609 | C | LYS | 1094 | 103.934 | 63.281 | 28.177 | 1.00 | 29.51 |
| 1610 | O | LYS | 1094 | 104.098 | 64.187 | 27.348 | 1.00 | 31.07 |
| 1611 | N | GLY | 1095 | 104.021 | 63.471 | 29.487 | 1.00 | 30.06 |
| 1612 | CA | GLY | 1095 | 104.261 | 64.794 | 30.035 | 1.00 | 29.06 |
| 1613 | C | GLY | 1095 | 102.962 | 65.406 | 30.514 | 1.00 | 27.34 |
| 1614 | O | GLY | 1095 | 101.935 | 64.724 | 30.527 | 1.00 | 28.11 |
| 1615 | N | PRO | 1096 | 102.973 | 66.668 | 30.959 | 1.00 | 24.82 |
| 1616 | CD | PRO | 1096 | 104.071 | 67.640 | 31.038 | 1.00 | 24.20 |
| 1617 | CA | PRO | 1096 | 101.720 | 67.258 | 31.419 | 1.00 | 24.35 |
| 1618 | CB | PRO | 1096 | 102.163 | 68.611 | 31.970 | 1.00 | 23.18 |
| 1619 | CG | PRO | 1096 | 103.321 | 68.948 | 31.117 | 1.00 | 25.11 |
| 1620 | C | PRO | 1096 | 100.732 | 67.401 | 30.268 | 1.00 | 24.48 |
| 1621 | O | PRO | 1096 | 101.125 | 67.569 | 29.116 | 1.00 | 25.88 |
| 1622 | N | VAL | 1097 | 99.450 | 67.270 | 30.582 | 1.00 | 25.45 |
| 1623 | CA | VAL | 1097 | 98.393 | 67.386 | 29.595 | 1.00 | 24.09 |
| 1624 | CB | VAL | 1097 | 97.598 | 66.077 | 29.520 | 1.00 | 22.86 |
| 1625 | CG1 | VAL | 1097 | 96.393 | 66.224 | 28.609 | 1.00 | 21.59 |
| 1626 | CG2 | VAL | 1097 | 98.510 | 64.964 | 29.009 | 1.00 | 23.88 |
| 1627 | C | VAL | 1097 | 97.495 | 68.563 | 29.973 | 1.00 | 24.81 |
| 1628 | O | VAL | 1097 | 97.051 | 68.675 | 31.113 | 1.00 | 25.35 |
| 1629 | N | ILE | 1098 | 97.298 | 69.478 | 29.032 | 1.00 | 25.32 |
| 1630 | CA | ILE | 1098 | 96.474 | 70.666 | 29.252 | 1.00 | 25.37 |
| 1631 | CB | ILE | 1098 | 96.731 | 71.698 | 28.135 | 1.00 | 27.24 |
| 1632 | CG2 | ILE | 1098 | 96.029 | 73.015 | 28.447 | 1.00 | 26.41 |
| 1633 | CG1 | ILE | 1098 | 98.247 | 71.932 | 28.008 | 1.00 | 30.74 |
| 1634 | CD1 | ILE | 1098 | 98.659 | 72.943 | 26.946 | 1.00 | 32.59 |
| 1635 | C | ILE | 1098 | 94.986 | 70.313 | 29.331 | 1.00 | 23.54 |
| 1636 | O | ILE | 1098 | 94.546 | 69.325 | 28.752 | 1.00 | 24.20 |
| 1637 | N | GLN | 1099 | 94.212 | 71.120 | 30.043 | 1.00 | 20.79 |
| 1638 | CA | GLN | 1099 | 92.787 | 70.853 | 30.193 | 1.00 | 20.64 |
| 1639 | CB | GLN | 1099 | 92.188 | 71.774 | 31.236 | 1.00 | 16.40 |
| 1640 | CG | GLN | 1099 | 92.897 | 71.747 | 32.534 | 1.00 | 17.16 |
| 1641 | CD | GLN | 1099 | 92.215 | 72.607 | 33.541 | 1.00 | 20.14 |

FIG. 3A-37

| Atom | Atom Type | Resid | # | X | Y | Z | OCC | B |
|---|---|---|---|---|---|---|---|---|
| 1642 | OE1 | GLN | 1099 | 91.129 | 73.118 | 33.286 | 1.00 | 25.87 |
| 1643 | NE2 | GLN | 1099 | 92.827 | 72.767 | 34.704 | 1.00 | 21.32 |
| 1644 | C | GLN | 1099 | 91.973 | 70.990 | 28.918 | 1.00 | 22.84 |
| 1645 | O | GLN | 1099 | 92.217 | 71.882 | 28.109 | 1.00 | 25.86 |
| 1646 | N | MET | 1100 | 91.006 | 70.090 | 28.752 | 1.00 | 23.50 |
| 1647 | CA | MET | 1100 | 90.099 | 70.094 | 27.606 | 1.00 | 22.12 |
| 1648 | CB | MET | 1100 | 89.418 | 68.737 | 27.447 | 1.00 | 20.94 |
| 1649 | CG | MET | 1100 | 90.052 | 67.816 | 26.450 | 1.00 | 22.51 |
| 1650 | SD | MET | 1100 | 88.916 | 66.522 | 25.981 | 1.00 | 22.15 |
| 1651 | CE | MET | 1100 | 88.786 | 65.731 | 27.470 | 1.00 | 23.27 |
| 1652 | C | MET | 1100 | 89.002 | 71.124 | 27.819 | 1.00 | 23.05 |
| 1653 | O | MET | 1100 | 88.581 | 71.801 | 26.879 | 1.00 | 24.71 |
| 1654 | N | TYR | 1101 | 88.495 | 71.180 | 29.047 | 1.00 | 22.24 |
| 1655 | CA | TYR | 1101 | 87.424 | 72.098 | 29.402 | 1.00 | 20.19 |
| 1656 | CB | TYR | 1101 | 86.103 | 71.340 | 29.561 | 1.00 | 19.75 |
| 1657 | CG | TYR | 1101 | 85.809 | 70.388 | 28.431 | 1.00 | 21.76 |
| 1658 | CD1 | TYR | 1101 | 86.004 | 69.022 | 28.582 | 1.00 | 20.14 |
| 1659 | CE1 | TYR | 1101 | 85.784 | 68.146 | 27.525 | 1.00 | 22.53 |
| 1660 | CD2 | TYR | 1101 | 85.383 | 70.859 | 27.195 | 1.00 | 22.07 |
| 1661 | CE2 | TYR | 1101 | 85.161 | 69.998 | 26.137 | 1.00 | 21.98 |
| 1662 | CZ | TYR | 1101 | 85.363 | 68.642 | 26.304 | 1.00 | 22.76 |
| 1663 | OH | TYR | 1101 | 85.130 | 67.781 | 25.254 | 1.00 | 24.74 |
| 1664 | C | TYR | 1101 | 87.750 | 72.764 | 30.716 | 1.00 | 21.21 |
| 1665 | O | TYR | 1101 | 88.437 | 72.187 | 31.560 | 1.00 | 22.22 |
| 1666 | N | THR | 1102 | 87.236 | 73.973 | 30.890 | 1.00 | 23.24 |
| 1667 | CA | THR | 1102 | 87.424 | 74.741 | 32.111 | 1.00 | 24.37 |
| 1668 | CB | THR | 1102 | 88.640 | 75.681 | 32.013 | 1.00 | 24.53 |
| 1669 | OG1 | THR | 1102 | 89.738 | 74.991 | 31.399 | 1.00 | 23.57 |
| 1670 | CG2 | THR | 1102 | 89.047 | 76.169 | 33.403 | 1.00 | 22.58 |
| 1671 | C | THR | 1102 | 86.175 | 75.597 | 32.244 | 1.00 | 25.86 |
| 1672 | O | THR | 1102 | 85.658 | 76.094 | 31.246 | 1.00 | 28.08 |
| 1673 | N | ASN | 1103 | 85.668 | 75.740 | 33.460 | 1.00 | 26.20 |
| 1674 | CA | ASN | 1103 | 84.480 | 76.547 | 33.700 | 1.00 | 25.78 |
| 1675 | CB | ASN | 1103 | 83.213 | 75.752 | 33.372 | 1.00 | 26.82 |
| 1676 | CG | ASN | 1103 | 81.947 | 76.585 | 33.511 | 1.00 | 28.67 |
| 1677 | OD1 | ASN | 1103 | 81.932 | 77.609 | 34.199 | 1.00 | 30.76 |
| 1678 | ND2 | ASN | 1103 | 80.871 | 76.135 | 32.882 | 1.00 | 27.57 |
| 1679 | C | ASN | 1103 | 84.480 | 76.995 | 35.156 | 1.00 | 26.25 |
| 1680 | O | ASN | 1103 | 83.832 | 76.391 | 36.006 | 1.00 | 27.25 |
| 1681 | N | VAL | 1104 | 85.212 | 78.069 | 35.430 | 1.00 | 27.39 |
| 1682 | CA | VAL | 1104 | 85.333 | 78.611 | 36.776 | 1.00 | 28.21 |
| 1683 | CB | VAL | 1104 | 86.025 | 79.980 | 36.783 | 1.00 | 27.51 |
| 1684 | CG1 | VAL | 1104 | 86.316 | 80.397 | 38.205 | 1.00 | 28.55 |
| 1685 | CG2 | VAL | 1104 | 87.298 | 79.948 | 35.963 | 1.00 | 28.06 |
| 1686 | C | VAL | 1104 | 83.978 | 78.796 | 37.419 | 1.00 | 30.54 |
| 1687 | O | VAL | 1104 | 83.803 | 78.517 | 38.604 | 1.00 | 31.53 |
| 1688 | N | ASP | 1105 | 83.022 | 79.260 | 36.626 | 1.00 | 33.66 |
| 1689 | CA | ASP | 1105 | 81.677 | 79.503 | 37.117 | 1.00 | 36.82 |
| 1690 | CB | ASP | 1105 | 80.788 | 80.061 | 36.001 | 1.00 | 41.34 |

FIG. 3A-38

| Atom | Atom Type | Resid | # | X | Y | Z | OCC | B |
|---|---|---|---|---|---|---|---|---|
| 1691 | CG | ASP | 1105 | 81.192 | 81.457 | 35.573 | 1.00 | 45.36 |
| 1692 | OD1 | ASP | 1105 | 81.157 | 82.369 | 36.429 | 1.00 | 47.53 |
| 1693 | OD2 | ASP | 1105 | 81.543 | 81.636 | 34.382 | 1.00 | 48.54 |
| 1694 | C | ASP | 1105 | 81.058 | 78.241 | 37.676 | 1.00 | 36.71 |
| 1695 | O | ASP | 1105 | 80.645 | 78.200 | 38.835 | 1.00 | 36.88 |
| 1696 | N | GLN | 1106 | 81.011 | 77.203 | 36.851 | 1.00 | 36.71 |
| 1697 | CA | GLN | 1106 | 80.417 | 75.940 | 37.266 | 1.00 | 36.44 |
| 1698 | CB | GLN | 1106 | 79.895 | 75.194 | 36.042 | 1.00 | 38.58 |
| 1699 | CG | GLN | 1106 | 78.821 | 76.012 | 35.312 | 1.00 | 43.02 |
| 1700 | CD | GLN | 1106 | 78.192 | 75.305 | 34.120 | 1.00 | 44.86 |
| 1701 | OE1 | GLN | 1106 | 77.334 | 75.870 | 33.437 | 1.00 | 44.11 |
| 1702 | NE2 | GLN | 1106 | 78.606 | 74.068 | 33.866 | 1.00 | 47.22 |
| 1703 | C | GLN | 1106 | 81.342 | 75.077 | 38.122 | 1.00 | 34.06 |
| 1704 | O | GLN | 1106 | 80.930 | 74.029 | 38.625 | 1.00 | 33.78 |
| 1705 | N | ASP | 1107 | 82.561 | 75.575 | 38.339 | 1.00 | 29.82 |
| 1706 | CA | ASP | 1107 | 83.577 | 74.900 | 39.144 | 1.00 | 26.00 |
| 1707 | CB | ASP | 1107 | 83.039 | 74.635 | 40.551 | 1.00 | 26.29 |
| 1708 | CG | ASP | 1107 | 84.138 | 74.436 | 41.574 | 1.00 | 25.28 |
| 1709 | OD1 | ASP | 1107 | 85.287 | 74.822 | 41.303 | 1.00 | 26.49 |
| 1710 | OD2 | ASP | 1107 | 83.844 | 73.914 | 42.666 | 1.00 | 25.48 |
| 1711 | C | ASP | 1107 | 84.016 | 73.597 | 38.492 | 1.00 | 23.82 |
| 1712 | O | ASP | 1107 | 84.348 | 72.637 | 39.176 | 1.00 | 23.57 |
| 1713 | N | LEU | 1108 | 84.066 | 73.593 | 37.167 | 1.00 | 21.98 |
| 1714 | CA | LEU | 1108 | 84.440 | 72.413 | 36.403 | 1.00 | 22.63 |
| 1715 | CB | LEU | 1108 | 83.349 | 72.083 | 35.378 | 1.00 | 21.22 |
| 1716 | CG | LEU | 1108 | 82.093 | 71.415 | 35.928 | 1.00 | 21.50 |
| 1717 | CD1 | LEU | 1108 | 81.053 | 71.249 | 34.840 | 1.00 | 21.03 |
| 1718 | CD2 | LEU | 1108 | 82.473 | 70.079 | 36.506 | 1.00 | 20.86 |
| 1719 | C | LEU | 1108 | 85.781 | 72.524 | 35.686 | 1.00 | 22.72 |
| 1720 | O | LEU | 1108 | 86.206 | 73.608 | 35.285 | 1.00 | 24.88 |
| 1721 | N | VAL | 1109 | 86.413 | 71.375 | 35.495 | 1.00 | 20.91 |
| 1722 | CA | VAL | 1109 | 87.695 | 71.260 | 34.820 | 1.00 | 20.17 |
| 1723 | CB | VAL | 1109 | 88.855 | 71.399 | 35.833 | 1.00 | 21.15 |
| 1724 | CG1 | VAL | 1109 | 90.117 | 70.788 | 35.292 | 1.00 | 22.22 |
| 1725 | CG2 | VAL | 1109 | 89.092 | 72.858 | 36.156 | 1.00 | 22.70 |
| 1726 | C | VAL | 1109 | 87.674 | 69.850 | 34.245 | 1.00 | 19.05 |
| 1727 | O | VAL | 1109 | 87.065 | 68.967 | 34.839 | 1.00 | 19.81 |
| 1728 | N | GLY | 1110 | 88.306 | 69.648 | 33.092 | 1.00 | 17.18 |
| 1729 | CA | GLY | 1110 | 88.328 | 68.334 | 32.477 | 1.00 | 16.06 |
| 1730 | C | GLY | 1110 | 89.518 | 68.134 | 31.558 | 1.00 | 17.59 |
| 1731 | O | GLY | 1110 | 89.896 | 69.050 | 30.823 | 1.00 | 16.16 |
| 1732 | N | TRP | 1111 | 90.139 | 66.957 | 31.650 | 1.00 | 17.19 |
| 1733 | CA | TRP | 1111 | 91.299 | 66.569 | 30.835 | 1.00 | 16.21 |
| 1734 | CB | TRP | 1111 | 92.498 | 66.181 | 31.721 | 1.00 | 14.75 |
| 1735 | CG | TRP | 1111 | 93.039 | 67.225 | 32.642 | 1.00 | 11.64 |
| 1736 | CD2 | TRP | 1111 | 92.802 | 67.337 | 34.058 | 1.00 | 11.04 |
| 1737 | CE2 | TRP | 1111 | 93.577 | 68.419 | 34.525 | 1.00 | 11.37 |
| 1738 | CE3 | TRP | 1111 | 92.011 | 66.626 | 34.973 | 1.00 | 13.68 |
| 1739 | CD1 | TRP | 1111 | 93.916 | 68.213 | 32.321 | 1.00 | 11.69 |

FIG. 3A-39

| Atom | Atom Type | Resid | # | X | Y | Z | OCC | B |
|---|---|---|---|---|---|---|---|---|
| 1740 | NE1 | TRP | 1111 | 94.247 | 68.935 | 33.447 | 1.00 | 14.19 |
| 1741 | CZ2 | TRP | 1111 | 93.589 | 68.809 | 35.867 | 1.00 | 11.96 |
| 1742 | CZ3 | TRP | 1111 | 92.022 | 67.011 | 36.308 | 1.00 | 11.51 |
| 1743 | CH2 | TRP | 1111 | 92.808 | 68.095 | 36.741 | 1.00 | 13.13 |
| 1744 | C | TRP | 1111 | 90.873 | 65.290 | 30.125 | 1.00 | 17.82 |
| 1745 | O | TRP | 1111 | 89.882 | 64.670 | 30.516 | 1.00 | 20.28 |
| 1746 | N | PRO | 1112 | 91.581 | 64.885 | 29.053 | 1.00 | 18.22 |
| 1747 | CD | PRO | 1112 | 92.711 | 65.493 | 28.331 | 1.00 | 17.52 |
| 1748 | CA | PRO | 1112 | 91.153 | 63.637 | 28.406 | 1.00 | 16.49 |
| 1749 | CB | PRO | 1112 | 92.189 | 63.452 | 27.309 | 1.00 | 15.54 |
| 1750 | CG | PRO | 1112 | 92.586 | 64.846 | 26.978 | 1.00 | 18.88 |
| 1751 | C | PRO | 1112 | 91.318 | 62.567 | 29.477 | 1.00 | 18.48 |
| 1752 | O | PRO | 1112 | 92.207 | 62.679 | 30.322 | 1.00 | 21.84 |
| 1753 | N | ALA | 1113 | 90.443 | 61.573 | 29.512 | 1.00 | 19.42 |
| 1754 | CA | ALA | 1113 | 90.572 | 60.540 | 30.526 | 1.00 | 18.50 |
| 1755 | CB | ALA | 1113 | 89.441 | 59.543 | 30.420 | 1.00 | 17.46 |
| 1756 | C | ALA | 1113 | 91.909 | 59.851 | 30.319 | 1.00 | 20.35 |
| 1757 | O | ALA | 1113 | 92.278 | 59.532 | 29.189 | 1.00 | 21.19 |
| 1758 | N | PRO | 1114 | 92.689 | 59.681 | 31.396 | 1.00 | 21.47 |
| 1759 | CD | PRO | 1114 | 92.488 | 60.128 | 32.783 | 1.00 | 22.45 |
| 1760 | CA | PRO | 1114 | 93.984 | 59.022 | 31.250 | 1.00 | 22.96 |
| 1761 | CB | PRO | 1114 | 94.529 | 59.018 | 32.682 | 1.00 | 23.65 |
| 1762 | CG | PRO | 1114 | 93.306 | 59.138 | 33.537 | 1.00 | 22.54 |
| 1763 | C | PRO | 1114 | 93.835 | 57.620 | 30.693 | 1.00 | 24.51 |
| 1764 | O | PRO | 1114 | 92.888 | 56.903 | 31.024 | 1.00 | 26.99 |
| 1765 | N | GLN | 1115 | 94.730 | 57.254 | 29.786 | 1.00 | 26.09 |
| 1766 | CA | GLN | 1115 | 94.706 | 55.925 | 29.195 | 1.00 | 28.46 |
| 1767 | CB | GLN | 1115 | 95.903 | 55.744 | 28.258 | 1.00 | 30.59 |
| 1768 | CG | GLN | 1115 | 95.895 | 56.656 | 27.033 | 1.00 | 34.32 |
| 1769 | CD | GLN | 1115 | 94.865 | 56.236 | 26.009 | 1.00 | 37.60 |
| 1770 | OE1 | GLN | 1115 | 94.731 | 55.051 | 25.699 | 1.00 | 39.96 |
| 1771 | NE2 | GLN | 1115 | 94.122 | 57.203 | 25.479 | 1.00 | 41.37 |
| 1772 | C | GLN | 1115 | 94.762 | 54.895 | 30.325 | 1.00 | 28.93 |
| 1773 | O | GLN | 1115 | 95.548 | 55.039 | 31.269 | 1.00 | 29.99 |
| 1774 | N | GLY | 1116 | 93.881 | 53.902 | 30.257 | 1.00 | 28.45 |
| 1775 | CA | GLY | 1116 | 93.842 | 52.862 | 31.272 | 1.00 | 28.19 |
| 1776 | C | GLY | 1116 | 92.595 | 52.883 | 32.140 | 1.00 | 28.90 |
| 1777 | O | GLY | 1116 | 92.155 | 51.840 | 32.633 | 1.00 | 30.64 |
| 1778 | N | SER | 1117 | 92.027 | 54.071 | 32.327 | 1.00 | 28.03 |
| 1779 | CA | SER | 1117 | 90.834 | 54.246 | 33.143 | 1.00 | 25.22 |
| 1780 | CB | SER | 1117 | 90.688 | 55.717 | 33.517 | 1.00 | 21.89 |
| 1781 | OG | SER | 1117 | 90.524 | 56.491 | 32.349 | 1.00 | 17.60 |
| 1782 | C | SER | 1117 | 89.567 | 53.784 | 32.432 | 1.00 | 25.37 |
| 1783 | O | SER | 1117 | 89.592 | 53.456 | 31.241 | 1.00 | 26.03 |
| 1784 | N | ARG | 1118 | 88.468 | 53.734 | 33.181 | 1.00 | 25.35 |
| 1785 | CA | ARG | 1118 | 87.170 | 53.350 | 32.641 | 1.00 | 25.91 |
| 1786 | CB | ARG | 1118 | 86.635 | 52.074 | 33.300 | 1.00 | 31.51 |
| 1787 | CG | ARG | 1118 | 87.368 | 50.796 | 32.919 | 1.00 | 42.46 |
| 1788 | CD | ARG | 1118 | 87.604 | 50.721 | 31.414 | 1.00 | 51.80 |

FIG. 3A-40

| Atom | Atom Type | Resid | # | X | Y | Z | OCC | B |
|---|---|---|---|---|---|---|---|---|
| 1789 | NE | ARG | 1118 | 87.874 | 49.357 | 30.956 | 1.00 | 61.09 |
| 1790 | CZ | ARG | 1118 | 88.830 | 49.022 | 30.090 | 1.00 | 65.33 |
| 1791 | NH1 | ARG | 1118 | 88.981 | 47.749 | 29.738 | 1.00 | 68.07 |
| 1792 | NH2 | ARG | 1118 | 89.661 | 49.941 | 29.606 | 1.00 | 67.27 |
| 1793 | C | ARG | 1118 | 86.252 | 54.515 | 32.960 | 1.00 | 24.68 |
| 1794 | O | ARG | 1118 | 86.375 | 55.128 | 34.020 | 1.00 | 24.68 |
| 1795 | N | SER | 1119 | 85.355 | 54.844 | 32.043 | 1.00 | 22.26 |
| 1796 | CA | SER | 1119 | 84.446 | 55.957 | 32.263 | 1.00 | 22.87 |
| 1797 | CB | SER | 1119 | 84.333 | 56.807 | 30.993 | 1.00 | 21.77 |
| 1798 | OG | SER | 1119 | 85.535 | 57.511 | 30.735 | 1.00 | 26.02 |
| 1799 | C | SER | 1119 | 83.053 | 55.536 | 32.692 | 1.00 | 20.90 |
| 1800 | O | SER | 1119 | 82.620 | 54.421 | 32.425 | 1.00 | 21.97 |
| 1801 | N | LEU | 1120 | 82.379 | 56.424 | 33.409 | 1.00 | 19.67 |
| 1802 | CA | LEU | 1120 | 81.008 | 56.195 | 33.827 | 1.00 | 16.91 |
| 1803 | CB | LEU | 1120 | 80.691 | 56.939 | 35.131 | 1.00 | 13.88 |
| 1804 | CG | LEU | 1120 | 81.329 | 56.564 | 36.469 | 1.00 | 11.68 |
| 1805 | CD1 | LEU | 1120 | 80.978 | 57.623 | 37.470 | 1.00 | 11.76 |
| 1806 | CD2 | LEU | 1120 | 80.854 | 55.209 | 36.950 | 1.00 | 13.04 |
| 1807 | C | LEU | 1120 | 80.197 | 56.828 | 32.704 | 1.00 | 16.42 |
| 1808 | O | LEU | 1120 | 80.753 | 57.509 | 31.840 | 1.00 | 15.05 |
| 1809 | N | THR | 1121 | 78.893 | 56.602 | 32.714 | 1.00 | 18.09 |
| 1810 | CA | THR | 1121 | 78.012 | 57.189 | 31.719 | 1.00 | 19.50 |
| 1811 | CB | THR | 1121 | 77.383 | 56.120 | 30.825 | 1.00 | 20.88 |
| 1812 | OG1 | THR | 1121 | 77.011 | 54.987 | 31.620 | 1.00 | 26.65 |
| 1813 | CG2 | THR | 1121 | 78.372 | 55.683 | 29.758 | 1.00 | 21.77 |
| 1814 | C | THR | 1121 | 76.938 | 57.941 | 32.485 | 1.00 | 18.52 |
| 1815 | O | THR | 1121 | 76.613 | 57.579 | 33.616 | 1.00 | 20.72 |
| 1816 | N | PRO | 1122 | 76.441 | 59.052 | 31.931 | 1.00 | 18.23 |
| 1817 | CD | PRO | 1122 | 76.865 | 59.703 | 30.680 | 1.00 | 17.02 |
| 1818 | CA | PRO | 1122 | 75.403 | 59.835 | 32.606 | 1.00 | 18.29 |
| 1819 | CB | PRO | 1122 | 75.108 | 60.939 | 31.600 | 1.00 | 18.11 |
| 1820 | CG | PRO | 1122 | 76.432 | 61.122 | 30.908 | 1.00 | 16.83 |
| 1821 | C | PRO | 1122 | 74.153 | 59.019 | 32.931 | 1.00 | 20.74 |
| 1822 | O | PRO | 1122 | 73.887 | 57.985 | 32.317 | 1.00 | 22.14 |
| 1823 | N | CYS | 1123 | 73.405 | 59.476 | 33.925 | 1.00 | 23.09 |
| 1824 | CA | CYS | 1123 | 72.184 | 58.807 | 34.348 | 1.00 | 25.58 |
| 1825 | CB | CYS | 1123 | 71.811 | 59.265 | 35.759 | 1.00 | 25.03 |
| 1826 | SG | CYS | 1123 | 70.363 | 58.469 | 36.474 | 1.00 | 22.23 |
| 1827 | C | CYS | 1123 | 71.069 | 59.169 | 33.381 | 1.00 | 27.87 |
| 1828 | O | CYS | 1123 | 70.978 | 60.314 | 32.942 | 1.00 | 29.71 |
| 1829 | N | THR | 1124 | 70.211 | 58.199 | 33.075 | 1.00 | 30.25 |
| 1830 | CA | THR | 1124 | 69.086 | 58.398 | 32.162 | 1.00 | 30.66 |
| 1831 | CB | THR | 1124 | 69.407 | 57.845 | 30.756 | 1.00 | 29.19 |
| 1832 | OG1 | THR | 1124 | 69.987 | 56.537 | 30.874 | 1.00 | 28.07 |
| 1833 | CG2 | THR | 1124 | 70.354 | 58.776 | 30.009 | 1.00 | 26.85 |
| 1834 | C | THR | 1124 | 67.853 | 57.684 | 32.720 | 1.00 | 32.73 |
| 1835 | O | THR | 1124 | 67.224 | 56.867 | 32.049 | 1.00 | 35.79 |
| 1836 | N | CYS | 1125 | 67.532 | 57.980 | 33.971 | 1.00 | 33.01 |
| 1837 | CA | CYS | 1125 | 66.395 | 57.373 | 34.639 | 1.00 | 32.02 |

FIG. 3A-41

| Atom | Atom Type | Resid | # | X | Y | Z | OCC | B |
|---|---|---|---|---|---|---|---|---|
| 1838 | CB | CYS | 1125 | 66.836 | 56.136 | 35.433 | 1.00 | 33.60 |
| 1839 | SG | CYS | 1125 | 67.885 | 56.458 | 36.910 | 1.00 | 37.33 |
| 1840 | C | CYS | 1125 | 65.785 | 58.403 | 35.571 | 1.00 | 31.70 |
| 1841 | O | CYS | 1125 | 64.771 | 58.151 | 36.211 | 1.00 | 35.06 |
| 1842 | N | GLY | 1126 | 66.417 | 59.569 | 35.642 | 1.00 | 30.53 |
| 1843 | CA | GLY | 1126 | 65.927 | 60.636 | 36.490 | 1.00 | 30.87 |
| 1844 | C | GLY | 1126 | 65.769 | 60.278 | 37.954 | 1.00 | 30.72 |
| 1845 | O | GLY | 1126 | 65.092 | 60.991 | 38.691 | 1.00 | 33.42 |
| 1846 | N | SER | 1127 | 66.408 | 59.200 | 38.394 | 1.00 | 29.86 |
| 1847 | CA | SER | 1127 | 66.297 | 58.790 | 39.786 | 1.00 | 29.79 |
| 1848 | CB | SER | 1127 | 67.098 | 57.519 | 40.045 | 1.00 | 28.49 |
| 1849 | OG | SER | 1127 | 67.027 | 57.174 | 41.421 | 1.00 | 30.28 |
| 1850 | C | SER | 1127 | 66.718 | 59.881 | 40.771 | 1.00 | 31.88 |
| 1851 | O | SER | 1127 | 67.629 | 60.673 | 40.499 | 1.00 | 31.79 |
| 1852 | N | SER | 1128 | 66.045 | 59.908 | 41.917 | 1.00 | 32.25 |
| 1853 | CA | SER | 1128 | 66.335 | 60.884 | 42.957 | 1.00 | 32.78 |
| 1854 | CB | SER | 1128 | 65.045 | 61.545 | 43.431 | 1.00 | 34.11 |
| 1855 | OG | SER | 1128 | 64.117 | 60.564 | 43.869 | 1.00 | 38.32 |
| 1856 | C | SER | 1128 | 67.061 | 60.246 | 44.139 | 1.00 | 31.47 |
| 1857 | O | SER | 1128 | 67.345 | 60.924 | 45.130 | 1.00 | 30.85 |
| 1858 | N | ASP | 1129 | 67.293 | 58.936 | 44.066 | 1.00 | 29.87 |
| 1859 | CA | ASP | 1129 | 68.012 | 58.219 | 45.123 | 1.00 | 29.89 |
| 1860 | CB | ASP | 1129 | 67.408 | 56.839 | 45.348 | 1.00 | 31.52 |
| 1861 | CG | ASP | 1129 | 65.931 | 56.898 | 45.658 | 1.00 | 34.71 |
| 1862 | OD1 | ASP | 1129 | 65.561 | 57.534 | 46.667 | 1.00 | 36.72 |
| 1863 | OD2 | ASP | 1129 | 65.141 | 56.320 | 44.878 | 1.00 | 35.48 |
| 1864 | C | ASP | 1129 | 69.442 | 58.075 | 44.624 | 1.00 | 29.13 |
| 1865 | O | ASP | 1129 | 69.711 | 57.254 | 43.745 | 1.00 | 28.49 |
| 1866 | N | LEU | 1130 | 70.342 | 58.886 | 45.177 | 1.00 | 27.18 |
| 1867 | CA | LEU | 1130 | 71.740 | 58.907 | 44.760 | 1.00 | 24.28 |
| 1868 | CB | LEU | 1130 | 72.156 | 60.349 | 44.445 | 1.00 | 23.07 |
| 1869 | CG | LEU | 1130 | 71.172 | 61.255 | 43.689 | 1.00 | 21.59 |
| 1870 | CD1 | LEU | 1130 | 71.727 | 62.664 | 43.589 | 1.00 | 19.14 |
| 1871 | CD2 | LEU | 1130 | 70.883 | 60.693 | 42.319 | 1.00 | 19.32 |
| 1872 | C | LEU | 1130 | 72.690 | 58.324 | 45.802 | 1.00 | 23.34 |
| 1873 | O | LEU | 1130 | 72.347 | 58.198 | 46.979 | 1.00 | 24.14 |
| 1874 | N | TYR | 1131 | 73.898 | 57.988 | 45.360 | 1.00 | 23.40 |
| 1875 | CA | TYR | 1131 | 74.928 | 57.423 | 46.225 | 1.00 | 22.86 |
| 1876 | CB | TYR | 1131 | 75.039 | 55.924 | 45.980 | 1.00 | 22.51 |
| 1877 | CG | TYR | 1131 | 73.719 | 55.224 | 46.135 | 1.00 | 21.96 |
| 1878 | CD1 | TYR | 1131 | 72.923 | 54.955 | 45.034 | 1.00 | 21.81 |
| 1879 | CE1 | TYR | 1131 | 71.671 | 54.382 | 45.176 | 1.00 | 22.83 |
| 1880 | CD2 | TYR | 1131 | 73.234 | 54.893 | 47.393 | 1.00 | 24.12 |
| 1881 | CE2 | TYR | 1131 | 71.985 | 54.318 | 47.551 | 1.00 | 24.94 |
| 1882 | CZ | TYR | 1131 | 71.205 | 54.065 | 46.437 | 1.00 | 24.69 |
| 1883 | OH | TYR | 1131 | 69.951 | 53.504 | 46.590 | 1.00 | 26.44 |
| 1884 | C | TYR | 1131 | 76.268 | 58.108 | 45.965 | 1.00 | 22.03 |
| 1885 | O | TYR | 1131 | 76.773 | 58.088 | 44.847 | 1.00 | 22.92 |
| 1886 | N | LEU | 1132 | 76.809 | 58.737 | 47.003 | 1.00 | 21.21 |

FIG. 3A-42

| Atom | Atom Type | Resid | # | X | Y | Z | OCC | B |
|---|---|---|---|---|---|---|---|---|
| 1887 | CA | LEU | 1132 | 78.071 | 59.463 | 46.956 | 1.00 | 20.60 |
| 1888 | CB | LEU | 1132 | 78.032 | 60.576 | 48.007 | 1.00 | 21.28 |
| 1889 | CG | LEU | 1132 | 78.843 | 61.874 | 47.906 | 1.00 | 23.35 |
| 1890 | CD1 | LEU | 1132 | 78.614 | 62.661 | 49.172 | 1.00 | 25.61 |
| 1891 | CD2 | LEU | 1132 | 80.319 | 61.623 | 47.741 | 1.00 | 26.41 |
| 1892 | C | LEU | 1132 | 79.249 | 58.541 | 47.263 | 1.00 | 20.51 |
| 1893 | O | LEU | 1132 | 79.250 | 57.853 | 48.283 | 1.00 | 23.83 |
| 1894 | N | VAL | 1133 | 80.246 | 58.524 | 46.386 | 1.00 | 18.28 |
| 1895 | CA | VAL | 1133 | 81.438 | 57.714 | 46.592 | 1.00 | 16.12 |
| 1896 | CB | VAL | 1133 | 81.912 | 57.067 | 45.284 | 1.00 | 14.27 |
| 1897 | CG1 | VAL | 1133 | 83.198 | 56.291 | 45.516 | 1.00 | 11.21 |
| 1898 | CG2 | VAL | 1133 | 80.821 | 56.165 | 44.722 | 1.00 | 9.93 |
| 1899 | C | VAL | 1133 | 82.538 | 58.635 | 47.130 | 1.00 | 20.05 |
| 1900 | O | VAL | 1133 | 83.051 | 59.504 | 46.411 | 1.00 | 18.89 |
| 1901 | N | THR | 1134 | 82.861 | 58.471 | 48.410 | 1.00 | 21.68 |
| 1902 | CA | THR | 1134 | 83.876 | 59.286 | 49.061 | 1.00 | 21.80 |
| 1903 | CB | THR | 1134 | 83.741 | 59.227 | 50.584 | 1.00 | 19.89 |
| 1904 | OG1 | THR | 1134 | 84.183 | 57.946 | 51.043 | 1.00 | 21.40 |
| 1905 | CG2 | THR | 1134 | 82.292 | 59.428 | 50.999 | 1.00 | 18.10 |
| 1906 | C | THR | 1134 | 85.296 | 58.872 | 48.705 | 1.00 | 24.10 |
| 1907 | O | THR | 1134 | 85.530 | 57.792 | 48.166 | 1.00 | 24.71 |
| 1908 | N | ARG | 1135 | 86.245 | 59.719 | 49.083 | 1.00 | 26.05 |
| 1909 | CA | ARG | 1135 | 87.665 | 59.488 | 48.840 | 1.00 | 28.72 |
| 1910 | CB | ARG | 1135 | 88.472 | 60.667 | 49.386 | 1.00 | 32.63 |
| 1911 | CG | ARG | 1135 | 89.950 | 60.546 | 49.160 | 1.00 | 35.08 |
| 1912 | CD | ARG | 1135 | 90.705 | 61.556 | 49.968 | 1.00 | 39.19 |
| 1913 | NE | ARG | 1135 | 92.134 | 61.292 | 49.896 | 1.00 | 46.35 |
| 1914 | CZ | ARG | 1135 | 93.018 | 61.704 | 50.798 | 1.00 | 53.28 |
| 1915 | NH1 | ARG | 1135 | 94.305 | 61.414 | 50.643 | 1.00 | 56.95 |
| 1916 | NH2 | ARG | 1135 | 92.618 | 62.396 | 51.862 | 1.00 | 57.23 |
| 1917 | C | ARG | 1135 | 88.173 | 58.202 | 49.487 | 1.00 | 27.12 |
| 1918 | O | ARG | 1135 | 89.205 | 57.668 | 49.094 | 1.00 | 28.70 |
| 1919 | N | HIS | 1136 | 87.471 | 57.732 | 50.508 | 1.00 | 26.02 |
| 1920 | CA | HIS | 1136 | 87.875 | 56.517 | 51.201 | 1.00 | 25.17 |
| 1921 | CB | HIS | 1136 | 87.613 | 56.649 | 52.695 | 1.00 | 27.11 |
| 1922 | CG | HIS | 1136 | 88.126 | 57.929 | 53.272 | 1.00 | 33.56 |
| 1923 | CD2 | HIS | 1136 | 87.473 | 59.032 | 53.704 | 1.00 | 37.55 |
| 1924 | ND1 | HIS | 1136 | 89.473 | 58.206 | 53.392 | 1.00 | 35.53 |
| 1925 | CE1 | HIS | 1136 | 89.626 | 59.429 | 53.869 | 1.00 | 38.38 |
| 1926 | NE2 | HIS | 1136 | 88.429 | 59.954 | 54.068 | 1.00 | 39.18 |
| 1927 | C | HIS | 1136 | 87.150 | 55.306 | 50.645 | 1.00 | 24.36 |
| 1928 | O | HIS | 1136 | 87.172 | 54.236 | 51.252 | 1.00 | 24.55 |
| 1929 | N | ALA | 1137 | 86.522 | 55.480 | 49.485 | 1.00 | 21.92 |
| 1930 | CA | ALA | 1137 | 85.796 | 54.413 | 48.823 | 1.00 | 20.47 |
| 1931 | CB | ALA | 1137 | 86.728 | 53.257 | 48.511 | 1.00 | 20.48 |
| 1932 | C | ALA | 1137 | 84.588 | 53.934 | 49.623 | 1.00 | 21.30 |
| 1933 | O | ALA | 1137 | 84.316 | 52.734 | 49.719 | 1.00 | 22.24 |
| 1934 | N | ASP | 1138 | 83.876 | 54.880 | 50.218 | 1.00 | 21.09 |
| 1935 | CA | ASP | 1138 | 82.674 | 54.569 | 50.973 | 1.00 | 21.30 |

FIG. 3A-43

| Atom | Atom Type | Resid | # | X | Y | Z | OCC | B |
|---|---|---|---|---|---|---|---|---|
| 1936 | CB | ASP | 1138 | 82.662 | 55.283 | 52.325 | 1.00 | 20.40 |
| 1937 | CG | ASP | 1138 | 83.685 | 54.731 | 53.291 | 1.00 | 20.82 |
| 1938 | OD1 | ASP | 1138 | 83.890 | 53.501 | 53.319 | 1.00 | 23.51 |
| 1939 | OD2 | ASP | 1138 | 84.287 | 55.527 | 54.034 | 1.00 | 23.93 |
| 1940 | C | ASP | 1138 | 81.537 | 55.097 | 50.119 | 1.00 | 23.33 |
| 1941 | O | ASP | 1138 | 81.646 | 56.183 | 49.546 | 1.00 | 25.82 |
| 1942 | N | VAL | 1139 | 80.468 | 54.320 | 50.003 | 1.00 | 23.72 |
| 1943 | CA | VAL | 1139 | 79.305 | 54.702 | 49.214 | 1.00 | 20.95 |
| 1944 | CB | VAL | 1139 | 78.779 | 53.501 | 48.415 | 1.00 | 18.28 |
| 1945 | CG1 | VAL | 1139 | 77.527 | 53.875 | 47.661 | 1.00 | 15.80 |
| 1946 | CG2 | VAL | 1139 | 79.857 | 52.982 | 47.481 | 1.00 | 12.00 |
| 1947 | C | VAL | 1139 | 78.251 | 55.125 | 50.208 | 1.00 | 22.42 |
| 1948 | O | VAL | 1139 | 77.814 | 54.316 | 51.017 | 1.00 | 25.81 |
| 1949 | N | ILE | 1140 | 77.862 | 56.389 | 50.188 | 1.00 | 23.66 |
| 1950 | CA | ILE | 1140 | 76.854 | 56.863 | 51.130 | 1.00 | 25.17 |
| 1951 | CB | ILE | 1140 | 77.449 | 57.935 | 52.089 | 1.00 | 26.79 |
| 1952 | CG2 | ILE | 1140 | 78.669 | 57.368 | 52.805 | 1.00 | 27.35 |
| 1953 | CG1 | ILE | 1140 | 77.887 | 59.188 | 51.330 | 1.00 | 28.07 |
| 1954 | CD1 | ILE | 1140 | 78.560 | 60.238 | 52.219 | 1.00 | 27.71 |
| 1955 | C | ILE | 1140 | 75.607 | 57.375 | 50.408 | 1.00 | 25.17 |
| 1956 | O | ILE | 1140 | 75.717 | 58.102 | 49.433 | 1.00 | 25.94 |
| 1957 | N | PRO | 1141 | 74.406 | 56.943 | 50.834 | 1.00 | 25.23 |
| 1958 | CD | PRO | 1141 | 74.102 | 56.065 | 51.974 | 1.00 | 26.31 |
| 1959 | CA | PRO | 1141 | 73.167 | 57.388 | 50.189 | 1.00 | 26.02 |
| 1960 | CB | PRO | 1141 | 72.099 | 56.552 | 50.887 | 1.00 | 26.05 |
| 1961 | CG | PRO | 1141 | 72.647 | 56.404 | 52.253 | 1.00 | 26.71 |
| 1962 | C | PRO | 1141 | 72.912 | 58.874 | 50.384 | 1.00 | 27.84 |
| 1963 | O | PRO | 1141 | 73.231 | 59.440 | 51.432 | 1.00 | 29.15 |
| 1964 | N | VAL | 1142 | 72.289 | 59.483 | 49.383 | 1.00 | 28.51 |
| 1965 | CA | VAL | 1142 | 71.973 | 60.902 | 49.385 | 1.00 | 27.59 |
| 1966 | CB | VAL | 1142 | 73.080 | 61.695 | 48.640 | 1.00 | 26.82 |
| 1967 | CG1 | VAL | 1142 | 72.710 | 63.160 | 48.504 | 1.00 | 25.54 |
| 1968 | CG2 | VAL | 1142 | 74.398 | 61.554 | 49.368 | 1.00 | 24.22 |
| 1969 | C | VAL | 1142 | 70.650 | 61.047 | 48.640 | 1.00 | 30.42 |
| 1970 | O | VAL | 1142 | 70.465 | 60.445 | 47.575 | 1.00 | 31.72 |
| 1971 | N | ARG | 1143 | 69.708 | 61.788 | 49.220 | 1.00 | 32.81 |
| 1972 | CA | ARG | 1143 | 68.411 | 62.006 | 48.580 | 1.00 | 33.55 |
| 1973 | CB | ARG | 1143 | 67.282 | 62.037 | 49.613 | 1.00 | 35.71 |
| 1974 | CG | ARG | 1143 | 65.903 | 62.331 | 49.017 | 1.00 | 37.69 |
| 1975 | CD | ARG | 1143 | 65.465 | 61.288 | 47.991 | 1.00 | 39.30 |
| 1976 | NE | ARG | 1143 | 64.225 | 61.685 | 47.311 | 1.00 | 43.20 |
| 1977 | CZ | ARG | 1143 | 63.383 | 60.843 | 46.711 | 1.00 | 43.40 |
| 1978 | NH1 | ARG | 1143 | 63.628 | 59.539 | 46.696 | 1.00 | 43.88 |
| 1979 | NH2 | ARG | 1143 | 62.297 | 61.307 | 46.108 | 1.00 | 43.09 |
| 1980 | C | ARG | 1143 | 68.439 | 63.320 | 47.818 | 1.00 | 33.27 |
| 1981 | O | ARG | 1143 | 68.794 | 64.353 | 48.382 | 1.00 | 33.50 |
| 1982 | N | ARG | 1144 | 68.044 | 63.280 | 46.549 | 1.00 | 33.18 |
| 1983 | CA | ARG | 1144 | 68.038 | 64.471 | 45.709 | 1.00 | 34.20 |
| 1984 | CB | ARG | 1144 | 67.725 | 64.089 | 44.260 | 1.00 | 32.94 |

FIG. 3A-44

| Atom | Atom Type | Resid | # | X | Y | Z | OCC | B |
|---|---|---|---|---|---|---|---|---|
| 1985 | CG | ARG | 1144 | 68.475 | 64.900 | 43.203 | 1.00 | 32.47 |
| 1986 | CD | ARG | 1144 | 67.952 | 64.546 | 41.815 | 1.00 | 32.92 |
| 1987 | NE | ARG | 1144 | 68.924 | 64.732 | 40.738 | 1.00 | 33.75 |
| 1988 | CZ | ARG | 1144 | 69.459 | 65.898 | 40.387 | 1.00 | 35.07 |
| 1989 | NH1 | ARG | 1144 | 69.125 | 67.007 | 41.029 | 1.00 | 36.60 |
| 1990 | NH2 | ARG | 1144 | 70.321 | 65.959 | 39.378 | 1.00 | 35.64 |
| 1991 | C | ARG | 1144 | 67.001 | 65.467 | 46.227 | 1.00 | 35.48 |
| 1992 | O | ARG | 1144 | 65.825 | 65.139 | 46.374 | 1.00 | 36.95 |
| 1993 | N | ARG | 1145 | 67.449 | 66.670 | 46.546 | 1.00 | 36.40 |
| 1994 | CA | ARG | 1145 | 66.552 | 67.700 | 47.048 | 1.00 | 37.95 |
| 1995 | CB | ARG | 1145 | 67.025 | 68.213 | 48.414 | 1.00 | 37.18 |
| 1996 | CG | ARG | 1145 | 66.975 | 67.184 | 49.514 | 1.00 | 36.94 |
| 1997 | CD | ARG | 1145 | 65.570 | 66.667 | 49.681 | 1.00 | 38.43 |
| 1998 | NE | ARG | 1145 | 65.447 | 65.729 | 50.791 | 1.00 | 41.86 |
| 1999 | CZ | ARG | 1145 | 64.341 | 65.043 | 51.062 | 1.00 | 43.83 |
| 2000 | NH1 | ARG | 1145 | 63.263 | 65.187 | 50.299 | 1.00 | 46.04 |
| 2001 | NH2 | ARG | 1145 | 64.306 | 64.223 | 52.102 | 1.00 | 45.68 |
| 2002 | C | ARG | 1145 | 66.507 | 68.856 | 46.063 | 1.00 | 39.67 |
| 2003 | O | ARG | 1145 | 66.247 | 70.000 | 46.449 | 1.00 | 42.26 |
| 2004 | N | GLY | 1146 | 66.789 | 68.565 | 44.797 | 1.00 | 39.96 |
| 2005 | CA | GLY | 1146 | 66.779 | 69.605 | 43.788 | 1.00 | 40.13 |
| 2006 | C | GLY | 1146 | 67.932 | 69.428 | 42.823 | 1.00 | 40.68 |
| 2007 | O | GLY | 1146 | 68.829 | 68.621 | 43.061 | 1.00 | 41.79 |
| 2008 | N | ALA | 1147 | 67.937 | 70.228 | 41.765 | 1.00 | 40.55 |
| 2009 | CA | ALA | 1147 | 68.961 | 70.157 | 40.733 | 1.00 | 39.49 |
| 2010 | CB | ALA | 1147 | 68.890 | 71.392 | 39.834 | 1.00 | 40.92 |
| 2011 | C | ALA | 1147 | 70.392 | 69.927 | 41.214 | 1.00 | 38.50 |
| 2012 | O | ALA | 1147 | 71.068 | 69.024 | 40.717 | 1.00 | 38.36 |
| 2013 | N | SER | 1148 | 70.854 | 70.721 | 42.176 | 1.00 | 37.84 |
| 2014 | CA | SER | 1148 | 72.222 | 70.564 | 42.656 | 1.00 | 36.96 |
| 2015 | CB | SER | 1148 | 73.097 | 71.732 | 42.182 | 1.00 | 36.77 |
| 2016 | OG | SER | 1148 | 72.690 | 72.965 | 42.755 | 1.00 | 40.56 |
| 2017 | C | SER | 1148 | 72.391 | 70.363 | 44.156 | 1.00 | 36.04 |
| 2018 | O | SER | 1148 | 73.382 | 70.812 | 44.734 | 1.00 | 36.47 |
| 2019 | N | ARG | 1149 | 71.452 | 69.672 | 44.788 | 1.00 | 34.56 |
| 2020 | CA | ARG | 1149 | 71.575 | 69.416 | 46.214 | 1.00 | 33.98 |
| 2021 | CB | ARG | 1149 | 70.923 | 70.518 | 47.050 | 1.00 | 35.91 |
| 2022 | CG | ARG | 1149 | 71.621 | 70.740 | 48.397 | 1.00 | 40.83 |
| 2023 | CD | ARG | 1149 | 70.760 | 71.514 | 49.389 | 1.00 | 44.70 |
| 2024 | NE | ARG | 1149 | 71.544 | 72.142 | 50.456 | 1.00 | 48.33 |
| 2025 | CZ | ARG | 1149 | 71.832 | 73.444 | 50.506 | 1.00 | 50.37 |
| 2026 | NH1 | ARG | 1149 | 71.416 | 74.266 | 49.552 | 1.00 | 52.98 |
| 2027 | NH2 | ARG | 1149 | 72.508 | 73.941 | 51.531 | 1.00 | 51.44 |
| 2028 | C | ARG | 1149 | 70.981 | 68.070 | 46.573 | 1.00 | 32.53 |
| 2029 | O | ARG | 1149 | 70.168 | 67.513 | 45.833 | 1.00 | 32.88 |
| 2030 | N | GLY | 1150 | 71.418 | 67.541 | 47.705 | 1.00 | 31.86 |
| 2031 | CA | GLY | 1150 | 70.934 | 66.260 | 48.171 | 1.00 | 29.91 |
| 2032 | C | GLY | 1150 | 71.207 | 66.138 | 49.653 | 1.00 | 28.10 |
| 2033 | O | GLY | 1150 | 72.237 | 66.603 | 50.137 | 1.00 | 29.55 |

FIG. 3A-45

| Atom | Atom Type | Resid | # | X | Y | Z | OCC | B |
|---|---|---|---|---|---|---|---|---|
| 2034 | N | SER | 1151 | 70.289 | 65.516 | 50.376 | 1.00 | 27.99 |
| 2035 | CA | SER | 1151 | 70.439 | 65.348 | 51.811 | 1.00 | 28.25 |
| 2036 | CB | SER | 1151 | 69.072 | 65.434 | 52.487 | 1.00 | 31.79 |
| 2037 | OG | SER | 1151 | 68.433 | 66.664 | 52.201 | 1.00 | 39.70 |
| 2038 | C | SER | 1151 | 71.071 | 64.020 | 52.164 | 1.00 | 26.53 |
| 2039 | O | SER | 1151 | 70.653 | 62.974 | 51.662 | 1.00 | 25.17 |
| 2040 | N | LEU | 1152 | 72.089 | 64.055 | 53.013 | 1.00 | 25.87 |
| 2041 | CA | LEU | 1152 | 72.706 | 62.814 | 53.443 | 1.00 | 27.78 |
| 2042 | CB | LEU | 1152 | 73.948 | 63.075 | 54.296 | 1.00 | 26.21 |
| 2043 | CG | LEU | 1152 | 75.157 | 63.729 | 53.627 | 1.00 | 24.51 |
| 2044 | CD1 | LEU | 1152 | 76.335 | 63.659 | 54.564 | 1.00 | 23.77 |
| 2045 | CD2 | LEU | 1152 | 75.496 | 63.008 | 52.343 | 1.00 | 25.98 |
| 2046 | C | LEU | 1152 | 71.629 | 62.147 | 54.287 | 1.00 | 29.68 |
| 2047 | O | LEU | 1152 | 70.965 | 62.819 | 55.075 | 1.00 | 31.97 |
| 2048 | N | LEU | 1153 | 71.385 | 60.860 | 54.065 | 1.00 | 31.23 |
| 2049 | CA | LEU | 1153 | 70.372 | 60.159 | 54.845 | 1.00 | 31.26 |
| 2050 | CB | LEU | 1153 | 69.991 | 58.836 | 54.181 | 1.00 | 29.73 |
| 2051 | CG | LEU | 1153 | 68.811 | 58.932 | 53.215 | 1.00 | 27.81 |
| 2052 | CD1 | LEU | 1153 | 69.023 | 60.036 | 52.193 | 1.00 | 29.89 |
| 2053 | CD2 | LEU | 1153 | 68.619 | 57.614 | 52.528 | 1.00 | 28.98 |
| 2054 | C | LEU | 1153 | 70.862 | 59.933 | 56.269 | 1.00 | 33.19 |
| 2055 | O | LEU | 1153 | 70.075 | 59.670 | 57.182 | 1.00 | 34.12 |
| 2056 | N | SER | 1154 | 72.166 | 60.072 | 56.459 | 1.00 | 34.74 |
| 2057 | CA | SER | 1154 | 72.775 | 59.899 | 57.762 | 1.00 | 37.99 |
| 2058 | CB | SER | 1154 | 73.331 | 58.483 | 57.903 | 1.00 | 40.16 |
| 2059 | OG | SER | 1154 | 72.446 | 57.531 | 57.326 | 1.00 | 44.40 |
| 2060 | C | SER | 1154 | 73.910 | 60.907 | 57.871 | 1.00 | 38.37 |
| 2061 | O | SER | 1154 | 74.946 | 60.743 | 57.236 | 1.00 | 38.18 |
| 2062 | N | PRO | 1155 | 73.694 | 62.005 | 58.622 | 1.00 | 38.99 |
| 2063 | CD | PRO | 1155 | 72.505 | 62.296 | 59.437 | 1.00 | 39.19 |
| 2064 | CA | PRO | 1155 | 74.708 | 63.045 | 58.805 | 1.00 | 38.38 |
| 2065 | CB | PRO | 1155 | 74.098 | 63.942 | 59.875 | 1.00 | 38.04 |
| 2066 | CG | PRO | 1155 | 73.120 | 63.040 | 60.584 | 1.00 | 40.36 |
| 2067 | C | PRO | 1155 | 76.048 | 62.479 | 59.245 | 1.00 | 37.35 |
| 2068 | O | PRO | 1155 | 76.121 | 61.531 | 60.044 | 1.00 | 36.59 |
| 2069 | N | ARG | 1156 | 77.104 | 63.088 | 58.732 | 1.00 | 36.29 |
| 2070 | CA | ARG | 1156 | 78.456 | 62.654 | 59.023 | 1.00 | 35.23 |
| 2071 | CB | ARG | 1156 | 79.031 | 61.956 | 57.803 | 1.00 | 38.13 |
| 2072 | CG | ARG | 1156 | 78.185 | 60.870 | 57.211 | 1.00 | 41.38 |
| 2073 | CD | ARG | 1156 | 78.700 | 59.509 | 57.644 | 1.00 | 44.77 |
| 2074 | NE | ARG | 1156 | 78.123 | 58.412 | 56.868 | 1.00 | 49.49 |
| 2075 | CZ | ARG | 1156 | 78.459 | 57.129 | 57.005 | 1.00 | 53.79 |
| 2076 | NH1 | ARG | 1156 | 77.873 | 56.205 | 56.252 | 1.00 | 54.43 |
| 2077 | NH2 | ARG | 1156 | 79.403 | 56.763 | 57.863 | 1.00 | 52.82 |
| 2078 | C | ARG | 1156 | 79.340 | 63.849 | 59.255 | 1.00 | 34.55 |
| 2079 | O | ARG | 1156 | 79.066 | 64.939 | 58.756 | 1.00 | 35.72 |
| 2080 | N | PRO | 1157 | 80.443 | 63.673 | 59.989 | 1.00 | 34.18 |
| 2081 | CD | PRO | 1157 | 80.899 | 62.473 | 60.707 | 1.00 | 33.27 |
| 2082 | CA | PRO | 1157 | 81.344 | 64.798 | 60.233 | 1.00 | 33.99 |

FIG. 3A-46

| Atom | Atom Type | Resid | # | X | Y | Z | OCC | B |
|------|-----------|-------|---|-------|-------|-------|------|-------|
| 2083 | CB | PRO | 1157 | 82.419 | 64.167 | 61.111 | 1.00 | 33.27 |
| 2084 | CG | PRO | 1157 | 81.690 | 63.074 | 61.803 | 1.00 | 32.25 |
| 2085 | C | PRO | 1157 | 81.950 | 65.234 | 58.898 | 1.00 | 35.59 |
| 2086 | O | PRO | 1157 | 82.404 | 64.393 | 58.130 | 1.00 | 37.92 |
| 2087 | N | ILE | 1158 | 81.999 | 66.527 | 58.631 | 1.00 | 36.57 |
| 2088 | CA | ILE | 1158 | 82.542 | 67.000 | 57.362 | 1.00 | 38.10 |
| 2089 | CB | ILE | 1158 | 82.647 | 68.533 | 57.315 | 1.00 | 38.12 |
| 2090 | CG2 | ILE | 1158 | 81.272 | 69.140 | 57.171 | 1.00 | 37.34 |
| 2091 | CG1 | ILE | 1158 | 83.342 | 69.046 | 58.573 | 1.00 | 41.61 |
| 2092 | CD1 | ILE | 1158 | 83.623 | 70.540 | 58.559 | 1.00 | 45.60 |
| 2093 | C | ILE | 1158 | 83.911 | 66.408 | 57.004 | 1.00 | 39.96 |
| 2094 | O | ILE | 1158 | 84.280 | 66.367 | 55.828 | 1.00 | 41.17 |
| 2095 | N | SER | 1159 | 84.642 | 65.941 | 58.014 | 1.00 | 40.39 |
| 2096 | CA | SER | 1159 | 85.959 | 65.341 | 57.813 | 1.00 | 42.66 |
| 2097 | CB | SER | 1159 | 86.575 | 64.975 | 59.161 | 1.00 | 45.98 |
| 2098 | OG | SER | 1159 | 85.755 | 64.035 | 59.842 | 1.00 | 49.77 |
| 2099 | C | SER | 1159 | 85.870 | 64.078 | 56.955 | 1.00 | 42.30 |
| 2100 | O | SER | 1159 | 86.779 | 63.761 | 56.183 | 1.00 | 43.56 |
| 2101 | N | TYR | 1160 | 84.779 | 63.346 | 57.130 | 1.00 | 40.66 |
| 2102 | CA | TYR | 1160 | 84.531 | 62.121 | 56.385 | 1.00 | 40.36 |
| 2103 | CB | TYR | 1160 | 83.137 | 61.598 | 56.756 | 1.00 | 43.66 |
| 2104 | CG | TYR | 1160 | 82.848 | 60.149 | 56.423 | 1.00 | 47.75 |
| 2105 | CD1 | TYR | 1160 | 82.086 | 59.377 | 57.290 | 1.00 | 50.46 |
| 2106 | CE1 | TYR | 1160 | 81.763 | 58.059 | 56.991 | 1.00 | 53.68 |
| 2107 | CD2 | TYR | 1160 | 83.293 | 59.561 | 55.233 | 1.00 | 49.34 |
| 2108 | CE2 | TYR | 1160 | 82.975 | 58.237 | 54.922 | 1.00 | 51.68 |
| 2109 | CZ | TYR | 1160 | 82.205 | 57.493 | 55.809 | 1.00 | 53.15 |
| 2110 | OH | TYR | 1160 | 81.858 | 56.185 | 55.528 | 1.00 | 54.20 |
| 2111 | C | TYR | 1160 | 84.563 | 62.464 | 54.901 | 1.00 | 37.91 |
| 2112 | O | TYR | 1160 | 85.111 | 61.715 | 54.080 | 1.00 | 38.62 |
| 2113 | N | LEU | 1161 | 84.020 | 63.632 | 54.578 | 1.00 | 34.26 |
| 2114 | CA | LEU | 1161 | 83.932 | 64.086 | 53.203 | 1.00 | 30.68 |
| 2115 | CB | LEU | 1161 | 82.639 | 64.889 | 53.018 | 1.00 | 27.49 |
| 2116 | CG | LEU | 1161 | 81.344 | 64.152 | 53.394 | 1.00 | 25.85 |
| 2117 | CD1 | LEU | 1161 | 80.168 | 65.085 | 53.276 | 1.00 | 25.64 |
| 2118 | CD2 | LEU | 1161 | 81.135 | 62.931 | 52.516 | 1.00 | 23.54 |
| 2119 | C | LEU | 1161 | 85.148 | 64.852 | 52.675 | 1.00 | 30.40 |
| 2120 | O | LEU | 1161 | 85.242 | 65.106 | 51.473 | 1.00 | 31.18 |
| 2121 | N | ALA | 1162 | 86.094 | 65.189 | 53.545 | 1.00 | 29.45 |
| 2122 | CA | ALA | 1162 | 87.283 | 65.919 | 53.101 | 1.00 | 29.15 |
| 2123 | CB | ALA | 1162 | 88.222 | 66.214 | 54.281 | 1.00 | 29.64 |
| 2124 | C | ALA | 1162 | 88.024 | 65.140 | 52.015 | 1.00 | 27.83 |
| 2125 | O | ALA | 1162 | 88.278 | 63.937 | 52.150 | 1.00 | 28.97 |
| 2126 | N | GLY | 1163 | 88.324 | 65.830 | 50.922 | 1.00 | 26.09 |
| 2127 | CA | GLY | 1163 | 89.032 | 65.216 | 49.816 | 1.00 | 24.79 |
| 2128 | C | GLY | 1163 | 88.127 | 64.490 | 48.845 | 1.00 | 22.40 |
| 2129 | O | GLY | 1163 | 88.607 | 63.799 | 47.958 | 1.00 | 22.88 |
| 2130 | N | SER | 1164 | 86.819 | 64.667 | 48.978 | 1.00 | 23.08 |
| 2131 | CA | SER | 1164 | 85.887 | 63.988 | 48.091 | 1.00 | 23.47 |

FIG. 3A-47

| Atom | Atom Type | Resid | # | X | Y | Z | OCC | B |
|---|---|---|---|---|---|---|---|---|
| 2132 | CB | SER | 1164 | 84.765 | 63.336 | 48.893 | 1.00 | 22.44 |
| 2133 | OG | SER | 1164 | 85.308 | 62.418 | 49.833 | 1.00 | 24.67 |
| 2134 | C | SER | 1164 | 85.314 | 64.853 | 46.984 | 1.00 | 23.93 |
| 2135 | O | SER | 1164 | 84.470 | 64.389 | 46.229 | 1.00 | 25.83 |
| 2136 | N | SER | 1165 | 85.762 | 66.102 | 46.877 | 1.00 | 24.65 |
| 2137 | CA | SER | 1165 | 85.271 | 66.981 | 45.815 | 1.00 | 24.90 |
| 2138 | CB | SER | 1165 | 85.812 | 68.401 | 45.981 | 1.00 | 26.62 |
| 2139 | OG | SER | 1165 | 85.674 | 68.850 | 47.316 | 1.00 | 33.09 |
| 2140 | C | SER | 1165 | 85.756 | 66.423 | 44.487 | 1.00 | 22.54 |
| 2141 | O | SER | 1165 | 86.942 | 66.152 | 44.327 | 1.00 | 22.12 |
| 2142 | N | GLY | 1166 | 84.843 | 66.286 | 43.533 | 1.00 | 21.99 |
| 2143 | CA | GLY | 1166 | 85.184 | 65.741 | 42.232 | 1.00 | 19.49 |
| 2144 | C | GLY | 1166 | 84.745 | 64.288 | 42.122 | 1.00 | 20.47 |
| 2145 | O | GLY | 1166 | 84.756 | 63.720 | 41.033 | 1.00 | 19.68 |
| 2146 | N | GLY | 1167 | 84.388 | 63.684 | 43.258 | 1.00 | 20.15 |
| 2147 | CA | GLY | 1167 | 83.928 | 62.303 | 43.294 | 1.00 | 20.19 |
| 2148 | C | GLY | 1167 | 82.534 | 62.182 | 42.712 | 1.00 | 20.08 |
| 2149 | O | GLY | 1167 | 81.798 | 63.161 | 42.698 | 1.00 | 21.88 |
| 2150 | N | PRO | 1168 | 82.109 | 60.986 | 42.297 | 1.00 | 20.02 |
| 2151 | CD | PRO | 1168 | 82.901 | 59.746 | 42.208 | 1.00 | 20.29 |
| 2152 | CA | PRO | 1168 | 80.786 | 60.792 | 41.710 | 1.00 | 19.44 |
| 2153 | CB | PRO | 1168 | 81.002 | 59.553 | 40.851 | 1.00 | 21.21 |
| 2154 | CG | PRO | 1168 | 81.880 | 58.729 | 41.726 | 1.00 | 18.35 |
| 2155 | C | PRO | 1168 | 79.578 | 60.595 | 42.611 | 1.00 | 19.51 |
| 2156 | O | PRO | 1168 | 79.683 | 60.068 | 43.712 | 1.00 | 20.28 |
| 2157 | N | LEU | 1169 | 78.427 | 61.050 | 42.123 | 1.00 | 19.50 |
| 2158 | CA | LEU | 1169 | 77.149 | 60.852 | 42.798 | 1.00 | 20.76 |
| 2159 | CB | LEU | 1169 | 76.376 | 62.152 | 42.977 | 1.00 | 18.93 |
| 2160 | CG | LEU | 1169 | 76.583 | 62.721 | 44.372 | 1.00 | 17.23 |
| 2161 | CD1 | LEU | 1169 | 77.483 | 63.924 | 44.272 | 1.00 | 17.53 |
| 2162 | CD2 | LEU | 1169 | 75.255 | 63.072 | 44.991 | 1.00 | 16.81 |
| 2163 | C | LEU | 1169 | 76.444 | 59.952 | 41.807 | 1.00 | 21.18 |
| 2164 | O | LEU | 1169 | 76.098 | 60.381 | 40.708 | 1.00 | 23.71 |
| 2165 | N | LEU | 1170 | 76.336 | 58.680 | 42.153 | 1.00 | 21.28 |
| 2166 | CA | LEU | 1170 | 75.736 | 57.702 | 41.267 | 1.00 | 21.46 |
| 2167 | CB | LEU | 1170 | 76.527 | 56.398 | 41.356 | 1.00 | 17.58 |
| 2168 | CG | LEU | 1170 | 78.027 | 56.488 | 41.086 | 1.00 | 15.37 |
| 2169 | CD1 | LEU | 1170 | 78.700 | 55.235 | 41.566 | 1.00 | 13.10 |
| 2170 | CD2 | LEU | 1170 | 78.284 | 56.702 | 39.616 | 1.00 | 12.53 |
| 2171 | C | LEU | 1170 | 74.265 | 57.416 | 41.529 | 1.00 | 24.11 |
| 2172 | O | LEU | 1170 | 73.783 | 57.534 | 42.656 | 1.00 | 27.04 |
| 2173 | N | CYS | 1171 | 73.540 | 57.104 | 40.466 | 1.00 | 23.89 |
| 2174 | CA | CYS | 1171 | 72.142 | 56.747 | 40.592 | 1.00 | 26.02 |
| 2175 | CB | CYS | 1171 | 71.421 | 56.978 | 39.265 | 1.00 | 26.82 |
| 2176 | SG | CYS | 1171 | 71.658 | 55.657 | 38.066 | 1.00 | 28.93 |
| 2177 | C | CYS | 1171 | 72.209 | 55.250 | 40.918 | 1.00 | 27.13 |
| 2178 | O | CYS | 1171 | 73.285 | 54.648 | 40.840 | 1.00 | 28.91 |
| 2179 | N | PRO | 1172 | 71.069 | 54.616 | 41.243 | 1.00 | 27.20 |
| 2180 | CD | PRO | 1172 | 69.735 | 55.217 | 41.411 | 1.00 | 26.50 |

FIG. 3A-48

| Atom | Atom Type | Resid | # | X | Y | Z | OCC | B |
|---|---|---|---|---|---|---|---|---|
| 2181 | CA | PRO | 1172 | 71.033 | 53.185 | 41.574 | 1.00 | 25.65 |
| 2182 | CB | PRO | 1172 | 69.538 | 52.912 | 41.707 | 1.00 | 25.61 |
| 2183 | CG | PRO | 1172 | 69.031 | 54.192 | 42.263 | 1.00 | 28.15 |
| 2184 | C | PRO | 1172 | 71.681 | 52.239 | 40.558 | 1.00 | 25.57 |
| 2185 | O | PRO | 1172 | 72.227 | 51.198 | 40.933 | 1.00 | 26.76 |
| 2186 | N | ALA | 1173 | 71.606 | 52.576 | 39.277 | 1.00 | 25.34 |
| 2187 | CA | ALA | 1173 | 72.193 | 51.729 | 38.244 | 1.00 | 25.38 |
| 2188 | CB | ALA | 1173 | 71.454 | 51.915 | 36.936 | 1.00 | 25.17 |
| 2189 | C | ALA | 1173 | 73.678 | 51.997 | 38.042 | 1.00 | 27.51 |
| 2190 | O | ALA | 1173 | 74.279 | 51.483 | 37.095 | 1.00 | 29.05 |
| 2191 | N | GLY | 1174 | 74.253 | 52.849 | 38.890 | 1.00 | 27.48 |
| 2192 | CA | GLY | 1174 | 75.668 | 53.166 | 38.787 | 1.00 | 27.28 |
| 2193 | C | GLY | 1174 | 76.035 | 54.129 | 37.673 | 1.00 | 26.52 |
| 2194 | O | GLY | 1174 | 77.103 | 54.029 | 37.076 | 1.00 | 27.07 |
| 2195 | N | HIS | 1175 | 75.140 | 55.047 | 37.353 | 1.00 | 25.55 |
| 2196 | CA | HIS | 1175 | 75.427 | 56.016 | 36.312 | 1.00 | 25.00 |
| 2197 | CB | HIS | 1175 | 74.313 | 56.027 | 35.281 | 1.00 | 26.94 |
| 2198 | CG | HIS | 1175 | 74.268 | 54.783 | 34.458 | 1.00 | 27.86 |
| 2199 | CD2 | HIS | 1175 | 74.317 | 54.598 | 33.121 | 1.00 | 30.29 |
| 2200 | ND1 | HIS | 1175 | 74.228 | 53.525 | 35.018 | 1.00 | 30.38 |
| 2201 | CE1 | HIS | 1175 | 74.254 | 52.616 | 34.061 | 1.00 | 31.15 |
| 2202 | NE2 | HIS | 1175 | 74.310 | 53.241 | 32.900 | 1.00 | 31.52 |
| 2203 | C | HIS | 1175 | 75.625 | 57.371 | 36.955 | 1.00 | 24.78 |
| 2204 | O | HIS | 1175 | 75.027 | 57.656 | 37.990 | 1.00 | 27.48 |
| 2205 | N | ALA | 1176 | 76.473 | 58.198 | 36.358 | 1.00 | 23.70 |
| 2206 | CA | ALA | 1176 | 76.782 | 59.506 | 36.913 | 1.00 | 21.48 |
| 2207 | CB | ALA | 1176 | 77.996 | 60.107 | 36.210 | 1.00 | 20.07 |
| 2208 | C | ALA | 1176 | 75.630 | 60.492 | 36.910 | 1.00 | 21.16 |
| 2209 | O | ALA | 1176 | 75.016 | 60.740 | 35.881 | 1.00 | 21.05 |
| 2210 | N | VAL | 1177 | 75.339 | 61.036 | 38.083 | 1.00 | 20.47 |
| 2211 | CA | VAL | 1177 | 74.286 | 62.025 | 38.254 | 1.00 | 20.12 |
| 2212 | CB | VAL | 1177 | 73.375 | 61.663 | 39.454 | 1.00 | 22.63 |
| 2213 | CG1 | VAL | 1177 | 72.432 | 62.818 | 39.789 | 1.00 | 21.63 |
| 2214 | CG2 | VAL | 1177 | 72.574 | 60.399 | 39.141 | 1.00 | 20.84 |
| 2215 | C | VAL | 1177 | 74.933 | 63.402 | 38.469 | 1.00 | 20.43 |
| 2216 | O | VAL | 1177 | 74.374 | 64.436 | 38.086 | 1.00 | 19.45 |
| 2217 | N | GLY | 1178 | 76.136 | 63.409 | 39.035 | 1.00 | 20.41 |
| 2218 | CA | GLY | 1178 | 76.836 | 64.661 | 39.267 | 1.00 | 18.90 |
| 2219 | C | GLY | 1178 | 78.153 | 64.429 | 39.972 | 1.00 | 18.98 |
| 2220 | O | GLY | 1178 | 78.499 | 63.283 | 40.271 | 1.00 | 19.19 |
| 2221 | N | LEU | 1179 | 78.887 | 65.508 | 40.230 | 1.00 | 18.30 |
| 2222 | CA | LEU | 1179 | 80.173 | 65.435 | 40.919 | 1.00 | 18.00 |
| 2223 | CB | LEU | 1179 | 81.298 | 66.027 | 40.054 | 1.00 | 12.80 |
| 2224 | CG | LEU | 1179 | 81.484 | 65.535 | 38.614 | 1.00 | 12.14 |
| 2225 | CD1 | LEU | 1179 | 82.733 | 66.154 | 38.040 | 1.00 | 9.04 |
| 2226 | CD2 | LEU | 1179 | 81.568 | 64.034 | 38.557 | 1.00 | 11.17 |
| 2227 | C | LEU | 1179 | 80.058 | 66.223 | 42.221 | 1.00 | 18.90 |
| 2228 | O | LEU | 1179 | 79.564 | 67.344 | 42.223 | 1.00 | 23.62 |
| 2229 | N | PHE | 1180 | 80.476 | 65.632 | 43.332 | 1.00 | 19.19 |

FIG. 3A-49

| Atom | Atom Type | Resid | # | X | Y | Z | OCC | B |
|---|---|---|---|---|---|---|---|---|
| 2230 | CA | PHE | 1180 | 80.418 | 66.301 | 44.625 | 1.00 | 19.90 |
| 2231 | CB | PHE | 1180 | 80.994 | 65.370 | 45.692 | 1.00 | 18.26 |
| 2232 | CG | PHE | 1180 | 81.071 | 65.968 | 47.070 | 1.00 | 18.11 |
| 2233 | CD1 | PHE | 1180 | 82.281 | 66.015 | 47.752 | 1.00 | 18.51 |
| 2234 | CD2 | PHE | 1180 | 79.936 | 66.426 | 47.714 | 1.00 | 18.19 |
| 2235 | CE1 | PHE | 1180 | 82.357 | 66.504 | 49.054 | 1.00 | 15.60 |
| 2236 | CE2 | PHE | 1180 | 80.013 | 66.916 | 49.020 | 1.00 | 18.73 |
| 2237 | CZ | PHE | 1180 | 81.226 | 66.951 | 49.683 | 1.00 | 14.64 |
| 2238 | C | PHE | 1180 | 81.225 | 67.594 | 44.552 | 1.00 | 21.74 |
| 2239 | O | PHE | 1180 | 82.397 | 67.565 | 44.195 | 1.00 | 23.00 |
| 2240 | N | ARG | 1181 | 80.583 | 68.727 | 44.826 | 1.00 | 24.80 |
| 2241 | CA | ARG | 1181 | 81.270 | 70.020 | 44.800 | 1.00 | 26.34 |
| 2242 | CB | ARG | 1181 | 80.427 | 71.116 | 44.144 | 1.00 | 26.66 |
| 2243 | CG | ARG | 1181 | 81.215 | 72.411 | 43.959 | 1.00 | 29.11 |
| 2244 | CD | ARG | 1181 | 80.365 | 73.532 | 43.425 | 1.00 | 33.23 |
| 2245 | NE | ARG | 1181 | 79.368 | 73.951 | 44.403 | 1.00 | 39.30 |
| 2246 | CZ | ARG | 1181 | 78.054 | 73.952 | 44.189 | 1.00 | 41.81 |
| 2247 | NH1 | ARG | 1181 | 77.559 | 73.555 | 43.020 | 1.00 | 42.79 |
| 2248 | NH2 | ARG | 1181 | 77.231 | 74.345 | 45.158 | 1.00 | 44.71 |
| 2249 | C | ARG | 1181 | 81.636 | 70.475 | 46.200 | 1.00 | 26.61 |
| 2250 | O | ARG | 1181 | 82.801 | 70.745 | 46.485 | 1.00 | 29.02 |
| 2251 | N | ALA | 1182 | 80.641 | 70.572 | 47.069 | 1.00 | 26.67 |
| 2252 | CA | ALA | 1182 | 80.892 | 71.008 | 48.426 | 1.00 | 27.49 |
| 2253 | CB | ALA | 1182 | 80.867 | 72.513 | 48.493 | 1.00 | 29.65 |
| 2254 | C | ALA | 1182 | 79.855 | 70.427 | 49.358 | 1.00 | 28.32 |
| 2255 | O | ALA | 1182 | 78.764 | 70.072 | 48.926 | 1.00 | 28.73 |
| 2256 | N | ALA | 1183 | 80.200 | 70.327 | 50.634 | 1.00 | 28.98 |
| 2257 | CA | ALA | 1183 | 79.281 | 69.787 | 51.622 | 1.00 | 32.58 |
| 2258 | CB | ALA | 1183 | 80.030 | 68.926 | 52.633 | 1.00 | 33.65 |
| 2259 | C | ALA | 1183 | 78.544 | 70.906 | 52.333 | 1.00 | 34.36 |
| 2260 | O | ALA | 1183 | 79.093 | 71.991 | 52.541 | 1.00 | 34.73 |
| 2261 | N | VAL | 1184 | 77.290 | 70.635 | 52.680 | 1.00 | 36.46 |
| 2262 | CA | VAL | 1184 | 76.437 | 71.577 | 53.388 | 1.00 | 37.51 |
| 2263 | CB | VAL | 1184 | 75.019 | 71.572 | 52.816 | 1.00 | 36.89 |
| 2264 | CG1 | VAL | 1184 | 74.119 | 72.441 | 53.663 | 1.00 | 36.81 |
| 2265 | CG2 | VAL | 1184 | 75.033 | 72.041 | 51.373 | 1.00 | 36.21 |
| 2266 | C | VAL | 1184 | 76.375 | 71.110 | 54.830 | 1.00 | 39.28 |
| 2267 | O | VAL | 1184 | 75.844 | 70.041 | 55.116 | 1.00 | 39.09 |
| 2268 | N | CYS | 1185 | 76.875 | 71.927 | 55.744 | 1.00 | 44.38 |
| 2269 | CA | CYS | 1185 | 76.895 | 71.546 | 57.148 | 1.00 | 48.30 |
| 2270 | CB | CYS | 1185 | 78.232 | 70.868 | 57.450 | 1.00 | 51.20 |
| 2271 | SG | CYS | 1185 | 79.678 | 71.835 | 56.911 | 1.00 | 61.55 |
| 2272 | C | CYS | 1185 | 76.654 | 72.660 | 58.166 | 1.00 | 47.66 |
| 2273 | O | CYS | 1185 | 76.474 | 73.830 | 57.821 | 1.00 | 48.84 |
| 2274 | N | ALA | 1186 | 76.674 | 72.263 | 59.432 | 1.00 | 46.42 |
| 2275 | CA | ALA | 1186 | 76.482 | 73.153 | 60.563 | 1.00 | 45.62 |
| 2276 | CB | ALA | 1186 | 75.005 | 73.436 | 60.755 | 1.00 | 46.93 |
| 2277 | C | ALA | 1186 | 77.026 | 72.370 | 61.748 | 1.00 | 45.29 |
| 2278 | O | ALA | 1186 | 76.737 | 71.184 | 61.888 | 1.00 | 44.78 |

FIG. 3A-50

| Atom | Atom Type | Resid | # | X | Y | Z | OCC | B |
|---|---|---|---|---|---|---|---|---|
| 2279 | N | ARG | 1187 | 77.857 | 73.014 | 62.563 | 1.00 | 44.52 |
| 2280 | CA | ARG | 1187 | 78.468 | 72.364 | 63.726 | 1.00 | 43.45 |
| 2281 | CB | ARG | 1187 | 77.415 | 71.680 | 64.617 | 1.00 | 45.37 |
| 2282 | CG | ARG | 1187 | 76.904 | 72.544 | 65.761 | 1.00 | 46.88 |
| 2283 | CD | ARG | 1187 | 76.224 | 73.789 | 65.243 | 1.00 | 49.61 |
| 2284 | NE | ARG | 1187 | 76.134 | 74.839 | 66.250 | 1.00 | 49.41 |
| 2285 | CZ | ARG | 1187 | 75.294 | 75.867 | 66.178 | 1.00 | 50.80 |
| 2286 | NH1 | ARG | 1187 | 74.461 | 75.988 | 65.148 | 1.00 | 50.93 |
| 2287 | NH2 | ARG | 1187 | 75.280 | 76.772 | 67.146 | 1.00 | 50.83 |
| 2288 | C | ARG | 1187 | 79.510 | 71.347 | 63.290 | 1.00 | 41.49 |
| 2289 | O | ARG | 1187 | 79.995 | 70.557 | 64.098 | 1.00 | 43.20 |
| 2290 | N | GLY | 1188 | 79.879 | 71.389 | 62.015 | 1.00 | 38.92 |
| 2291 | CA | GLY | 1188 | 80.864 | 70.451 | 61.515 | 1.00 | 36.42 |
| 2292 | C | GLY | 1188 | 80.282 | 69.107 | 61.126 | 1.00 | 34.79 |
| 2293 | O | GLY | 1188 | 81.029 | 68.157 | 60.914 | 1.00 | 37.40 |
| 2294 | N | VAL | 1189 | 78.960 | 69.014 | 61.037 | 1.00 | 32.66 |
| 2295 | CA | VAL | 1189 | 78.303 | 67.771 | 60.653 | 1.00 | 30.43 |
| 2296 | CB | VAL | 1189 | 77.228 | 67.334 | 61.689 | 1.00 | 31.40 |
| 2297 | CG1 | VAL | 1189 | 76.468 | 66.111 | 61.199 | 1.00 | 31.51 |
| 2298 | CG2 | VAL | 1189 | 77.872 | 67.017 | 63.018 | 1.00 | 33.33 |
| 2299 | C | VAL | 1189 | 77.628 | 68.016 | 59.311 | 1.00 | 31.53 |
| 2300 | O | VAL | 1189 | 76.740 | 68.867 | 59.203 | 1.00 | 31.66 |
| 2301 | N | ALA | 1190 | 78.101 | 67.315 | 58.285 | 1.00 | 30.61 |
| 2302 | CA | ALA | 1190 | 77.567 | 67.420 | 56.932 | 1.00 | 29.84 |
| 2303 | CB | ALA | 1190 | 78.511 | 66.754 | 55.956 | 1.00 | 29.82 |
| 2304 | C | ALA | 1190 | 76.198 | 66.760 | 56.856 | 1.00 | 31.17 |
| 2305 | O | ALA | 1190 | 76.073 | 65.552 | 57.075 | 1.00 | 33.60 |
| 2306 | N | ALA | 1191 | 75.174 | 67.545 | 56.542 | 1.00 | 29.63 |
| 2307 | CA | ALA | 1191 | 73.821 | 67.021 | 56.443 | 1.00 | 27.51 |
| 2308 | CB | ALA | 1191 | 72.880 | 67.836 | 57.313 | 1.00 | 27.97 |
| 2309 | C | ALA | 1191 | 73.334 | 66.997 | 55.000 | 1.00 | 28.18 |
| 2310 | O | ALA | 1191 | 72.409 | 66.253 | 54.668 | 1.00 | 31.13 |
| 2311 | N | ALA | 1192 | 73.962 | 67.793 | 54.138 | 1.00 | 26.71 |
| 2312 | CA | ALA | 1192 | 73.594 | 67.853 | 52.721 | 1.00 | 24.73 |
| 2313 | CB | ALA | 1192 | 72.674 | 69.024 | 52.449 | 1.00 | 25.63 |
| 2314 | C | ALA | 1192 | 74.858 | 68.002 | 51.909 | 1.00 | 24.75 |
| 2315 | O | ALA | 1192 | 75.935 | 68.200 | 52.473 | 1.00 | 23.68 |
| 2316 | N | VAL | 1193 | 74.738 | 67.893 | 50.591 | 1.00 | 25.76 |
| 2317 | CA | VAL | 1193 | 75.897 | 68.017 | 49.712 | 1.00 | 26.76 |
| 2318 | CB | VAL | 1193 | 76.503 | 66.627 | 49.325 | 1.00 | 27.03 |
| 2319 | CG1 | VAL | 1193 | 76.940 | 65.861 | 50.566 | 1.00 | 26.31 |
| 2320 | CG2 | VAL | 1193 | 75.512 | 65.807 | 48.515 | 1.00 | 27.41 |
| 2321 | C | VAL | 1193 | 75.569 | 68.756 | 48.425 | 1.00 | 27.01 |
| 2322 | O | VAL | 1193 | 74.608 | 68.413 | 47.735 | 1.00 | 27.50 |
| 2323 | N | ASP | 1194 | 76.333 | 69.807 | 48.146 | 1.00 | 26.41 |
| 2324 | CA | ASP | 1194 | 76.180 | 70.587 | 46.926 | 1.00 | 27.71 |
| 2325 | CB | ASP | 1194 | 76.750 | 71.995 | 47.109 | 1.00 | 30.91 |
| 2326 | CG | ASP | 1194 | 75.836 | 72.906 | 47.907 | 1.00 | 34.47 |
| 2327 | OD1 | ASP | 1194 | 76.335 | 73.953 | 48.389 | 1.00 | 36.98 |

FIG. 3A-51

| Atom | Atom Type | Resid | # | X | Y | Z | OCC | B |
|---|---|---|---|---|---|---|---|---|
| 2328 | OD2 | ASP | 1194 | 74.626 | 72.590 | 48.041 | 1.00 | 35.44 |
| 2329 | C | ASP | 1194 | 76.958 | 69.895 | 45.817 | 1.00 | 26.97 |
| 2330 | O | ASP | 1194 | 78.163 | 69.650 | 45.964 | 1.00 | 26.74 |
| 2331 | N | PHE | 1195 | 76.296 | 69.608 | 44.701 | 1.00 | 24.78 |
| 2332 | CA | PHE | 1195 | 76.976 | 68.948 | 43.599 | 1.00 | 23.72 |
| 2333 | CB | PHE | 1195 | 76.625 | 67.458 | 43.546 | 1.00 | 23.09 |
| 2334 | CG | PHE | 1195 | 75.185 | 67.171 | 43.244 | 1.00 | 21.65 |
| 2335 | CD1 | PHE | 1195 | 74.748 | 67.042 | 41.933 | 1.00 | 21.20 |
| 2336 | CD2 | PHE | 1195 | 74.268 | 66.991 | 44.276 | 1.00 | 22.38 |
| 2337 | CE1 | PHE | 1195 | 73.417 | 66.736 | 41.650 | 1.00 | 20.66 |
| 2338 | CE2 | PHE | 1195 | 72.935 | 66.684 | 44.005 | 1.00 | 21.40 |
| 2339 | CZ | PHE | 1195 | 72.510 | 66.556 | 42.689 | 1.00 | 21.45 |
| 2340 | C | PHE | 1195 | 76.755 | 69.592 | 42.244 | 1.00 | 24.27 |
| 2341 | O | PHE | 1195 | 75.898 | 70.452 | 42.076 | 1.00 | 26.48 |
| 2342 | N | ILE | 1196 | 77.572 | 69.181 | 41.285 | 1.00 | 23.52 |
| 2343 | CA | ILE | 1196 | 77.521 | 69.679 | 39.925 | 1.00 | 22.71 |
| 2344 | CB | ILE | 1196 | 78.946 | 69.790 | 39.354 | 1.00 | 22.75 |
| 2345 | CG2 | ILE | 1196 | 78.903 | 70.308 | 37.923 | 1.00 | 24.48 |
| 2346 | CG1 | ILE | 1196 | 79.804 | 70.682 | 40.255 | 1.00 | 21.53 |
| 2347 | CD1 | ILE | 1196 | 81.283 | 70.593 | 39.987 | 1.00 | 20.43 |
| 2348 | C | ILE | 1196 | 76.753 | 68.658 | 39.090 | 1.00 | 24.50 |
| 2349 | O | ILE | 1196 | 77.240 | 67.552 | 38.856 | 1.00 | 25.41 |
| 2350 | N | PRO | 1197 | 75.525 | 68.993 | 38.666 | 1.00 | 24.80 |
| 2351 | CD | PRO | 1197 | 74.778 | 70.230 | 38.940 | 1.00 | 24.02 |
| 2352 | CA | PRO | 1197 | 74.718 | 68.076 | 37.858 | 1.00 | 24.02 |
| 2353 | CB | PRO | 1197 | 73.466 | 68.900 | 37.571 | 1.00 | 21.87 |
| 2354 | CG | PRO | 1197 | 73.360 | 69.780 | 38.748 | 1.00 | 21.74 |
| 2355 | C | PRO | 1197 | 75.444 | 67.751 | 36.557 | 1.00 | 24.76 |
| 2356 | O | PRO | 1197 | 76.143 | 68.606 | 36.011 | 1.00 | 25.57 |
| 2357 | N | VAL | 1198 | 75.267 | 66.537 | 36.044 | 1.00 | 26.89 |
| 2358 | CA | VAL | 1198 | 75.923 | 66.159 | 34.797 | 1.00 | 28.24 |
| 2359 | CB | VAL | 1198 | 75.541 | 64.746 | 34.338 | 1.00 | 27.91 |
| 2360 | CG1 | VAL | 1198 | 76.318 | 64.392 | 33.091 | 1.00 | 32.68 |
| 2361 | CG2 | VAL | 1198 | 75.869 | 63.747 | 35.401 | 1.00 | 28.52 |
| 2362 | C | VAL | 1198 | 75.583 | 67.148 | 33.684 | 1.00 | 29.68 |
| 2363 | O | VAL | 1198 | 76.397 | 67.390 | 32.794 | 1.00 | 31.51 |
| 2364 | N | ALA | 1199 | 74.394 | 67.741 | 33.754 | 1.00 | 30.96 |
| 2365 | CA | ALA | 1199 | 73.954 | 68.718 | 32.759 | 1.00 | 28.72 |
| 2366 | CB | ALA | 1199 | 72.610 | 69.294 | 33.157 | 1.00 | 30.86 |
| 2367 | C | ALA | 1199 | 74.970 | 69.838 | 32.603 | 1.00 | 27.35 |
| 2368 | O | ALA | 1199 | 75.193 | 70.346 | 31.503 | 1.00 | 27.43 |
| 2369 | N | ASN | 1200 | 75.593 | 70.223 | 33.707 | 1.00 | 25.52 |
| 2370 | CA | ASN | 1200 | 76.586 | 71.280 | 33.671 | 1.00 | 25.79 |
| 2371 | CB | ASN | 1200 | 76.951 | 71.723 | 35.084 | 1.00 | 25.77 |
| 2372 | CG | ASN | 1200 | 75.810 | 72.442 | 35.789 | 1.00 | 27.58 |
| 2373 | OD1 | ASN | 1200 | 76.015 | 73.075 | 36.828 | 1.00 | 29.86 |
| 2374 | ND2 | ASN | 1200 | 74.602 | 72.337 | 35.246 | 1.00 | 25.16 |
| 2375 | C | ASN | 1200 | 77.828 | 70.842 | 32.907 | 1.00 | 26.50 |
| 2376 | O | ASN | 1200 | 78.544 | 71.681 | 32.358 | 1.00 | 25.46 |

FIG. 3A-52

| Atom | Atom Type | Resid | # | X | Y | Z | OCC | B |
|---|---|---|---|---|---|---|---|---|
| 2377 | N | LEU | 1201 | 78.063 | 69.531 | 32.844 | 1.00 | 27.79 |
| 2378 | CA | LEU | 1201 | 79.213 | 68.977 | 32.125 | 1.00 | 27.44 |
| 2379 | CB | LEU | 1201 | 79.400 | 67.488 | 32.437 | 1.00 | 27.76 |
| 2380 | CG | LEU | 1201 | 79.560 | 67.059 | 33.897 | 1.00 | 27.52 |
| 2381 | CD1 | LEU | 1201 | 79.793 | 65.564 | 33.955 | 1.00 | 28.46 |
| 2382 | CD2 | LEU | 1201 | 80.703 | 67.790 | 34.548 | 1.00 | 24.26 |
| 2383 | C | LEU | 1201 | 79.021 | 69.163 | 30.627 | 1.00 | 26.96 |
| 2384 | O | LEU | 1201 | 79.891 | 69.694 | 29.946 | 1.00 | 26.74 |
| 2385 | N | GLU | 1202 | 77.864 | 68.752 | 30.125 | 1.00 | 27.76 |
| 2386 | CA | GLU | 1202 | 77.555 | 68.886 | 28.703 | 1.00 | 30.15 |
| 2387 | CB | GLU | 1202 | 76.207 | 68.237 | 28.404 | 1.00 | 35.17 |
| 2388 | CG | GLU | 1202 | 75.915 | 68.080 | 26.912 | 1.00 | 42.07 |
| 2389 | CD | GLU | 1202 | 76.742 | 66.985 | 26.247 | 1.00 | 45.05 |
| 2390 | OE1 | GLU | 1202 | 76.867 | 65.882 | 26.837 | 1.00 | 45.05 |
| 2391 | OE2 | GLU | 1202 | 77.253 | 67.232 | 25.129 | 1.00 | 48.05 |
| 2392 | C | GLU | 1202 | 77.530 | 70.362 | 28.311 | 1.00 | 27.55 |
| 2393 | O | GLU | 1202 | 77.988 | 70.746 | 27.239 | 1.00 | 26.78 |
| 2394 | N | THR | 1203 | 76.989 | 71.182 | 29.200 | 1.00 | 27.54 |
| 2395 | CA | THR | 1203 | 76.916 | 72.618 | 28.997 | 1.00 | 28.52 |
| 2396 | CB | THR | 1203 | 76.183 | 73.278 | 30.168 | 1.00 | 29.70 |
| 2397 | OG1 | THR | 1203 | 74.814 | 72.848 | 30.179 | 1.00 | 31.63 |
| 2398 | CG2 | THR | 1203 | 76.248 | 74.787 | 30.066 | 1.00 | 30.94 |
| 2399 | C | THR | 1203 | 78.336 | 73.175 | 28.923 | 1.00 | 30.35 |
| 2400 | O | THR | 1203 | 78.630 | 74.038 | 28.099 | 1.00 | 31.87 |
| 2401 | N | THR | 1204 | 79.204 | 72.693 | 29.810 | 1.00 | 30.89 |
| 2402 | CA | THR | 1204 | 80.597 | 73.126 | 29.839 | 1.00 | 30.06 |
| 2403 | CB | THR | 1204 | 81.325 | 72.545 | 31.070 | 1.00 | 27.84 |
| 2404 | OG1 | THR | 1204 | 80.789 | 73.148 | 32.254 | 1.00 | 28.92 |
| 2405 | CG2 | THR | 1204 | 82.823 | 72.804 | 31.010 | 1.00 | 26.94 |
| 2406 | C | THR | 1204 | 81.329 | 72.732 | 28.551 | 1.00 | 31.06 |
| 2407 | O | THR | 1204 | 82.238 | 73.435 | 28.113 | 1.00 | 31.97 |
| 2408 | N | MET | 1205 | 80.918 | 71.622 | 27.940 | 1.00 | 30.02 |
| 2409 | CA | MET | 1205 | 81.545 | 71.155 | 26.710 | 1.00 | 29.36 |
| 2410 | CB | MET | 1205 | 81.286 | 69.670 | 26.503 | 1.00 | 26.89 |
| 2411 | CG | MET | 1205 | 81.846 | 68.816 | 27.605 | 1.00 | 26.79 |
| 2412 | SD | MET | 1205 | 81.869 | 67.096 | 27.164 | 1.00 | 25.34 |
| 2413 | CE | MET | 1205 | 80.165 | 66.684 | 27.336 | 1.00 | 26.80 |
| 2414 | C | MET | 1205 | 81.101 | 71.927 | 25.480 | 1.00 | 30.12 |
| 2415 | O | MET | 1205 | 81.795 | 71.910 | 24.463 | 1.00 | 31.11 |
| 2416 | N | ARG | 1206 | 79.944 | 72.582 | 25.560 | 1.00 | 32.04 |
| 2417 | CA | ARG | 1206 | 79.425 | 73.372 | 24.443 | 1.00 | 32.33 |
| 2418 | CB | ARG | 1206 | 77.898 | 73.466 | 24.509 | 1.00 | 33.91 |
| 2419 | CG | ARG | 1206 | 77.180 | 72.147 | 24.315 | 1.00 | 36.45 |
| 2420 | CD | ARG | 1206 | 75.689 | 72.368 | 24.083 | 1.00 | 39.82 |
| 2421 | NE | ARG | 1206 | 74.994 | 72.858 | 25.274 | 1.00 | 44.02 |
| 2422 | CZ | ARG | 1206 | 74.337 | 72.082 | 26.140 | 1.00 | 44.21 |
| 2423 | NH1 | ARG | 1206 | 74.272 | 70.767 | 25.962 | 1.00 | 41.77 |
| 2424 | NH2 | ARG | 1206 | 73.760 | 72.623 | 27.207 | 1.00 | 44.77 |
| 2425 | C | ARG | 1206 | 80.030 | 74.780 | 24.404 | 1.00 | 31.71 |

FIG. 3A-53

| Atom | Atom Type | Resid | # | X | Y | Z | OCC | B |
|---|---|---|---|---|---|---|---|---|
| 2426 | O | ARG | 1206 | 80.163 | 75.405 | 25.487 | 1.00 | 33.75 | sNS4A COORDINATES (Complex B)

| Atom | Atom Type | Resid | # | X | Y | Z | OCC | B |
|---|---|---|---|---|---|---|---|---|
| 2535 | CB | LYS | 1677 | 101.069 | 76.195 | 38.823 | 1.00 | 42.61 |
| 2536 | CG | LYS | 1677 | 100.696 | 76.412 | 40.284 | 1.00 | 45.42 |
| 2537 | CD | LYS | 1677 | 99.373 | 77.170 | 40.435 | 1.00 | 48.57 |
| 2538 | CE | LYS | 1677 | 99.221 | 77.735 | 41.859 | 1.00 | 50.16 |
| 2539 | NZ | LYS | 1677 | 97.898 | 78.400 | 42.112 | 1.00 | 51.22 |
| 2540 | C | LYS | 1677 | 102.635 | 74.294 | 38.331 | 1.00 | 39.53 |
| 2541 | O | LYS | 1677 | 102.747 | 73.868 | 37.171 | 1.00 | 39.44 |
| 2542 | N | LYS | 1677 | 103.162 | 76.602 | 37.521 | 1.00 | 40.63 |
| 2543 | CA | LYS | 1677 | 102.536 | 75.793 | 38.615 | 1.00 | 40.89 |
| 2544 | N | GLY | 1678 | 102.595 | 73.497 | 39.393 | 1.00 | 37.81 |
| 2545 | CA | GLY | 1678 | 102.708 | 72.057 | 39.240 | 1.00 | 34.76 |
| 2546 | C | GLY | 1678 | 101.509 | 71.417 | 38.576 | 1.00 | 31.90 |
| 2547 | O | GLY | 1678 | 100.461 | 72.045 | 38.430 | 1.00 | 31.54 |
| 2548 | N | SER | 1679 | 101.684 | 70.181 | 38.126 | 1.00 | 28.52 |
| 2549 | CA | SER | 1679 | 100.606 | 69.443 | 37.497 | 1.00 | 25.57 |
| 2550 | CB | SER | 1679 | 101.167 | 68.417 | 36.506 | 1.00 | 26.14 |
| 2551 | OG | SER | 1679 | 101.609 | 69.016 | 35.303 | 1.00 | 24.59 |
| 2552 | C | SER | 1679 | 99.807 | 68.703 | 38.562 | 1.00 | 24.40 |
| 2553 | O | SER | 1679 | 100.280 | 68.506 | 39.688 | 1.00 | 24.38 |
| 2554 | N | VAL | 1680 | 98.574 | 68.346 | 38.219 | 1.00 | 23.52 |
| 2555 | CA | VAL | 1680 | 97.724 | 67.576 | 39.106 | 1.00 | 21.39 |
| 2556 | CB | VAL | 1680 | 96.252 | 67.694 | 38.697 | 1.00 | 21.22 |
| 2557 | CG1 | VAL | 1680 | 95.392 | 66.728 | 39.493 | 1.00 | 19.38 |
| 2558 | CG2 | VAL | 1680 | 95.784 | 69.112 | 38.932 | 1.00 | 21.01 |
| 2559 | C | VAL | 1680 | 98.230 | 66.158 | 38.894 | 1.00 | 20.14 |
| 2560 | O | VAL | 1680 | 98.478 | 65.754 | 37.754 | 1.00 | 18.28 |
| 2561 | N | VAL | 1681 | 98.463 | 65.442 | 39.990 | 1.00 | 20.40 |
| 2562 | CA | VAL | 1681 | 98.990 | 64.085 | 39.922 | 1.00 | 20.62 |
| 2563 | CB | VAL | 1681 | 100.343 | 63.971 | 40.678 | 1.00 | 18.90 |
| 2564 | CG1 | VAL | 1681 | 100.968 | 62.616 | 40.454 | 1.00 | 19.40 |
| 2565 | CG2 | VAL | 1681 | 101.283 | 65.039 | 40.231 | 1.00 | 20.79 |
| 2566 | C | VAL | 1681 | 98.050 | 63.055 | 40.522 | 1.00 | 21.25 |
| 2567 | O | VAL | 1681 | 97.459 | 63.277 | 41.584 | 1.00 | 19.23 |
| 2568 | N | ILE | 1682 | 97.956 | 61.910 | 39.850 | 1.00 | 22.25 |
| 2569 | CA | ILE | 1682 | 97.134 | 60.795 | 40.304 | 1.00 | 22.27 |
| 2570 | CB | ILE | 1682 | 96.791 | 59.853 | 39.125 | 1.00 | 18.88 |
| 2571 | CG2 | ILE | 1682 | 96.052 | 58.633 | 39.627 | 1.00 | 19.14 |
| 2572 | CG1 | ILE | 1682 | 95.940 | 60.597 | 38.094 | 1.00 | 17.33 |
| 2573 | CD1 | ILE | 1682 | 95.611 | 59.800 | 36.862 | 1.00 | 14.03 |
| 2574 | C | ILE | 1682 | 97.926 | 60.028 | 41.376 | 1.00 | 23.98 |
| 2575 | O | ILE | 1682 | 98.998 | 59.474 | 41.090 | 1.00 | 24.49 |
| 2576 | N | VAL | 1683 | 97.425 | 60.045 | 42.611 | 1.00 | 24.04 |

FIG. 3A-54

| Atom | Atom Type | Resid | # | X | Y | Z | OCC | B |
|---|---|---|---|---|---|---|---|---|
| 2577 | CA | VAL | 1683 | 98.074 | 59.345 | 43.724 | 1.00 | 22.87 |
| 2578 | CB | VAL | 1683 | 98.294 | 60.273 | 44.960 | 1.00 | 20.49 |
| 2579 | CG1 | VAL | 1683 | 99.218 | 61.422 | 44.602 | 1.00 | 21.14 |
| 2580 | CG2 | VAL | 1683 | 96.986 | 60.787 | 45.493 | 1.00 | 15.48 |
| 2581 | C | VAL | 1683 | 97.319 | 58.086 | 44.177 | 1.00 | 22.99 |
| 2582 | O | VAL | 1683 | 97.667 | 57.470 | 45.190 | 1.00 | 25.32 |
| 2583 | N | GLY | 1684 | 96.294 | 57.704 | 43.423 | 1.00 | 22.53 |
| 2584 | CA | GLY | 1684 | 95.515 | 56.527 | 43.757 | 1.00 | 21.02 |
| 2585 | C | GLY | 1684 | 94.291 | 56.452 | 42.870 | 1.00 | 21.67 |
| 2586 | O | GLY | 1684 | 94.144 | 57.267 | 41.956 | 1.00 | 21.86 |
| 2587 | N | ARG | 1685 | 93.399 | 55.507 | 43.154 | 1.00 | 22.35 |
| 2588 | CA | ARG | 1685 | 92.177 | 55.327 | 42.369 | 1.00 | 19.90 |
| 2589 | CB | ARG | 1685 | 92.449 | 54.463 | 41.150 | 1.00 | 20.04 |
| 2590 | CG | ARG | 1685 | 93.003 | 53.105 | 41.516 | 1.00 | 22.48 |
| 2591 | CD | ARG | 1685 | 93.157 | 52.240 | 40.296 | 1.00 | 26.67 |
| 2592 | NE | ARG | 1685 | 94.237 | 51.271 | 40.446 | 1.00 | 28.97 |
| 2593 | CZ | ARG | 1685 | 95.485 | 51.487 | 40.048 | 1.00 | 27.79 |
| 2594 | NH1 | ARG | 1685 | 95.815 | 52.632 | 39.474 | 1.00 | 27.86 |
| 2595 | NH2 | ARG | 1685 | 96.404 | 50.557 | 40.224 | 1.00 | 29.00 |
| 2596 | C | ARG | 1685 | 91.113 | 54.636 | 43.185 | 1.00 | 20.01 |
| 2597 | O | ARG | 1685 | 91.404 | 54.035 | 44.218 | 1.00 | 22.88 |
| 2598 | N | ILE | 1686 | 89.882 | 54.703 | 42.697 | 1.00 | 18.51 |
| 2599 | CA | ILE | 1686 | 88.745 | 54.066 | 43.346 | 1.00 | 17.38 |
| 2600 | CB | ILE | 1686 | 87.823 | 55.120 | 43.985 | 1.00 | 15.63 |
| 2601 | CG2 | ILE | 1686 | 86.464 | 54.533 | 44.292 | 1.00 | 14.38 |
| 2602 | CG1 | ILE | 1686 | 88.496 | 55.665 | 45.251 | 1.00 | 14.48 |
| 2603 | CD1 | ILE | 1686 | 87.740 | 56.758 | 45.935 | 1.00 | 14.17 |
| 2604 | C | ILE | 1686 | 88.043 | 53.247 | 42.268 | 1.00 | 17.71 |
| 2605 | O | ILE | 1686 | 87.699 | 53.769 | 41.205 | 1.00 | 17.73 |
| 2606 | N | VAL | 1687 | 87.945 | 51.940 | 42.484 | 1.00 | 16.52 |
| 2607 | CA | VAL | 1687 | 87.325 | 51.073 | 41.493 | 1.00 | 14.59 |
| 2608 | CB | VAL | 1687 | 88.152 | 49.810 | 41.237 | 1.00 | 13.39 |
| 2609 | CG1 | VAL | 1687 | 87.509 | 48.980 | 40.145 | 1.00 | 11.21 |
| 2610 | CG2 | VAL | 1687 | 89.564 | 50.184 | 40.842 | 1.00 | 11.10 |
| 2611 | C | VAL | 1687 | 85.922 | 50.681 | 41.874 | 1.00 | 15.40 |
| 2612 | O | VAL | 1687 | 85.695 | 50.067 | 42.916 | 1.00 | 17.30 |
| 2613 | N | LEU | 1688 | 84.990 | 51.081 | 41.016 | 1.00 | 16.16 |
| 2614 | CA | LEU | 1688 | 83.566 | 50.827 | 41.171 | 1.00 | 15.94 |
| 2615 | CB | LEU | 1688 | 82.792 | 52.003 | 40.578 | 1.00 | 14.08 |
| 2616 | CG | LEU | 1688 | 82.936 | 53.300 | 41.365 | 1.00 | 15.70 |
| 2617 | CD1 | LEU | 1688 | 82.611 | 54.511 | 40.519 | 1.00 | 15.92 |
| 2618 | CD2 | LEU | 1688 | 82.026 | 53.212 | 42.559 | 1.00 | 18.17 |
| 2619 | C | LEU | 1688 | 83.129 | 49.532 | 40.481 | 1.00 | 17.97 |
| 2620 | O | LEU | 1688 | 82.209 | 48.856 | 40.939 | 1.00 | 20.09 |
| 2621 | N | SER | 1689 | 83.826 | 49.174 | 39.406 | 1.00 | 20.02 |
| 2622 | CA | SER | 1689 | 83.518 | 47.982 | 38.611 | 1.00 | 21.75 |
| 2623 | CB | SER | 1689 | 84.253 | 48.060 | 37.266 | 1.00 | 23.96 |
| 2624 | OG | SER | 1689 | 85.605 | 48.467 | 37.436 | 1.00 | 27.29 |
| 2625 | C | SER | 1689 | 83.749 | 46.603 | 39.243 | 1.00 | 21.43 |

FIG. 3A-55

| Atom | Atom Type | Resid | # | X | Y | Z | OCC | B |
|---|---|---|---|---|---|---|---|---|
| 2626 | O | SER | 1689 | 83.290 | 45.596 | 38.700 | 1.00 | 23.26 |
| 2627 | N | GLY | 1690 | 84.465 | 46.547 | 40.364 | 1.00 | 21.24 |
| 2628 | CA | GLY | 1690 | 84.724 | 45.277 | 41.015 | 1.00 | 19.68 |
| 2629 | C | GLY | 1690 | 83.431 | 44.657 | 41.500 | 1.00 | 21.01 |
| 2630 | O | GLY | 1690 | 82.452 | 45.367 | 41.741 | 1.00 | 20.02 |
| 2631 | N | LYS | 1691 | 83.419 | 43.334 | 41.618 | 1.00 | 22.40 |
| 2632 | CA | LYS | 1691 | 82.245 | 42.596 | 42.075 | 1.00 | 25.78 |
| 2633 | CB | LYS | 1691 | 81.621 | 41.838 | 40.901 | 1.00 | 30.22 |
| 2634 | CG | LYS | 1691 | 81.068 | 42.740 | 39.813 | 1.00 | 38.96 |
| 2635 | CD | LYS | 1691 | 80.651 | 41.947 | 38.575 | 1.00 | 46.14 |
| 2636 | CE | LYS | 1691 | 80.270 | 42.880 | 37.405 | 1.00 | 49.42 |
| 2637 | NZ | LYS | 1691 | 79.814 | 42.127 | 36.186 | 1.00 | 50.87 |
| 2638 | C | LYS | 1691 | 82.705 | 41.610 | 43.142 | 1.00 | 25.02 |
| 2639 | O | LYS | 1691 | 83.885 | 41.254 | 43.176 | 1.00 | 26.26 |
| 2640 | N | PRO | 1692 | 81.796 | 41.167 | 44.031 | 1.00 | 23.86 |
| 2641 | CD | PRO | 1692 | 80.365 | 41.516 | 44.115 | 1.00 | 25.36 |
| 2642 | CA | PRO | 1692 | 82.157 | 40.217 | 45.088 | 1.00 | 23.51 |
| 2643 | CB | PRO | 1692 | 80.801 | 39.691 | 45.542 | 1.00 | 23.49 |
| 2644 | CG | PRO | 1692 | 79.954 | 40.911 | 45.451 | 1.00 | 24.91 |
| 2645 | C | PRO | 1692 | 83.027 | 39.095 | 44.548 | 1.00 | 23.24 |
| 2646 | O | PRO | 1692 | 82.724 | 38.506 | 43.515 | 1.00 | 25.88 |
| 2647 | N | ALA | 1693 | 84.136 | 38.831 | 45.219 | 1.00 | 21.89 |
| 2648 | CA | ALA | 1693 | 85.035 | 37.787 | 44.780 | 1.00 | 21.26 |
| 2649 | CB | ALA | 1693 | 86.173 | 38.383 | 43.989 | 1.00 | 21.74 |
| 2650 | C | ALA | 1693 | 85.568 | 37.089 | 46.000 | 1.00 | 22.42 |
| 2651 | O | ALA | 1693 | 85.708 | 37.705 | 47.055 | 1.00 | 24.98 |
| 2652 | N | ILE | 1694 | 85.810 | 35.791 | 45.879 | 1.00 | 22.49 |
| 2653 | CA | ILE | 1694 | 86.342 | 35.020 | 46.989 | 1.00 | 21.65 |
| 2654 | CB | ILE | 1694 | 86.052 | 33.524 | 46.794 | 1.00 | 20.10 |
| 2655 | CG2 | ILE | 1694 | 86.718 | 32.714 | 47.873 | 1.00 | 22.22 |
| 2656 | CG1 | ILE | 1694 | 84.539 | 33.293 | 46.829 | 1.00 | 20.16 |
| 2657 | CD1 | ILE | 1694 | 84.133 | 31.872 | 46.593 | 1.00 | 19.23 |
| 2658 | C | ILE | 1694 | 87.832 | 35.311 | 46.999 | 1.00 | 22.06 |
| 2659 | O | ILE | 1694 | 88.506 | 35.118 | 45.988 | 1.00 | 25.81 |
| 2660 | N | ILE | 1695 | 88.336 | 35.837 | 48.109 | 1.00 | 21.38 |
| 2661 | CA | ILE | 1695 | 89.748 | 36.181 | 48.194 | 1.00 | 19.73 |
| 2662 | CB | ILE | 1695 | 90.112 | 36.812 | 49.557 | 1.00 | 16.79 |
| 2663 | CG2 | ILE | 1695 | 91.550 | 37.296 | 49.533 | 1.00 | 16.53 |
| 2664 | CG1 | ILE | 1695 | 89.209 | 38.009 | 49.853 | 1.00 | 11.03 |
| 2665 | CD1 | ILE | 1695 | 89.480 | 38.658 | 51.192 | 1.00 | 8.12 |
| 2666 | C | ILE | 1695 | 90.596 | 34.943 | 47.947 | 1.00 | 22.82 |
| 2667 | O | ILE | 1695 | 90.498 | 33.954 | 48.669 | 1.00 | 22.97 |
| 2668 | N | PRO | 1696 | 91.407 | 34.967 | 46.886 | 1.00 | 26.75 |
| 2669 | CD | PRO | 1696 | 91.564 | 36.085 | 45.940 | 1.00 | 28.08 |
| 2670 | CA | PRO | 1696 | 92.279 | 33.851 | 46.520 | 1.00 | 30.50 |
| 2671 | CB | PRO | 1696 | 93.080 | 34.418 | 45.354 | 1.00 | 29.24 |
| 2672 | CG | PRO | 1696 | 92.138 | 35.395 | 44.733 | 1.00 | 28.73 |
| 2673 | C | PRO | 1696 | 93.207 | 33.490 | 47.662 | 1.00 | 36.92 |
| 2674 | O | PRO | 1696 | 93.659 | 34.371 | 48.402 | 1.00 | 37.43 |

FIG. 3A-56

| Atom | Atom Type | Resid | # | X | Y | Z | OCC | B |
|---|---|---|---|---|---|---|---|---|
| 2675 | N | LYS | 1697 | 93.454 | 32.191 | 47.824 | 1.00 | 42.85 |
| 2676 | CA | LYS | 1697 | 94.356 | 31.692 | 48.863 | 1.00 | 46.97 |
| 2677 | CB | LYS | 1697 | 93.938 | 30.284 | 49.314 | 1.00 | 48.62 |
| 2678 | CG | LYS | 1697 | 92.480 | 30.143 | 49.712 | 1.00 | 52.72 |
| 2679 | CD | LYS | 1697 | 92.325 | 29.631 | 51.139 | 1.00 | 54.54 |
| 2680 | CE | LYS | 1697 | 90.885 | 29.167 | 51.394 | 1.00 | 56.49 |
| 2681 | NZ | LYS | 1697 | 90.578 | 27.847 | 50.749 | 1.00 | 59.20 |
| 2682 | C | LYS | 1697 | 95.789 | 31.645 | 48.311 | 1.00 | 48.94 |
| 2683 | O | LYS | 1697 | 96.588 | 32.540 | 48.661 | 1.00 | 50.95 |

ZINC ION COORDINATES

| Atom | Atom Type | Resid | # | X | Y | Z | OCC | B |
|---|---|---|---|---|---|---|---|---|
| 2684 | ZN | ZN | 901 | 71.089 | 51.399 | 51.975 | 1.00 | 29.52 |
| 2685 | ZN | ZN | 902 | 70.157 | 56.302 | 36.264 | 1.00 | 32.22 |

WATER MOLECULE COORDINATES

| Atom | Atom Type | Resid | # | X | Y | Z | OCC | B |
|---|---|---|---|---|---|---|---|---|
| 2686 | OH2 | TIP3 | 1 | 80.188 | 51.569 | 51.895 | 1.00 | 14.91 |
| 2687 | OH2 | TIP3 | 2 | 84.436 | 50.278 | 50.706 | 1.00 | 27.51 |
| 2688 | OH2 | TIP3 | 3 | 80.360 | 48.626 | 54.069 | 1.00 | 26.47 |
| 2689 | OH2 | TIP3 | 4 | 90.933 | 33.696 | 52.289 | 1.00 | 23.43 |
| 2690 | OH2 | TIP3 | 5 | 72.460 | 27.233 | 53.507 | 1.00 | 26.41 |
| 2691 | OH2 | TIP3 | 6 | 87.098 | 37.167 | 56.456 | 1.00 | 35.13 |
| 2692 | OH2 | TIP3 | 7 | 80.196 | 47.990 | 42.389 | 1.00 | 32.46 |
| 2693 | OH2 | TIP3 | 8 | 80.634 | 37.946 | 41.797 | 1.00 | 15.54 |
| 2694 | OH2 | TIP3 | 9 | 91.083 | 45.806 | 52.787 | 1.00 | 17.30 |
| 2695 | OH2 | TIP3 | 10 | 85.712 | 53.247 | 29.331 | 1.00 | 28.74 |
| 2696 | OH2 | TIP3 | 11 | 89.054 | 50.366 | 50.031 | 1.00 | 18.47 |
| 2697 | OH2 | TIP3 | 12 | 79.767 | 46.999 | 50.439 | 1.00 | 24.04 |
| 2698 | OH2 | TIP3 | 13 | 79.409 | 63.138 | 26.964 | 1.00 | 33.09 |
| 2699 | OH2 | TIP3 | 14 | 79.565 | 49.986 | 49.688 | 1.00 | 26.32 |
| 2700 | OH2 | TIP3 | 15 | 88.908 | 25.285 | 68.030 | 1.00 | 19.71 |
| 2701 | OH2 | TIP3 | 16 | 59.074 | 46.155 | 52.416 | 1.00 | 29.76 |
| 2702 | OH2 | TIP3 | 17 | 83.621 | 37.213 | 41.479 | 1.00 | 44.52 |
| 2703 | OH2 | TIP3 | 18 | 59.694 | 46.148 | 55.800 | 1.00 | 34.49 |
| 2704 | OH2 | TIP3 | 19 | 94.223 | 75.564 | 42.730 | 1.00 | 38.61 |
| 2705 | OH2 | TIP3 | 20 | 66.565 | 41.471 | 68.855 | 1.00 | 40.67 |
| 2706 | OH2 | TIP3 | 21 | 94.230 | 39.125 | 44.532 | 1.00 | 37.61 |
| 2707 | OH2 | TIP3 | 22 | 63.801 | 32.294 | 63.606 | 1.00 | 24.75 |
| 2708 | OH2 | TIP3 | 23 | 85.565 | 24.399 | 71.908 | 1.00 | 34.81 |
| 2709 | OH2 | TIP3 | 24 | 78.876 | 64.139 | 29.678 | 1.00 | 39.51 |
| 2710 | OH2 | TIP3 | 25 | 82.850 | 28.849 | 47.546 | 1.00 | 25.28 |
| 2711 | OH2 | TIP3 | 28 | 69.172 | 69.500 | 51.903 | 1.00 | 30.62 |

FIG. 3A-57

| Atom | Atom Type | Resid | # | X | Y | Z | OCC | B |
|---|---|---|---|---|---|---|---|---|
| 2712 | OH2 | TIP3 | 29 | 66.988 | 51.499 | 56.187 | 1.00 | 30.20 |
| 2713 | OH2 | TIP3 | 30 | 91.719 | 42.057 | 60.299 | 1.00 | 31.11 |
| 2714 | OH2 | TIP3 | 31 | 77.543 | 29.196 | 41.350 | 1.00 | 55.87 |
| 2715 | OH2 | TIP3 | 32 | 84.613 | 22.791 | 54.244 | 1.00 | 64.87 |
| 2716 | OH2 | TIP3 | 33 | 71.143 | 49.227 | 43.011 | 1.00 | 36.07 |
| 2717 | OH2 | TIP3 | 34 | 72.527 | 52.824 | 53.213 | 1.00 | 5.56 |
| 2718 | OH2 | TIP3 | 35 | 80.116 | 46.082 | 38.809 | 1.00 | 44.35 |
| 2719 | OH2 | TIP3 | 36 | 65.304 | 58.306 | 50.404 | 1.00 | 50.48 |
| 2720 | OH2 | TIP3 | 38 | 77.283 | 35.181 | 38.894 | 1.00 | 36.34 |
| 2721 | OH2 | TIP3 | 39 | 67.275 | 62.937 | 39.441 | 1.00 | 39.30 |
| 2722 | OH2 | TIP3 | 40 | 95.912 | 77.587 | 39.202 | 1.00 | 37.03 |
| 2723 | OH2 | TIP3 | 41 | 87.028 | 46.815 | 50.178 | 1.00 | 14.09 |
| 2724 | OH2 | TIP3 | 42 | 70.710 | 55.468 | 34.204 | 1.00 | 7.82 |
| 2725 | OH2 | TIP3 | 43 | 87.279 | 67.965 | 49.287 | 1.00 | 23.95 |
| 2726 | OH2 | TIP3 | 44 | 90.719 | 39.572 | 46.110 | 1.00 | 29.46 |
| 2727 | OH2 | TIP3 | 45 | 88.956 | 32.992 | 50.562 | 1.00 | 26.01 |
| 2728 | OH2 | TIP3 | 46 | 99.309 | 29.693 | 67.462 | 1.00 | 19.97 |
| 2729 | OH2 | TIP3 | 47 | 99.173 | 61.794 | 37.290 | 1.00 | 31.61 |
| 2730 | OH2 | TIP3 | 48 | 106.963 | 58.636 | 47.340 | 1.00 | 36.68 |
| 2731 | OH2 | TIP3 | 49 | 85.142 | 35.133 | 43.034 | 1.00 | 19.23 |
| 2732 | OH2 | TIP3 | 50 | 71.616 | 67.146 | 35.073 | 1.00 | 36.90 |
| 2733 | OH2 | TIP3 | 51 | 75.865 | 23.589 | 68.938 | 1.00 | 31.60 |
| 2734 | OH2 | TIP3 | 52 | 84.026 | 47.614 | 42.760 | 1.00 | 26.85 |
| 2735 | OH2 | TIP3 | 53 | 99.401 | 56.479 | 39.758 | 1.00 | 21.95 |
| 2736 | OH2 | TIP3 | 54 | 68.040 | 27.725 | 53.497 | 1.00 | 43.99 |
| 2737 | OH2 | TIP3 | 55 | 78.583 | 39.197 | 40.332 | 1.00 | 24.68 |
| 2738 | OH2 | TIP3 | 56 | 92.451 | 75.069 | 27.711 | 1.00 | 44.43 |
| 2739 | OH2 | TIP3 | 57 | 89.623 | 49.854 | 35.111 | 1.00 | 22.90 |
| 2740 | OH2 | TIP3 | 58 | 95.616 | 73.094 | 31.597 | 1.00 | 27.62 |
| 2741 | OH2 | TIP3 | 59 | 86.253 | 47.246 | 59.568 | 1.00 | 24.37 |
| 2742 | OH2 | TIP3 | 60 | 98.881 | 56.884 | 37.033 | 1.00 | 32.28 |
| 2743 | OH2 | TIP3 | 61 | 107.913 | 59.670 | 50.434 | 1.00 | 40.73 |
| 2744 | OH2 | TIP3 | 62 | 63.410 | 58.104 | 43.219 | 1.00 | 29.77 |
| 2745 | OH2 | TIP3 | 63 | 99.184 | 62.943 | 48.341 | 1.00 | 52.93 |
| 2746 | OH2 | TIP3 | 64 | 92.483 | 47.893 | 40.686 | 1.00 | 33.31 |
| 2747 | OH2 | TIP3 | 65 | 76.471 | 22.799 | 61.366 | 1.00 | 33.07 |
| 2748 | OH2 | TIP3 | 66 | 102.733 | 70.701 | 43.239 | 1.00 | 52.51 |
| 2749 | OH2 | TIP3 | 67 | 94.669 | 46.032 | 46.815 | 1.00 | 31.75 |
| 2750 | OH2 | TIP3 | 68 | 100.962 | 67.281 | 48.137 | 1.00 | 52.13 |
| 2751 | OH2 | TIP3 | 69 | 76.478 | 37.405 | 40.145 | 1.00 | 25.79 |
| 2752 | OH2 | TIP3 | 70 | 90.165 | 47.004 | 58.770 | 1.00 | 49.51 |
| 2753 | OH2 | TIP3 | 71 | 89.912 | 38.696 | 43.283 | 1.00 | 41.39 |
| 2754 | OH2 | TIP3 | 72 | 78.867 | 77.910 | 30.979 | 1.00 | 43.29 |
| 2755 | OH2 | TIP3 | 73 | 105.807 | 71.061 | 33.955 | 1.00 | 35.91 |
| 2756 | OH2 | TIP3 | 74 | 94.956 | 46.168 | 41.472 | 1.00 | 32.83 |
| 2757 | OH2 | TIP3 | 75 | 81.755 | 20.284 | 64.565 | 1.00 | 36.36 |
| 2758 | OH2 | TIP3 | 76 | 83.777 | 36.376 | 73.095 | 1.00 | 35.68 |
| 2759 | OH2 | TIP3 | 77 | 90.384 | 42.253 | 62.669 | 1.00 | 45.35 |
| 2760 | OH2 | TIP3 | 78 | 88.037 | 29.259 | 75.147 | 1.00 | 56.66 |

FIG. 3A-58

| Atom | Atom Type | Resid | # | X | Y | Z | OCC | B |
|---|---|---|---|---|---|---|---|---|
| 2761 | OH2 | TIP3 | 79 | 101.859 | 65.470 | 26.683 | 1.00 | 39.64 |
| 2762 | OH2 | TIP3 | 80 | 71.347 | 27.770 | 73.090 | 1.00 | 46.49 |
| 2763 | OH2 | TIP3 | 81 | 105.055 | 72.336 | 36.481 | 1.00 | 34.57 |
| 2764 | OH2 | TIP3 | 82 | 89.487 | 32.603 | 43.952 | 1.00 | 55.98 |
| 2765 | OH2 | TIP3 | 83 | 82.955 | 70.726 | 51.485 | 1.00 | 31.53 |
| 2766 | OH2 | TIP3 | 84 | 104.149 | 69.529 | 35.834 | 1.00 | 22.24 |
| 2767 | OH2 | TIP3 | 87 | 97.144 | 58.485 | 29.113 | 1.00 | 38.50 |
| 2768 | OH2 | TIP3 | 88 | 99.143 | 58.146 | 34.137 | 1.00 | 31.08 |
| 2769 | OH2 | TIP3 | 89 | 93.402 | 76.905 | 45.088 | 1.00 | 58.17 |
| 2770 | OH2 | TIP3 | 91 | 98.629 | 61.636 | 27.795 | 1.00 | 44.47 |
| 2771 | OH2 | TIP3 | 93 | 92.075 | 77.451 | 42.668 | 1.00 | 46.15 |
| 2772 | OH2 | TIP3 | 94 | 94.761 | 55.023 | 38.581 | 1.00 | 43.31 |
| 2773 | OH2 | TIP3 | 95 | 94.860 | 63.387 | 30.662 | 1.00 | 23.26 |
| 2774 | OH2 | TIP3 | 97 | 96.495 | 61.394 | 31.222 | 1.00 | 17.95 |
| 2775 | OH2 | TIP3 | 99 | 97.135 | 61.058 | 33.735 | 1.00 | 24.21 |
| 2776 | OH2 | TIP3 | 100 | 98.598 | 62.340 | 24.703 | 1.00 | 15.55 |
| 2777 | OH2 | TIP3 | 101 | 96.091 | 63.609 | 25.209 | 1.00 | 16.64 |
| 2778 | OH2 | TIP3 | 102 | 95.591 | 62.210 | 28.267 | 1.00 | 28.35 |
| 2779 | OH2 | TIP3 | 103 | 84.181 | 68.384 | 51.386 | 1.00 | 37.36 |
| 2780 | OH2 | TIP3 | 104 | 90.542 | 76.184 | 46.889 | 1.00 | 50.54 |
| 2781 | OH2 | TIP3 | 105 | 87.338 | 52.422 | 55.348 | 1.00 | 57.64 |
| 2782 | OH2 | TIP3 | 106 | 86.485 | 55.114 | 55.782 | 1.00 | 53.13 |
| 2783 | OH2 | TIP3 | 107 | 71.978 | 33.253 | 38.083 | 1.00 | 37.67 |
| 2784 | OH2 | TIP3 | 108 | 86.389 | 52.030 | 52.810 | 1.00 | 45.08 |
| 2785 | OH2 | TIP3 | 109 | 88.375 | 44.898 | 51.380 | 1.00 | 45.72 |
| 2786 | OH2 | TIP3 | 110 | 76.040 | 31.693 | 38.282 | 1.00 | 49.11 |
| 2787 | OH2 | TIP3 | 111 | 88.171 | 23.460 | 70.887 | 1.00 | 34.87 |
| 2788 | OH2 | TIP3 | 112 | 81.925 | 26.203 | 48.120 | 1.00 | 34.21 |
| 2789 | OH2 | TIP3 | 113 | 75.036 | 35.002 | 37.397 | 1.00 | 43.93 |
| 2790 | OH2 | TIP3 | 114 | 66.842 | 37.170 | 41.543 | 1.00 | 37.92 |
| 2791 | OH2 | TIP3 | 115 | 74.137 | 22.561 | 64.810 | 1.00 | 39.94 |
| 2792 | OH2 | TIP3 | 116 | 75.230 | 29.105 | 47.361 | 1.00 | 33.31 |
| 2793 | OH2 | TIP3 | 117 | 71.548 | 35.570 | 75.085 | 1.00 | 51.53 |
| 2794 | OH2 | TIP3 | 118 | 91.190 | 40.939 | 65.032 | 1.00 | 59.85 |
| 2795 | OH2 | TIP3 | 119 | 89.208 | 54.691 | 55.131 | 1.00 | 49.67 |
| 2796 | OH2 | TIP3 | 120 | 87.603 | 20.791 | 70.317 | 1.00 | 41.15 |
| 2797 | OH2 | TIP3 | 121 | 82.007 | 24.661 | 44.978 | 1.00 | 44.91 |
| 2798 | OH2 | TIP3 | 122 | 67.254 | 62.385 | 54.134 | 1.00 | 55.45 |
| 2799 | OH2 | TIP3 | 123 | 69.652 | 50.335 | 60.131 | 1.00 | 56.04 |
| 2800 | OH2 | TIP3 | 124 | 91.100 | 35.309 | 64.126 | 1.00 | 10.24 |
| 2801 | OH2 | TIP3 | 125 | 75.803 | 55.613 | 55.160 | 1.00 | 19.38 |
| 2802 | OH2 | TIP3 | 126 | 67.414 | 58.406 | 48.372 | 1.00 | 50.59 |
| 2803 | OH2 | TIP3 | 127 | 61.992 | 60.345 | 41.276 | 1.00 | 54.28 |
| 2804 | OH2 | TIP3 | 128 | 100.397 | 72.990 | 35.528 | 1.00 | 47.93 |
| 2805 | OH2 | TIP3 | 129 | 78.374 | 54.246 | 34.009 | 1.00 | 25.64 |
| 2806 | OH2 | TIP3 | 130 | 74.448 | 74.269 | 39.281 | 1.00 | 43.21 |
| 2807 | OH2 | TIP3 | 131 | 64.202 | 44.752 | 43.474 | 1.00 | 49.87 |
| 2808 | OH2 | TIP3 | 132 | 88.521 | 75.111 | 27.052 | 1.00 | 58.72 |
| 2809 | OH2 | TIP3 | 133 | 69.530 | 56.754 | 48.247 | 1.00 | 28.48 |

FIG. 3A-59

| Atom | Atom Type | Resid | # | X | Y | Z | OCC | B |
|---|---|---|---|---|---|---|---|---|
| 2810 | OH2 | TIP3 | 134 | 79.780 | 77.649 | 41.569 | 1.00 | 58.74 |
| 2811 | OH2 | TIP3 | 135 | 88.780 | 33.735 | 64.655 | 1.00 | 36.24 |
| 2812 | OH2 | TIP3 | 136 | 104.389 | 57.542 | 20.144 | 1.00 | 59.52 |
| 2813 | OH2 | TIP3 | 137 | 64.410 | 59.785 | 53.812 | 1.00 | 52.08 |
| 2814 | OH2 | TIP3 | 138 | 99.184 | 58.625 | 27.266 | 1.00 | 30.88 |
| 2815 | OH2 | TIP3 | 139 | 101.746 | 57.264 | 20.715 | 1.00 | 37.99 |

END

CRYSTALLIZABLE COMPOSITIONS COMPRISING A HEPATITIS C VIRUS NS3 PROTEASE DOMAIN/NS4A COMPLEX

This application claims benefit of Provisional Application 60/025,274, filed Sept. 12, 1996.

TECHNICAL FIELD OF INVENTION

The present invention relates to compositions and crystals of a hepatitis C virus protease in complex with its viral cofactor. This invention also relates to methods of using the structure coordinates of hepatitis C virus protease in complex with a synthetic NS4A to solve the structure of similar or homologous proteins or protein complexes.

BACKGROUND OF THE INVENTION

Infection by hepatitis C virus (HCV) is a compelling human medical problem. HCV is recognized as the causative agent for most cases of non-A, non-B hepatitis, with an estimated human seroprevalence of 1% globally [Choo, Q.-L. et al., "Isolation of a cDNA Clone Derived From a Blood-Borne Non-A, Non-B Viral Hepatitis Genome", *Science*, 244, pp. 359–362 (1989); Kuo, G. et al., "An Assay for Circulating Antibodies to a Major Etiologic Virus of Human Non-A, Non-B Hepatitis", *Science*, 244, pp. 362–364 (1989); Purcell, R. H., "Hepatitis C virus: Historical perspective and current concepts", *FEMS Microbiology Reviews*, 14, pp. 181–192 (1994); Van der Poel, C. L., "Hepatitis C Virus. Epidemiology, Transmission and Prevention in Hepatitis C virus. Current Studies in Hematology and Blood Transfusion, H. W. Reesink, Ed., (Basel: Karger), pp. 137–163 (1994)]. Four million individuals may be infected in the United States alone [Alter, M. J. and Mast, E. E., "The Epidemiology of Viral Hepatitis in the United States, *Gastroenterol. Clin. North Am.*, 23, pp. 437–455 (1994)].

Upon first exposure to HCV only about 20% of infected individuals develop acute clinical hepatitis while others appear to resolve the infection spontaneously. In most instances, however, the virus establishes a chronic infection that persists for decades [Iwarson, S. "The Natural Course of Chronic Hepatitis", *FEMS Microbiology Reviews*, 14, pp. 201–204 (1994)]. This usually results in recurrent and progressively worsening liver inflammation, which often leads to more severe disease states such as cirrhosis and hepatocellular carcinoma [Kew, M. C., "Hepatitis C and Hepatocellular Carcinoma", *FEMS Microbiology Reviews*, 14, pp. 211–220 (1994); Saito, I., et al. "Hepatitis C Virus Infection is Associated with the Development of Hepatocellular Carcinoma", *Proc. Natl. Acad. Sci. USA* 87, pp. 6547–6549 (1990)]. Currently, there are no broadly effective treatments for the debilitating progression of chronic HCV.

The HCV genome encodes a polyprotein of 3010–3033 amino acids (FIG. 1) [Choo, Q.-L., et al. "Genetic Organization and Diversity of the Hepatitis C Virus", *Proc. Natl. Acad. Sci. USA*, 88, pp. 2451–2455 (1991); Kato, N. et al., Molecular Cloning of the Human Hepatitis C Virus Genome From Japanese Patients with Non-A, Non-B Hepatitis", *Proc. Natl. Acad. Sci. USA*, 87, pp. 9524–9528 (1990); Takamizawa, A. et al., "Structure and Organization of the Hepatitis C Virus Genome Isolated From Human Carriers", J. Virol., 65, pp. 1105–1113 (1991)]. The HCV nonstructural (NS) proteins provide catalytic machinery for viral replication. The NS proteins are derived by proteolytic cleavage of the polyprotein [Bartenschlager, R. et al., "Nonstructural Protein 3 of the Hepatitis C Virus Encodes a Serine-Type Proteinase Required for Cleavage at the NS3/4 and NS4/5 Junctions", *J. Virol.*, 67, pp. 3835–3844 (1993); Grakoui, A. et al. "Characterization of the Hepatitis C Virus-Encoded Serine Proteinase: Determination of Proteinase-Dependent Polyprotein Cleavage Sites", *J. Virol.*, 67, pp. 2832–2843 (1993); Grakoui, A. et al., Expression and Identification of Hepatitis C Virus Polyprotein Cleavage Products", *J. Virol.*, 67, pp. 1385–1395 (1993); Tomei, L. et al., "NS3 is a serine protease required for processing of hepatitis C virus polyprotein", *J. Virol.*, 67, pp. 4017–4026 (1993)].

The HCV NS protein 3 (NS3) contains a serine protease activity that helps process the majority of the viral enzymes, and is thus considered essential for viral replication and infectivity. It is known that mutations in the yellow fever virus NS3 protease decreases viral infectivity [Chambers, T. J. et. al., "Evidence that the N-terminal Domain of Nonstructural Protein NS3 From Yellow Fever Virus is a Serine Protease Responsible for Site-Specific Cleavages in the Viral Polyprotein", *Proc. Natl. Acad. Sci. USA*, 87, pp. 8898–8902 (1990)]. The first 181 amino acids of NS3 (residues 1027–1207 of the viral polyprotein) have been shown to contain the serine protease domain of NS3 that processes all four downstream sites of the HCV polyprotein (FIG. 1) [C. Lin et al., "Hepatitis C Virus NS3 Serine Proteinase: Trans-Cleavage Requirements and Processing Kinetics", *J. Virol.*, 68, pp. 8147–8157 (1994)].

NS3 is associated with a cofactor, NS4A. NS4A seems critical to the activity of NS3, enhancing the proteolytic efficiency of NS3 at all of the cleavage sites. NS4A is a 54 residue amphipathic peptide, with a hydrophobic N-terminus and a hydrophilic C-terminus [Failla, C. et al., "Both NS3 and NS4A are Required for Proteolytic Processing of Hepatitis C Virus Nonstructural Proteins", *J. Virol.*, 68, pp. 3753–3760 (1994)]. Its function appears complex, possibly assisting in the membrane-localization of NS3 and other viral replicase components [Lin, C. et al. "A Central Region in the Hepatitis C Virus NS4A Protein Allows Formation of an Active NS3-NS4A Serine Proteinase Complex In Vivo and In Vitro", *J. Virol.*, 69, pp. 4373–4380 (1995b); Shimizu, Y. et al., "Identification of the Sequence on NS4A Required for Enhanced Cleavage of the NS5A/5B Site by Hepatitis C Virus NS3 Protease", *J. Virol.*, 70, pp. 127–132 (1996); Tanji, Y. et al., "Hepatitis C Virus-Encoded Nonstructural Protein NS4A has Versatile Functions in Viral Protein Processing", *J. Virol.*, 69, pp. 1575–1581 (1995)] but its best characterized function is that of a cofactor for the NS3 protease.

The current understanding of HCV has not led to satisfactory treatments for HCV infection. The prospects for effective anti-HCV vaccines remain uncertain. The only established therapy for HCV disease is interferon treatment. However, interferons have significant side effects [Janssen, H. L. A., et al. "Suicide Associated with Alpha-Interferon Therapy for Chronic Viral Hepatitis", *J. Hepatol.*, 21, pp. 241–243 (1994)]; Renault, P. F. and Hoofnagle, J. H., "Side effects of alpha interferon. Seminars in Liver Disease 9, 273–277. (1989)] and induce long term remission in only a fraction (≈25%) of cases [Weiland, O. "Interferon Therapy in Chronic Hepatitis C Virus Infection", *FEMS Microbiol. Rev.*, 14, pp. 279–288 (1994)]. Thus, there is a need for more effective anti-HCV therapies.

The NS3 protease is considered a potential target for antiviral agents. However, drug discovery efforts directed towards the NS3 protein have been hampered by the lack of structural information about NS3 and its complex with NS4A. Such structural information would provide valuable information in discovery of HCV NS3 protease inhibitors.

However, efforts to determine the structure of HCV NS3 protease have been hampered by difficulties in obtaining sufficient quantities of pure active enzyme [Steinkuhler, C. et al., "In Vitro Activity of Hepatitis C Virus Protease NS3 Purified from Recombinant Baculovirus-Infected Sf9 Cells", *J. Biol Chem.*, pp. 637–6273 (1996)]. There have been no crystals reported of any NS3 or NS3 protease domain protein. Thus, x-ray crystallographic analysis of such proteins has not been possible.

SUMMARY OF THE INVENTION

Applicants have solved this problem by providing, for the first time, compositions comprising a hepatitis C virus (HCV) NS3 protease-like polypeptide complexed with a NS4A-like peptide and methods for making such compositions.

The invention also provides crystals of a HCV NS3 protease-like polypeptide/NS4A-like peptide complex and methods for making such crystals.

The invention also provides the structure coordinates of a HCV NS3 protease-like polypeptide/NS4A-like peptide complex.

The invention also provides a method for determining at least a portion of the three-dimensional structure of molecules or molecular complexes which contain at least some structurally similar features to a HCV NS3 serine protease domain.

BRIEF DESCRIPTION OF THE FIGURES

FIG. 3A-1 to FIG. 3A-59 lists the atomic structure coordinates for hepatitis C virus recombinant, truncated non-structural protein 3 (hereafter referred to as tNS3) in complex with a synthetic peptide of the central region of the nonstructural protein 4A (hereafter referred to as sNS4A) as derived by X-ray diffraction from crystals of that complex (hereafter referred to as tNS3/sNS4A). The preparation of the complex is described in Examples 1 and 2. The following abbreviations are used in FIG. 3A-1 to FIG. 3A-59:

Figure 1:
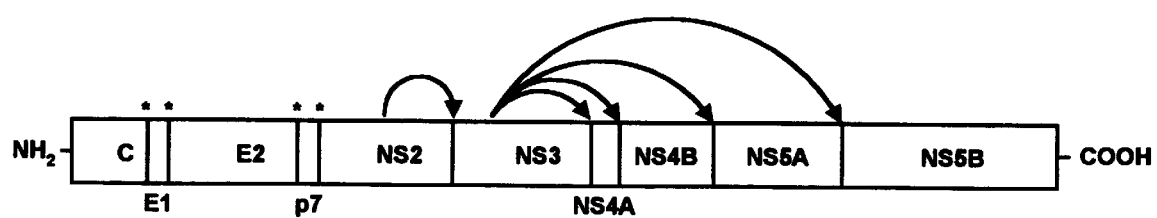
FIG. 1 depicts HCV polyprotein processing. The locations of the HCV structural and nonstructural proteins are marked on a diagram of the 3011 amino acid polypeptide. Cleavages between the structural proteins by cellular signal peptidases are marked by asterisks. Cleavage between NS2 and NS3 is mediated by the NS2/NS3 metallo-protease. The NS3 serine protease is resposible for cleavages between NS3 and NS4A, NS4A and NS4B, NS4B and NS5A, and NS5A and NS5B.
Figure 2:
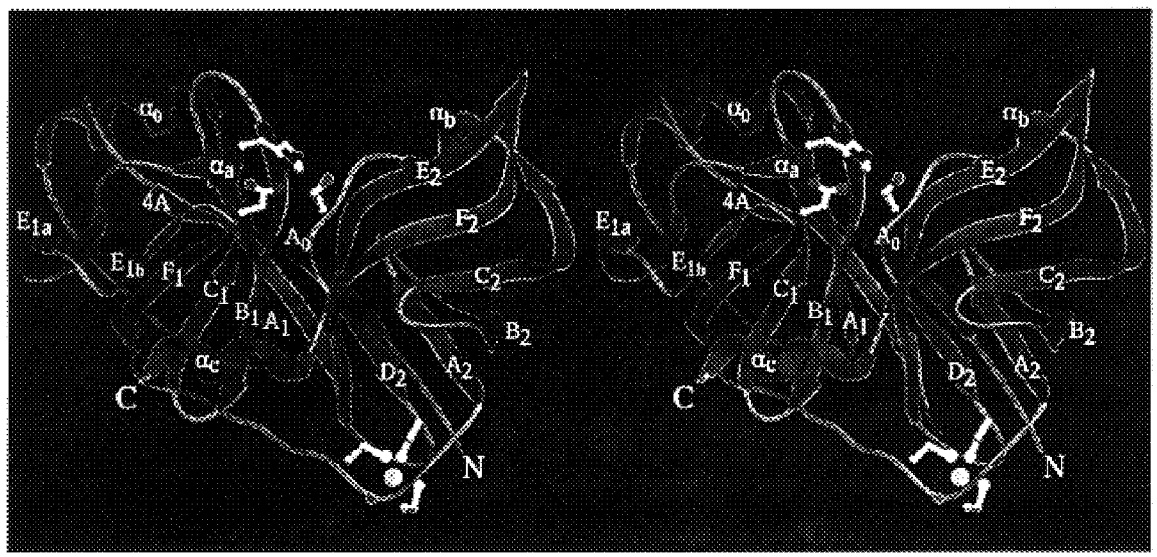
FIG. 2 depicts stereo ribbon diagrams of the NS3/NS4A complex. The view is into the active site cleft of the enzyme. Side-chains of active site residues His-1083, Asp-1107, and Ser-1165, along with $Zn^{++}$ ligands Cys-1123, Cys-1125, and Cys-1171 are displayed in ball-and-stick representation. $Zn^{++}$ is colored cyan and its $H_2O$ ligand red. The β-strand formed by NS4A is shown in magenta.

"Atom type" refers to the element whose coordinates have been determined. Elements are defined by the first letter in the column except for zinc which is defined by the letters "Zn".

"X, Y, Z" crystallographically define the atomic position determined for each atom.

"B" is a thermal factor that measures movement of the atom around its atomic center.

"Occ" is an occupancy factor that refers to the fraction of the molecules in which each atom occupies the position specified by the coordinates. A value of "1" indicates that each atom has the same conformation, i.e., the same position, in all molecules of the crystal.

DETAILED DESCRIPTION OF THE INVENTION

The following abbreviations are used throughout the application:

| | |
|---|---|
| A = Ala = Alanine | T = Thr = Threonine |
| V = Val = Valine | C = Cys = Cysteine |
| L = Leu = Leucine | Y = Tyr = Tyrosine |
| I = Ile = Isoleucine | N = Asn = Asparagine |
| P = Pro = Proline | Q = Gln = Glutamine |
| F = Phe = Phenylalanine | D = Asp = Aspartic Acid |
| W = Trp = Tryptophan | E = Glu = Glutamic Acid |
| M = Met = Methionine | K = Lys = Lysine |
| G = Gly = Glycine | R = Arg = Arginine |
| S = Ser = Serine | H = His = Histidine |

HCV = hepatitis C virus

Additional definitions are set forth in the specification where necessary.

In order that the invention described herein may be more fully understood, the following detailed description is set forth.

Applicants have solved the above problems by providing, for the first time, crystallizable compositions comprising a HCV NS3 protease-like polypeptide in complex with a NS4A-like peptide.

Thus, in one embodiment of this invention is provided a composition comprising a hepatitis C virus NS3-like polypeptide in complex with an NS4A-like peptide.

The HCV NS3-like polypeptide portion of the complex is any polypeptide which has the serine protease activity of the naturally occurring HCV NS3A protease, particularly the ability to cleave the HCV polyprotein. It includes HCV NS3, NS3 protease domain polypeptides and NS3 protease domain-like polypeptides.

As used herein, the terms "HCV NS3" and "NS3" refers to the hepatitis C virus nonstructural-3 protein as defined in Lin, C. et al., "Hepatitis C Virus NS3 Serine Proteinase: Trans-Cleavage Requirements and Processing Kinetics", *J. Virol.*, 68, pp. 8147–8157 (1994).

The term "NS3 protease domain polypeptide" refers to a truncated, serine protease portion of NS3 as defined in [Bartenschlager, R. et al., "Nonstructural Protein 3 of the Hepatitis C Virus Encodes a Serine-Type Proteinase Required for Cleavage at the NS3/4 and NS4/5 Junctions", *J. Virol.*, 67, pp. 3835–3844 (1993); Grakoui, A. et al. "Characterization of the Hepatitis C Virus-Encoded Serine Proteinase: Determination of Proteinase-Dependent Polyprotein Cleavage Sites", *J. Virol.*, 67, pp. 2832–2843 (1993); Grakoui, A. et al., Expression and Identification of Hepatitis C Virus Polyprotein Cleavage Products", *J. Virol.*, 67, pp. 1385–1395 (1993); Tomei, L. et al., "NS3 is a serine protease required for processing of hepatitis C virus polyprotein", *J. Virol.*, 67, pp. 4017–4026 (1993)]. The disclosure of each of these documents is herein incorporated by reference.

The term "NS3 protease domain-like polypeptides" refers to polypeptides that differ from NS3 protease domain polypeptides by having amino acid deletions, substitutions, and additions, but which retain the serine protease activity of NS3.

Preferably, the NS3-like polypeptide in the compositions of this invention is tNS3, a recombinantly produced hepatitis C virus protease domain protein that is prepared as described herein.

The NS4A-like peptide portion of the compositions of this invention is any peptide or peptide mimetic that is capable of acting as a NS4A cofactor for the NS3. These include NS4A, peptide fragments thereof and other peptides that differ from NS4A by having amino acid deletions, substitutions, and additions, while retaining the above-described activity.

As used herein the term "NS4A" refers to the hepatitis C virus nonstructural protein 4A which acts as a cofactor for NS3 protease [Failla, C. et al., "Both NS3 and NS4A are Required for Proteolytic Processing of Hepatitis C Virus Nonstructural Proteins" *J. Virol.* 68, pp. 3753–3760 (1994); Lin, C. et al., "Hepatitis C Virus NS3 Serine Proteinase: Trans-Cleavage Requirements and Processing Kinetics" *J. Virol.* 68, pp. 8147–8157 (1994b)].

Preferably, the NS4A-like peptide is sNS4A, the synthetic peptide H-KKGSVVIVGRIVLSGKPAIIPKK-OH [SEQ ID NO:1]. This peptide encompasses the essential NS3 protease domain residues of NS4A.

Both the NS3-like polypeptide and the NS4A-like peptide may be produced by any well-known method, including synthetic methods, such as solid phase, liquid phase and combination solid phase/liquid phase syntheses; recombinant DNA methods, including cDNA cloning, optionally combined with site directed mutagenesis; and/or purification of the natural products, optionally combined with enzymatic cleavage methods to produce fragments of naturally occurring NS3 and NS4A.

According to a preferred embodiment, the compositions of this invention are crystallizable. In this preferred embodiment all of the preferred choices for the NS3-like polypeptide and the NS4A-like peptide are identical to those indicated above.

Advantageously, the crystallizable composition provided by this invention are amenable to x-ray crystallography. Thus, this invention also provides the three-dimensional structure of an HCV NS3-like polypeptide/NS4A-like peptide complex, specifcally an HCV tNS3/sNS4A complex, at 2.5 Å resolution. Importantly, this has provided for the first time, information about the shape and structure of the NS3 protease domain.

The three-dimensional structure of the HCV tNS3/sNS4A complex of this invention is defined by a set of structure coordinates as set forth in FIG. 3A-1 to FIG. 3A-59. The term "structure coordinates" refers to Cartesian coordinates derived from mathematical equations related to the patterns obtained on diffraction of a monochromatic beam of X-rays by the atoms (scattering centers) of an tNS3/sNS4A complex in crystal form. The diffraction data are used to calculate an electron density map of the repeating unit of the crystal. The electron density maps are then used to establish the positions of the individual atoms of the tNS3/sNS4A enzyme or enzyme complex.

Those of skill in the art will understand that a set of structure coordinates for an enzyme or an enzyme-complex or a portion thereof, is a relative set of points that define a shape in three dimensions. Thus, it is possible that an entirely different set of coordinates could define a similar or identical shape. Moreover, slight variations in the individual coordinates will have little effect on overall shape.

The variations in coordinates discussed above may be generated because of mathematical manipulations of the structure coordinates. For example, the structure coordinates set forth in FIG. 3A-1 to FIG. 3A-59 could be manipulated by crystallographic permutations of the structure coordinates, fractionalization of the structure coordinates, integer additions or subtractions to sets of the structure coordinates, inversion of the structure coordinates or any combination of the above.

Alternatively, modifications in the crystal structure due to mutations, additions, substitutions, and/or deletions of amino acids, or other changes in any of the components that make up the crystal could also account for variations in structure coordinates. If such variations are within an acceptable standard error as compared to the original coordinates, the resulting three-dimensional shape is considered to be the same.

Various computational analyses are therefore necessary to determine whether a molecule or molecular complex or a portion thereof is sufficiently similar to all or parts of the NS3-like polypeptide/NS4A-like peptide structure described above as to be considered the same. Such analyses may be carried out in current software applications, such as the Molecular Similarity application of QUANTA (Molecular Simulations Inc., San Diego, Calif.) version 4.1, and as described in the accompanying User's Guide.

The Molecular Similarity application permits comparisons between different structures, different conformations of the same structure, and different parts of the same structure. The procedure used in Molecular Similarity to compare structures is divided into four steps: 1) load the structures to be compared; 2) define the atom equivalences in these structures; 3) perform a fitting operation; and 4) analyze the results.

Each structure is identified by a name. One structure is identified as the target (i.e., the fixed structure); all remaining structures are working structures (i.e., moving structures). Since atom equivalency within QUANTA is defined by user input, for the purpose of this invention we will define equivalent atoms as protein backbone atoms (N, Cα, C and O) for all conserved residues between the two structures being compared. We will also consider only rigid fitting operations.

When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atom is an absolute minimum. This number, given in angstroms, is reported by QUANTA.

For the purpose of this invention, any molecule or molecular complex that has a root mean square deviation of conserved residue backbone atoms (N, Cα, C, O) of less than 1.5 Å when superimposed on the relevant backbone atoms described by structure coordinates listed in FIG. 3A-1 to FIG. 3A-59 are considered identical. More preferably, the root mean square deviation is less than 1.0 Å.

The term "root mean square deviation" means the square root of the arithmetic mean of the squares of the deviations from the mean. It is a way to express the deviation or variation from a trend or object. For purposes of this invention, the "root mean square deviation" defines the variation in the backbone of a protein or protein complex from the relevant portion of the backbone of the NS3-like polypeptide portion of the complex as defined by the structure coordinates described herein.

Once the structure coordinates of a protein crystal have been determined they are useful in solving the structures of other crystals.

Thus, in accordance with the present invention, the structure coordinates of a NS3-like polypeptide/NS4A-like peptide complex, and in particular a tNS3/sNS4A complex, and portions thereof is stored in a machine-readable storage medium. Such data may be used for a variety of purposes, such as drug discovery and x-ray crystallographic analysis or protein crystal.

Accordingly, in one embodiment of this invention is provided a machine-readable data storage medium comprising a data storage material encoded with the structure coordinates set forth in FIG. 3A-1 to FIG. 3A-59.

In one version of these embodiments, the system includes a computer comprising a central processing unit ("CPU"), a working memory which may be, e.g, RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bidirectional system bus.

Input hardware, coupled to a computer by input lines, may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, a keyboard may also be used as an input device.

Output hardware, coupled to a computer by output lines, may similarly be implemented by conventional devices. By way of example, output hardware may include a CRT display terminal for displaying a graphical representation of a binding pocket of this invention using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage and accesses to and from working memory, and determines the sequence of data processing steps. A number of programs may be used to process the machine-readable data of this invention. Such programs are discussed in reference to the computational methods of drug discovery as described herein. Specific references to components of the hardware system are included as appropriate throughout the following description of the data storage medium.

A magnetic data storage medium can be encoded with a machine-readable data that can be carried out by a system such as the system described above. Medium can be a conventional floppy diskette or hard disk, having a suitable substrate, which may be conventional, and a suitable coating, which may be conventional, on one or both sides, containing magnetic domains (not visible) whose polarity or orientation can be altered magnetically. Medium may also have an opening for receiving the spindle of a disk drive or other data storage device.

The magnetic domains of coating of a medium are polarized or oriented so as to encode in manner which may be conventional, machine readable data such as that described herein, for execution by a system such as the system described above.

An optically-readable data storage medium also can be encoded with such a machine-readable data, or set of instructions, which can be carried out by a system such as the system described above. Medium can be a conventional compact disk read only memory (CD-ROM) or a rewritable medium such as a magneto-optical disk which is optically readable and magneto-optically writable. Medium preferably has a suitable substrate, which may be conventional, and a suitable coating, which may be conventional, usually of one side of the substrate.

In the case of CD-ROM, as is well known, the coating is reflective and is impressed with a plurality of pits to encode the machine-readable data. The arrangement of pits is read by reflecting laser light off the surface of the coating. A protective coating, which preferably is substantially transparent, is provided on top of this coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

For the first time, the present invention permits the use of structure-based or rational drug design techniques to design, select, and synthesize chemical entities, including inhibitory compounds that are capable of binding to HCV NS3, NS4A, NS3/NS4A complex, or any portion thereof.

One particularly useful drug design technique enabled by this invention is iterative drug design. Iterative drug design is a method for optimizing associations between a protein and a compound by determining and evaluating the three-dimensional structures of successive sets of protein/compound complexes.

Those of skill in the art will realize that association of natural ligands or substrates with the binding pockets of their corresponding receptors or enzymes is the basis of many biological mechanisms of action. The term "binding pocket", as used herein, refers to a region of a molecule or molecular complex, that, as a result of its shape, favorably associates with another chemical entity or compound. Similarly, many drugs exert their biological effects through association with the binding pockets of receptors and enzymes. Such associations may occur with all or any parts of the binding pockets. An understanding of such associations will help lead to the design of drugs having more favorable associations with their target receptor or enzyme, and thus, improved biological effects. Therefore, this information is valuable in designing potential ligands or inhibitors of receptors or enzymes, such as inhibitors of HCV NS3-like polypeptides, and more importantly HCV NS3.

The term "associating with" refers to a condition of proximity between chemical entities or compounds, or portions thereof. The association may be non-covalent—wherein the juxtaposition is energetically favored by hydrogen bonding or van der Waals or electrostatic interactions—or it may be covalent.

In iterative drug design, crystals of a series of protein/compound complexes are obtained and then the three-dimensional structures of each complex is solved. Such an approach provides insight into the association between the proteins and compounds of each complex. This is accomplished by selecting compounds with inhibitory activity, obtaining crystals of this new protein/compound complex, solving the three-dimensional structure of the complex, and comparing the associations between the new protein/compound complex and previously solved protein/compound complexes. By observing how changes in the compound affected the protein/compound associations, these associations may be optimized.

In some cases, iterative drug design is carried out by forming successive protein-compound complexes and then crystallizing each new complex. Alternatively, a pre-formed protein crystal is soaked in the presence of an inhibitor, thereby forming a protein/compound complex and obviating the need to crystallize each individual protein/compound complex. Advantageously, the HCV NS3-like polypeptide/ NS4A-like peptide crystals, and in particular the tNS3/ sNS4A crystals, provided by this invention may be soaked in the presence of a compound or compounds, such as NS3 protease inhibitors, to provide NS3-like polypeptide/NS4A-like peptide/compound crystal complexes.

As used herein, the term "soaked" refers to a process in which the crystal is transferred to a solution containing the compound of interest.

In another embodiment of this invention is provided a method for preparing a composition comprising a NS3-like polypeptide protein comprising the steps described in Examples 1 and 2. Preferably, the composition comprises a NS3-like polypeptide in complex with a NS4A-like peptide.

The structure coordinates set forth in FIG. 3A-1 to FIG. 3A-59 can also be used to aid in obtaining structural information about another crystallized molecule or molecular complex. This may be achieved by any of a number of well-known techniques, including molecular replacement.

The structure coordinates set forth in FIG. 3A-1 to FIG. 3A-59 can also be used for determining at least a portion of the three-dimensional structure of molecules or molecular complexes which contain at least some structurally similar features to HCV NS3. In particular, structural information about another crystallized molecule or molecular complex may be obtained. This may be achieved by any of a number of well-known techniques, including molecular replacement.

Therefore, in another embodiment this invention provides a method of utilizing molecular replacement to obtain structural information about a crystallized molecule or molecular complex whose structure is unknown comprising the steps of:

a) generating an X-ray diffraction pattern from said crystallized molecule or molecular complex; and b) applying at least a portion of the structure coordinates set forth in FIG. 3A-1 to FIG. 3A-59 to the X-ray diffraction pattern to generate a three-dimensional electron density map of the molecule or molecular complex whose structure is unknown.

Preferably, the crystallized molecule or molecular complex comprises a NS3-like polypeptide and a NS4A-like peptide. More preferably, the crystallized molecule or molecular complex is obtained by soaking a crystal of this invention in a solution.

By using molecular replacement, all or part of the structure coordinates of the tNS3/sNS4A complex provided by this invention (and set forth in FIG. 3) can be used to determine the structure of a crystallized molecule or molecular complex whose structure is unknown more quickly and efficiently than attempting to determine such information ab initio.

Molecular replacement provides an accurate estimation of the phases for an unknown structure. Phases are a factor in equations used to solve crystal structures that can not be determined directly. Obtaining accurate values for the phases, by methods other than molecular replacement, is a time-consuming process that involves iterative cycles of approximations and refinements and greatly hinders the solution of crystal structures. However, when the crystal structure of a protein containing at least a homologous portion has been solved, the phases from the known structure provide a satisfactory estimate of the phases for the unknown structure.

Thus, this method involves generating a preliminary model of a molecule or molecular complex whose structure coordinates are unknown, by orienting and positioning the relevant portion of the tNS3/sNS4A complex according to FIG. 3A-1 to FIG. 3A-59 within the unit cell of the crystal of the unknown molecule or molecular complex so as best to account for the observed X-ray diffraction pattern of the crystal of the molecule or molecular complex whose structure is unknown. Phases can then be calculated from this model and combined with the observed X-ray diffraction pattern amplitudes to generate an electron density map of the structure whose coordinates are unknown. This, in turn, can be subjected to any well-known model building and structure refinement techniques to provide a final, accurate structure of the unknown crystallized molecule or molecular complex [E. Lattman, "Use of the Rotation and Translation Functions", in *Meth. Enzymol.*, 115, pp. 55–77 (1985); M. G. Rossmann, ed., "The Molecular Replacement Method", *Int. Sci. Rev. Ser., No.* 13, Gordon & Breach, New York (1972)].

The structure of any portion of any crystallized molecule or molecular complex that is sufficiently homologous to any portion of the tNS3/sNS4A complex can be solved by this method.

In a preferred embodiment, the method of molecular replacement is utilized to obtain structural information about a molecule or molecular complex, wherein the complex comprises a NS3-like polypeptide. Preferably the NS3-like polypeptide is tNS3 or homologue thereof.

The structure coordinates of tNS3/sNS4A as provided by this invention are particularly useful in solving the structure of other crystal forms of NS3-like polypeptide, preferably other crystal forms of tNS3; NS3-like polypeptide/NS4A-like peptide, preferably tNS3/sNS4A; or complexes comprising any of the above.

The structure coordinates are also particularly useful to solve the structure of crystals of NS3-like polypeptide/ NS4A-like peptide complexes, particularly tNS3/sNS4A, co-complexed with a variety of chemical entities. This approach enables the determination of the optimal sites for interaction between chemical entities, including interaction of candidate NS3 inhibitors with NS3 or the NS3/NS4A complex. For example, high resolution X-ray diffraction data collected from crystals exposed to different types of solvent allows the determination of where each type of solvent molecule resides. Small molecules that bind tightly to those sites can then be designed and synthesized and tested for their NS3 inhibition activity.

All of the complexes referred to above may be studied using well-known X-ray diffraction techniques and may be refined versus 1.5–3 Å resolution X-ray data to an R value of about 0.20 or less using computer software, such as X-PLOR [Yale University, ©1992, distributed by Molecular Simulations, Inc.; see, e.g., Blundell & Johnson, supra; *Meth. Enzymol.*, vol. 114 & 115, H. W. Wyckoff et al., eds., Academic Press (1985)]. This information may thus be used to optimize known NS3 inhibitors, and more importantly, to design new NS3 inhibitors.

In order that this invention be more fully understood, the following examples are set forth. These examples are for the illustrative purposes only and are not to be construed as limiting the scope of this invention in any way.

EXAMPLE 1

Expression and Purification of tNS3

The truncated NS3 serine protease domain (tNS3) was cloned from a cDNA of the hepatitis C virus H strain

[Grakoui, A. et al., "Expression and Identification of Hepatitis C Virus Polyprotein Cleavage Products", *J. Virol.*, 67, pp. 1385–1395 (1993)]. The first 181 amino acids of NS3 (residues 1027–1207 of the viral polyprotein) have been shown to contain the serine protease domain of NS3 that processes all four downstream sites of the HCV polyprotein [Lin, C., et al., Hepatitis C Virus NS3 Serine Proteinase: Trans-Cleavage Requirements and Processing Kinetics", *J. Virol.* 68, pp. 8147–8157 (1994b)], so we expressed a (His)$_6$-fusion protein based on this tNS3. The plasmid pET-BS(+)/HCV/T7-NS3$_{181}$-His was derived from pTM3/HCV/1027–1207 (NS3$_{181}$) (Id.), by using polymerase chain reaction to introduce epitope tags and new restriction sites. A T7-tag (ASMTGGQQMG), from the N-terminus of the gene 10 protein of the T7 bacteriophage [Tsai, D. E. et al., "In Vitro Selection of an RNA Epitope Immunologically Cross-Reactive With a Peptide", *Proc. Natl. Acad. Sci. USA*, 89, pp. 8864–8868 (1992)], was placed at the N-terminus of the tNS3 domain [SEQ ID NO:2]. Two linker residues (GS) were placed at the tNS3 C-terminus, followed by the (His)$_6$-tag. *E.coli* JM109(DE3) cells, freshly transformed with the pET-BS(+)/HCV/T7-NS3$_{181}$-His plasmid, were grown at 37° C. in complex media supplement with 100 μg/ml ampicillin, in a 10 L fermentor (Braun). When the cell density reached an OD$_{600}$ of 3–4 the temperature of the culture was rapidly reduced to 30° C, and induction was immediately initiated by the addition of 1 mM IPTG. Cells were harvested at 2 h post-induction, and flash frozen at −70° C. prior to purification.

The tNS3 was purified from the soluble fraction of the recombinant *E.coli* lysates as follows, with all procedures being performed at 4° C. unless stated otherwise. Cell paste (75–100 g) was resuspended in 15 volumes of 50 mM HEPES, 0.3 M NaCl, 10% glycerol, 0.1% β-octyl glucoside, 2 mM β-mercaptoethanol, pH 8.0. Cells were ruptured using a microfluidizer and the homogenate was clarified by centrifugation at 100,000×g for 30 min. The supernatant was brought to 50 mM HEPES, 20 mM imidazole, 0.3 M NaCl, 27.5% glycerol, 0.1% β-octyl- glucoside, 2 mM β-mercaptoethanol, pH 8.0, and applied at 1.0 ml/min to a 7.0 ml Ni-Agarose affinity column, equilibrated in the same buffer. After loading, the column was washed with 10–15 volumes of equilibration buffer and the bound proteins were eluted with equilibration buffer containing 0.35 M imidazole. The protein was then size-fractionated on two columns in series (each 2.6cm×90 cm) packed with Pharmacia high resolution S100 resin and equilibrated with 25 mM HEPES, 0.3M NaCl, 10% glycerol, 0.1% β-octylglucoside, 2 mM β-mercaptoethanol, pH 8.0. The tNS3 fractions, identified by SDS-PAGE, were pooled and concentrated to 1 mg/ml using a Amicon Centriprep-10, and stored at −70° C. The tNS3 was thawed slowly on ice and the NS4A peptide (dissolved in the size-exclusion chromatography buffer) was added at a tNS3:NS4A-peptide molar ratio of 1:2. The sample was then diluted 2.5-fold with 15 mM MES, 0.5 M NaCl, 20 mM β-mercaptoethanol, pH6.5, and concentrated to ≈2 ml (≈2 mg/ml) by ultrafiltration. The sample was then diluted 2-fold with the pH 6.5 buffer and concentrated again to ≈2 ml. This dilution process was repeated until it gave a >40-fold dilution of the original buffer constituents. The protein sample was then concentrated to 13.0 mg/ml and centrifuged at ≈300,000×g for 20 min at 4 ° C. Concentrations of the pure tNS3 and tNS3/4A complex were determined by UV absorption spectroscopy, using a molar absorption coefficient (A$_{280}$) of 17,700 M$^{-1}$.cm$^{-1}$.

EXAMPLE 2

4A Peptide Synthesis and Purification

The HCV NS4A peptide was synthesized to span residues Gly21 to Pro39 of the viral cofactor (residues 1678 to 1696 of the HCV polyprotein), which incorporates the essential region reported to be essential for NS3 stimulation [Lin, C. et al. "A Central Region in the Hepatitis C Virus NS4A Protein Allows Formation of an Active NS3-NS4A Serine Proteinase Complex In Vivo and In Vitro", *J. Virol.* 69, pp. 4373–4380 (1995)]. Lysine residues were added to the termini to assist aqueous solubility, and a serine residue was substituted for Cys22 (residue 1679 of the polyprotein of the HCV H strain). The peptide (H-KKGSVVIVGRIVLSGKPAIIPKK-OH.TFA salt) was prepared by the solid-phase peptide synthesis (Applied Biosystems 433A) beginning with N$^α$-Fmoc, N$^ε$-Boc-Lys Wang resin [SEQ ID NO: 1]. N$^α$-Fmoc-protected amino acids were added sequentially using HBTU (2-(1H-benzotriazol-1-yl)1,1,3,3-tetramethyluronium hexafluorophosphate) with HOBt (1-hydroxybenzotriazole hydrate) as coupling agents in N-methylpyrrolidinone. Cleavage from the resin and global deprotection were accomplished with 95% trifluoroacetic acid and 5% water at room temperature for 1.5 hr (15 ml/g resin). The peptide was purified by preparative HPLC on a Waters Delta Pak C18, 15 μm, 300 Å column (30 mm×300 mm) eluting with a linear gradient of acetonitrile (15–40%) in 0.1% aqueous trifluoroacetic acid over 35 min (flow rate of 22 ml/min). Peptide purity was confirmed by analytical HPLC. The sequence was confirmed by direct N-terminal sequence analysis and matrix-assisted laser desorption mass spectrometry (Kratos MALDI I), which showed the correct (M+H)$^+$ and (M+Na)$^+$ molecular ions.

EXAMPLE 3

Crystallization and Data Collection

Crystals of the tNS3/NS4A complex were grown by hanging-drop vapor diffusion over a reservoir of 0.1 M MES, 1.8 M NaCl, 0.1 M sodium/potassium phosphate, 10 nM β-mercaptoethanol, pH 6.5. The crystals grew over the course of 2–3 weeks, to final dimensions of about 0.1×0.1× 0.25 mm. The rhombohedral crystals used in this study belonged to space group R32, with unit cell dimensions a=b=225.0 Å, and c=75.5 Å, and contained two tNS3/NS4A complexes per asymmetric unit.

All heavy atom soaks were done in hanging-drops over the same reservoir as used for crystallization. Crystals were transferred to a stabilizing solution (50 mM MES, 2.0 M NaCl, 0.1 M sodium/potassium phosphate, 10 mM β-mercaptoethanol, and 20% glycerol, pH 6.2) and then frozen in a dry nitrogen gas stream at 100 K (Molecular Structure Corp., Houston, Tex.) for data collection. Data was acquired by oscillation photography on a Rigaku R-AXIS IIC phosphor imaging area detector mounted on a Rigaku RU200 rotating anode generator (MSC), operating at 50 kV and 100 mA. Measured intensities were integrated, scaled, and merged using the HKL software package (Z. Otwinowski and W. Minor).

EXAMPLE 4

Phasing, Model Building and Refinement

Heavy atom positions were located by inspection and confirmed with difference Fourier syntheses. Heavy atom parameters were refined and phases computed to 3.1 Å using the program PHASES [Furey, W. and Swaminathan, S. "PHASES-95: a program package for the processing and analysis of diffraction data from macromolecules", *Meth. Enzymol.*, (1996). MIR phases were improved and extended to 2.7 Å by cycles of solvent flattening [Wang, B. C., "Resolution of Phase Ambiguity in Macromolecular Crystallography", *Methods in Enzymol.* 115, pp. 90–112 (1985)] combined with histogram matching [Zhang, K. Y. J. and Main, P., "The Use of Sayre's Equation With Solvent Flattening and Histogram Matching for Phase Extension and Refinement of Protein Structures", *Acta Crystallogr.,* A46, pp. 377–381 (1990)] using the CCP4 crystallographic package (Collaborative Computation Project, 1994). The resulting electron density map displayed nearly continuous density for the protein backbone as well as strong side chain density. Approximately 80% of the model could be unambiguously built into this map (QUANTA 4.1, Molecular Simulations), and a single round of simulated annealing refinement in X-PLOR [Brunger, A. T., "X-PLOR: A System for X-Ray Crystallography and NMR", New Haven, Ct.: Department of Molecular Biophysics and Biochemistry, Yale University (1993)] brought the R-factor to 29% and free R value to 33% [Brunger, A. T., "Free R Value: A Novel Statistical Quantity for Assessing the Accuracy of Crystal Structures", *Nature,* 355, pp. 472–475 (1992)]. The remainder of the model was built and refined in several steps, by first extending the resolution to 2.5 Å and then adding well-ordered water molecules. A final round of positional and individual temperature factor refinement brought the R-factor to 21.6% (free R value 26.1%) for 26,652 reflections between 6.0 and 2.5 Å (F>1sF). The current model consisted of tNS3 residues 1055–1206 and NS4A residues 1678–1693 in complex A, and tNS3 residues 1028–1206 and NS4A residues 1678–1696 for complex B (polyprotein numbering, with 2 zinc atoms and 130 water molecules. A Ramachandran plot for the final model contained 91% of the residues in the most favored regions and 0% in disallowed or generously-allowed regions. The rms deviations from ideality were 0.007 Å for bond lengths and 1.47° for bond angles.

While we have described a number of embodiments of this invention, it is apparent that our basic examples may be altered to provide other embodiments which utilize the products and processes of this invention. Therefore, it will be appreciated that the scope of this invention is to be defined by the appended claims rather than by the specific embodiments which have been represented by way of example.

We claim:

1. A crystallizable composition comprising a HCV NS3-like polypeptide complexed with a NS4A-like peptide, wherein the NS4A-like peptide is H-KKGSVVIVGRIVLSGXPMVICK-OH (SEQ ID NO: 1).

2. The composition according to claim 1, wherein the HCV NS3-like polypeptide is a NS3 protease domain polypeptide or a NS3 protease domain-like polypeptide.

3. The composition according to claim 1, wherein the HCV NS3-like polypeptide is tNS3.

4. A crystal comprising a HCV NS3-like polypeptide complexed with a NS4A-like peptide, wherein the NS4A-like peptide is H-KKGSVVIVGRIVLSGKPAIIPKK-OH (SEQ ID NO: 1).

5. The crystal according to claim 4, wherein the HCV NS3-like polypeptide is a NS3 protease domain polypeptide or a NS3 protease domain-like polypeptide.

6. The crystal according to claim 4, wherein the HCV NS3-like polypeptide is tNS3.

7. A composition comprising a HCV NS3-like polypeptide completed with a NS4A-like peptide, wherein the NS4A-like peptide is H-KKGSVVIVGRIVLSGKPAIIPKK-OH *SEQ ID NO:1).

8. The composition according to claim 7, wherein the HCV NS3-like polypeptide is a NS3 protease domain polypeptide or a NS3 protease domain-like polypeptide.

9. The composition according to claim 7, wherein the HCV NS3-like polypeptide is tNS3.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 23 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:1:

Lys Lys Gly Ser Val Val Ile Val Gly Arg Ile Val Leu Ser Gly Lys
1             5                  10               15

Pro Ala Ile Ile Pro Lys Lys
        20

(2) INFORMATION FOR SEQ ID NO:2:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:2:

-continued

```
Ala Ser Met Thr Gly Gly Gln Gln Met Gly
1               5                   10
```